(12) United States Patent
Haimovitch-Yogev et al.

(10) Patent No.: US 12,254,130 B2
(45) Date of Patent: Mar. 18, 2025

(54) SYSTEM AND METHOD FOR THE DIAGNOSIS AND TREATMENT OF AMBLYOPIA USING A 3D DISPLAY

(71) Applicant: BLINK TECHNOLOGIES INC., Palo Alto, CA (US)

(72) Inventors: Oren Haimovitch-Yogev, Haifa (IL); Gilad Drozdov, Haifa (IL); Almog David, Kiryat Motzkin (IL)

(73) Assignee: BLINK TECHNOLOGIES INC., Palo Alto, CA (US)

( * ) Notice: Subject to any disclaimer, the term of this patent is extended or adjusted under 35 U.S.C. 154(b) by 151 days.

(21) Appl. No.: 18/123,280

(22) Filed: Mar. 19, 2023

(65) Prior Publication Data
US 2023/0233072 A1   Jul. 27, 2023

Related U.S. Application Data

(63) Continuation-in-part of application No. 17/971,601, filed on Oct. 23, 2022, now Pat. No. 12,093,835, and
(Continued)

(51) Int. Cl.
*G06F 3/01* (2006.01)
*A61B 3/00* (2006.01)
(Continued)

(52) U.S. Cl.
CPC ............. *G06F 3/012* (2013.01); *A61B 3/0091* (2013.01); *A61B 3/113* (2013.01); *A61B 3/14* (2013.01);
(Continued)

(58) Field of Classification Search
CPC ......... A61B 3/0091; A61B 3/113; A61B 3/14; A61B 3/022; A61B 3/032; A61H 5/005;
(Continued)

(56) References Cited

U.S. PATENT DOCUMENTS

2014/0300859 A1\* 10/2014 Oz ................. G02B 27/017
351/201
2017/0272729 A1\* 9/2017 Kass ................. H04N 13/117
(Continued)

*Primary Examiner* — Premal R Patel
(74) *Attorney, Agent, or Firm* — AlphaPatent Associates Ltd.; Daniel J. Swirsky

(57) ABSTRACT

Methods, systems, and storage media for projecting a viewer-specific 3D object perspectives from a single 3D display are disclosed. Implementations may: acquire face and eye region image data of a plurality of viewers within a field of view of at least one camera associated with a 3D-enabled digital display; analyze the eye region image data to determine at least one 3D eye position, at least one eye state, at least one gaze angle, and at least one point-of-regard for a viewer relative to at least one camera associated with the 3D-enabled digital display; and calculate a plurality of processed image projections for display by the single 3D display. The digital-processing of input image projection enables a separate optical input to the user's eyes, and by the use of visual-acuity pre-processing of the image—via visual-field kernel, enables the treatment of eye abbreviations, including an Amblyopic-eye without the need for any additional eye-ware, or head-up-displays (HMD's).

31 Claims, 38 Drawing Sheets

Related U.S. Application Data a continuation-in-part of application No. 17/971,600, filed on Oct. 23, 2022, now Pat. No. 11,829,523, and a continuation-in-part of application No. 17/376,388, filed on Jul. 15, 2021, now Pat. No. 12,026,980.

(51) Int. Cl.
| | | |
|---|---|---|
| *A61B 3/113* | (2006.01) | |
| *A61B 3/14* | (2006.01) | |
| *A61H 5/00* | (2006.01) | |
| *G06T 7/00* | (2017.01) | |
| *G06T 7/246* | (2017.01) | |
| *G06T 7/73* | (2017.01) | |
| *H04N 13/302* | (2018.01) | |
| *H04N 13/327* | (2018.01) | |
| *H04N 13/383* | (2018.01) | |

(52) U.S. Cl.
CPC ........... *A61H 5/005* (2013.01); *G06T 7/0012* (2013.01); *G06T 7/246* (2017.01); *G06T 7/73* (2017.01); *H04N 13/302* (2018.05); *H04N 13/327* (2018.05); *H04N 13/383* (2018.05); *G06T 2207/30041* (2013.01); *G06T 2207/30201* (2013.01)

(58) Field of Classification Search
CPC ......... G06T 7/0012; G06T 7/246; G06T 7/73; G06T 2207/30041; G06T 2207/30201; H04N 13/302; H04N 13/327; H04N 13/383; H04N 13/279; G06F 3/012
See application file for complete search history.

(56) References Cited

U.S. PATENT DOCUMENTS

| | | | | |
|---|---|---|---|---|
| 2017/0287112 A1* | 10/2017 | Stafford | .................. | G06F 3/013 |
| 2017/0340200 A1* | 11/2017 | Blaha | .................. | A61B 3/0033 |
| 2017/0365101 A1* | 12/2017 | Samec | .................. | G06T 19/006 |

\* cited by examiner

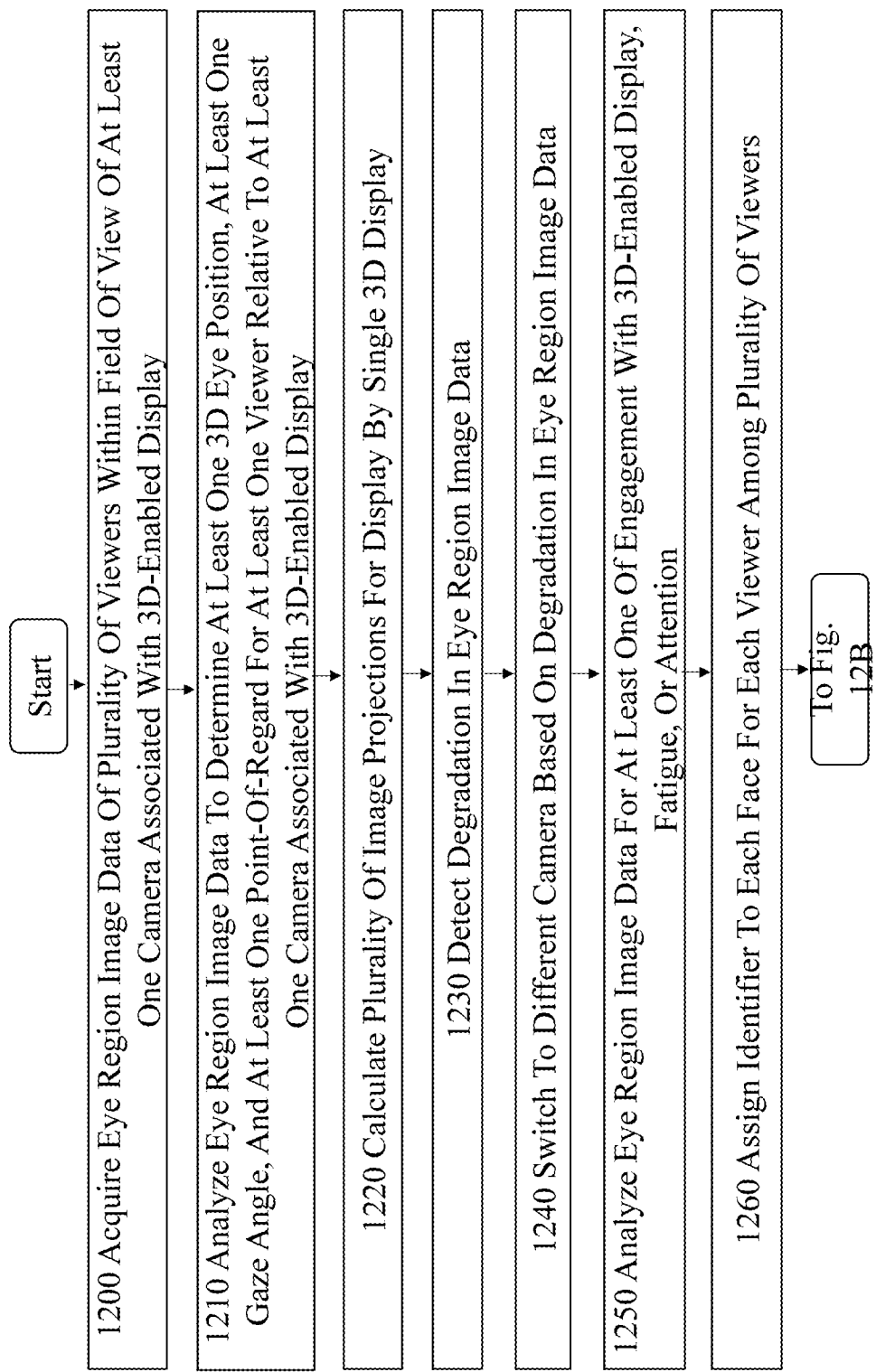

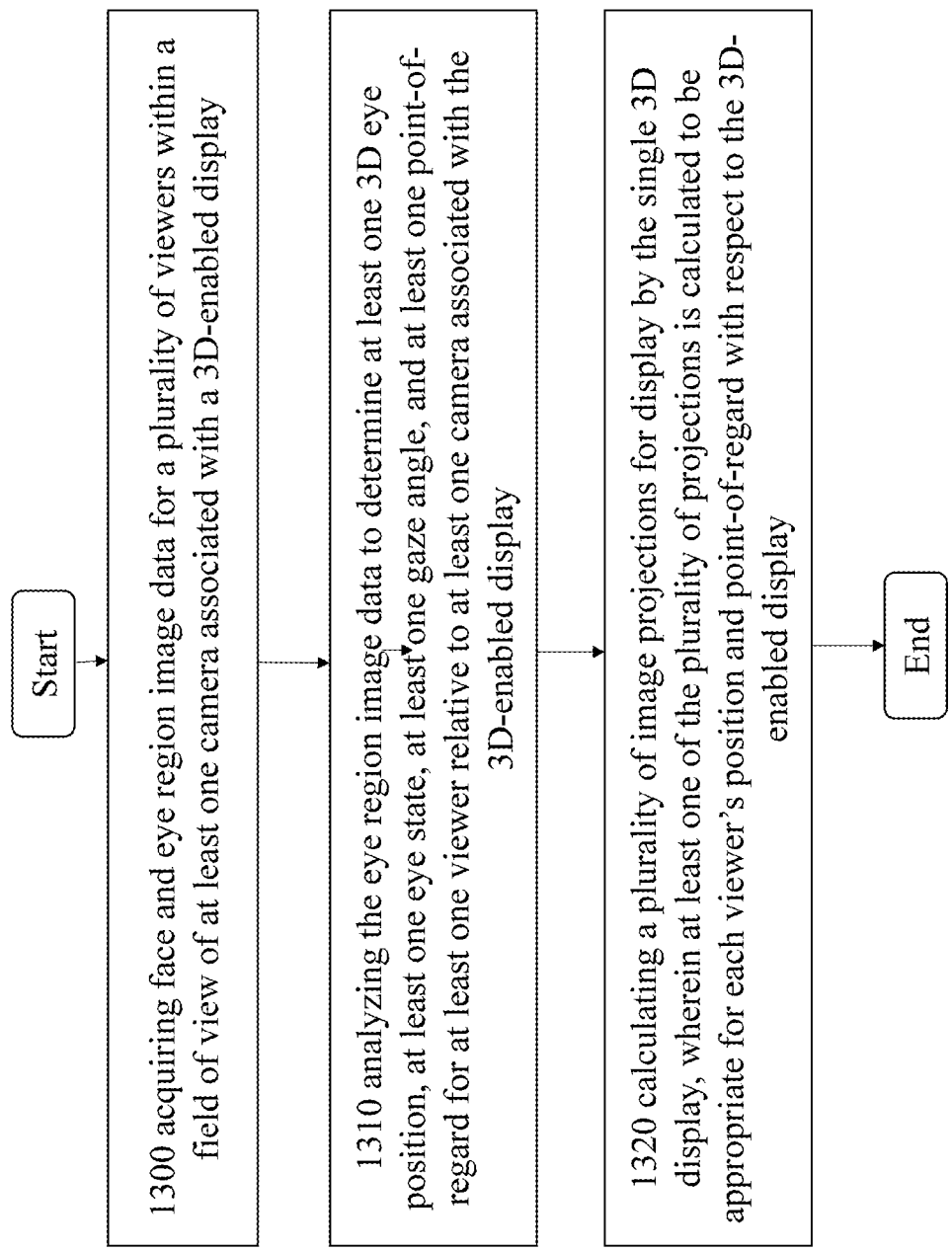

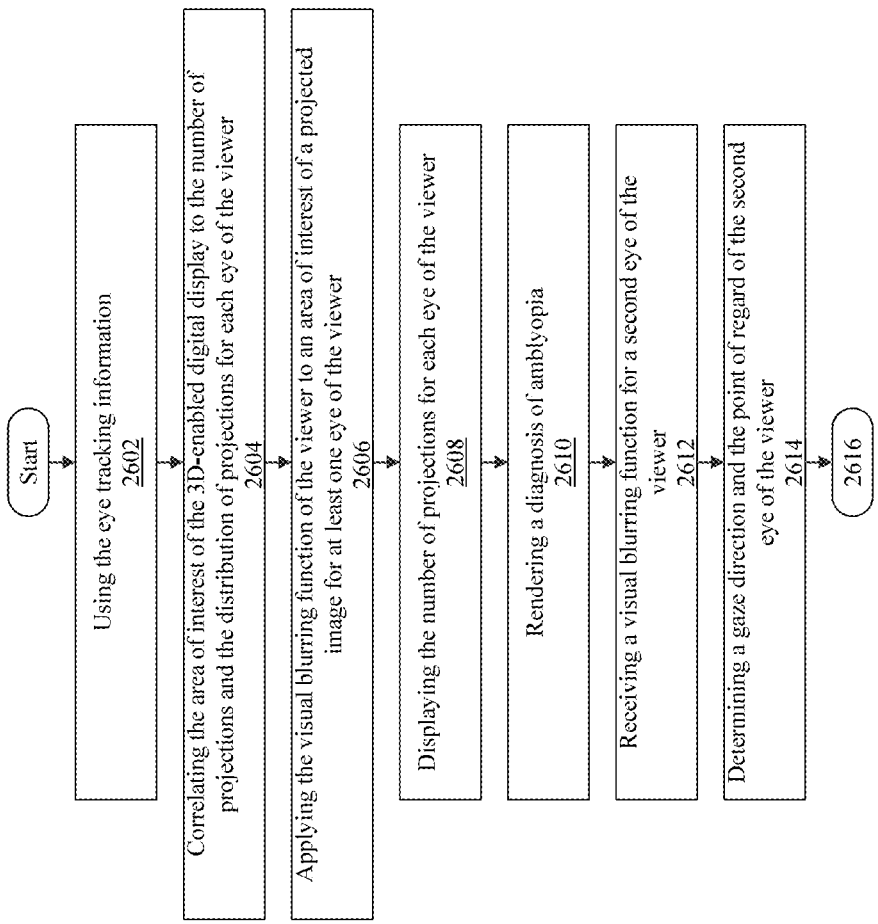

SYSTEM AND METHOD FOR THE DIAGNOSIS AND TREATMENT OF AMBLYOPIA USING A 3D DISPLAY

CROSS-REFERENCE TO RELATED APPLICATIONS

The present application is a continuation in part of co-owned U.S. patent application Ser. No. 17/376,388 filed on Jul. 15, 2021 titled "PUPIL ELLIPSE-BASED, REAL-TIME IRIS LOCALIZATION" by Drozdov et al.; and a continuation in part of co-owned U.S. patent application Ser. No. 17/971,601 filed on Oct. 23, 2022, titled "GEOMETRICALLY CONSTRAINED, UNSUPERVISED TRAINING OF CONVOLUTIONAL AUTOENCODERS FOR EXTRACTION OF EYE LANDMARKS" by Haimovitch-Yogev et al.; and a continuation in part of co-owned U.S. patent application Ser. No. 17/971,600 filed on Oct. 23, 2022, titled "SYSTEMS AND METHODS FOR ANATOMY-CONSTRAINED GAZE ESTIMATION" by Drozdov et al., which are all hereby incorporated by reference herein in their entirety as though fully set forth herein, to the extent that they are not inconsistent with the instant disclosure.

FIELD OF THE INVENTION

The present application relates to generally to naked-eye three-dimensional (3D) displays and more specifically to face and gaze-tracking via digital cameras, for the diagnosis and treatment of amblyopia via a Gaze-Guided 3D Display optimized for displaying a foveated rendering of a video input to the targeted eye in three-dimensional space, without the need for eyewear or a head-mounted-display (HMD).

BACKGROUND

Computer displays are more common today than ever before and continue to be even more widespread through all aspects of society. Personal displays include laptop and desktop computer displays, gaming displays, automotive displays (including heads-up displays) and mobile device displays. Examples of displays that are particularly suited to viewing by single or multiple people include, but are not limited to, informational displays (e.g., for flight information at an airport or directories), retail displays (e.g., for advertising and sales), entertainment displays (e.g., televisions), large venue displays (e.g., at sporting events or concerts), and even infotainment displays in homes and vehicles.

Display technologies have continued to evolve and now include naked-eye three-dimensional (3D) displays that are capable of projecting object images to each eye of a viewer to create an illusion of depth without the need for any eyewear wearable or head-mounted-display (HMD). Various kinds of 3D display technologies are under development, including stereoscopic displays, volumetric displays, light-field displays, and holographic displays, as discussed in more detail below.

Gaze tracking or eye tracking technology as described herein can improve the user experience with 3D displays by locating the point of regard of each eye of each viewer and its 3D-location in space w.r.t display, thereby informing the processing of images and image rendering for each viewer and each viewer's eye, ensuring that the appropriate projections are shown the viewer given their head position and direction of gaze, and their eye location in 3D-space relative to the display screen or projection location. The instant application also provides methods and systems for evaluating and selecting for processing only those image feeds that are useful in determining 3D projections.

Accordingly, the present application provides improved face landmark detection, eye tracking, and camera image evaluation for more accurate and efficient processing and rendering of 3D projections from 3D displays allowing for the diagnosis and treatment of Amblyopia.

BRIEF SUMMARY

Embodiments of the present disclosure include deep learning systems for face detection, face landmark detection, and gaze tracking; as well as camera output evaluation for personalized rendering from one or more 3D displays and digital manipulation to an optical image projection to the user's eyes, to enable treatment for Amblyopic eye.

Embodiments of the present disclosure may include a method for enabling projection of images from a 3D digital display, the method including obtaining face image data and eye region image data for a viewer within a field of view of at least one camera in proximity to a 3D-enabled digital display. Embodiments may also include detecting face and eye landmarks for the viewer in one or more image frames based on the face image data.

Embodiments may also include determining head pose information based on the face image data and eye region image data. Embodiments may also include determining eye tracking information for the viewer based on the face image data, eye region image data, and head pose information, the eye tracking information including a point of regard (POR) of each eye of the viewer.

Embodiments may also include eye state of each eye of the viewer. Embodiments may also include gaze direction of each eye of the viewer. Embodiments may also include eye region illumination information for each eye of the viewer. Embodiments may also include a position of each eye of the viewer relative to the 3D-enabled digital display.

Embodiments may also include receiving a visual blurring function for each eye of the viewer. Embodiments may also include determining a count of projections and a three-dimensional distribution of the projections for each eye of the viewer based on the eye tracking information. Embodiments may also include determining a spatial blurring attribute for the number of projections for each eye of the viewer based at least in part on the received visual blurring function of the viewer.

Embodiments may also include receiving a visual blurring function of the viewer may include receiving a contrast sensitivity function (CSF) indicative of a visual acuity field of the viewer, also termed modulation transfer function, provides a characterization of its frequency response. The contrast sensitivity function can be represented by a spatial (operating on a digital image is presented) bandpass filter determining the visibility of feature to the human-eye and its perception to details in time and space. Embodiments may also include a contrast sensitivity function (CSF) indicative of a visual acuity (VA) of the viewer may include data indicative of a performance of a contrast function sensitivity performance.

Embodiments may also include a contrast sensitivity function (CSF) indicative of a visual acuity of the viewer may include a mathematical function for a Visual Blurring Function (VBF) as a function of time. In some embodiments, the mathematical function may include at least one variable for each of a treatment function for each eye of the viewer.

Embodiments may also include a two-dimensional boundary of a Point of Regard for each eye of the viewer. Embodiments may also include a distance between at least one eye of the viewer and the two-dimensional boundary of the area of focus for at least one eye of the viewer. Embodiments may also include at least one projection.

In some embodiments, the method, may include rendering a first two-dimensional treatment area in three-dimensional space for each eye of the viewer based at least in part on the mathematical function at time t0. Embodiments may also include displaying the rendering of the first two-dimensional treatment area in three-dimensional space for each eye of the viewer. Embodiments may also include determining a visual acuity field for each eye of the viewer in response to the displayed rendering of the first treatment area for each eye of the viewer at time t0.

In some embodiments, the method may include comparing the visual acuity performance for each eye of the viewer at time t0 with a historical visual acuity performance for each eye of the viewer. Embodiments may also include updating the visual blurring function for at least one eye of the viewer if the comparison indicates a change in the visual acuity performance for the at least one eye.

In some embodiments, the updating the visual blurring function for at least one eye of the viewer if the comparison indicates a change in the visual acuity performance for the at least one eye, the change in visual acuity may include at least one of an indication of an improvement in visual acuity and a deterioration in visual acuity. Embodiments may also include a contrast sensitivity function (CSF) indicative of a visual acuity of the viewer may include data indicative of a performance of a spatial frequency sensitivity performance.

Embodiments may also include a contrast sensitivity function (CSF) indicative of a visual acuity of the viewer may include a function indicative of a visual acuity performance of the user at a distance from the 3D-enabled digital display and its minimal Spatial Frequency Threshold for a trackable object on the digital display. Embodiments may also include receiving a visual blurring function of the viewer may include receiving viewer digital identification data indicative of the viewer. Embodiments may also include transmitting a request for a visual acuity profile of the viewer. Embodiments may also include receiving the visual acuity profile. In some embodiments, the visual acuity profile includes at least the visual blurring function of the viewer.

Embodiments may also include receiving the visual acuity profile may include an amblyopic eye classification for each eye of the viewer. Embodiments may also include receiving a visual blurring kernel of the viewer may include receiving a contrast sensitivity function (CSF). In some embodiments, the contrast sensitivity function (CSF) may include at least one instruction for determining the spatial blurring attribute based at least in part on one or more visual acuity fields of the viewer.

Embodiments may also include at least one instruction for determining the spatial blurring attribute based at least in part on one or more visual acuity field of the viewer, the one or more visual acuity field may include at least one of a foveal visual acuity field. Embodiments may also include a para-foveal visual acuity field. Embodiments may also include a peripheral visual acuity field.

Embodiments may also include displaying the number of projections for each eye of the viewer based on the received visual blurring kernel of the viewer may include dynamically altering the spatial blurring attribute for the number of projections for each eye of the viewer as a function of time.

Embodiments may also include dynamically, in time-space, altering the spatial blurring attribute for the number of projections for each eye of the viewer as a function of time may include altering the dimensions of the area of the spatial blurring attribute within the foveal visual acuity field of an eye of the viewer. In some embodiments, altering the dimensions of the area of the spatial blurring attribute to maintain a cognitive load.

In some embodiments, the method may include displaying the number of projections for each eye of the viewer based on the received visual blurring kernel of the viewer. Embodiments may also include dynamically altering the spatial blurring attribute for the number of projections for each eye of the viewer as a function of time may include altering the dimensions of the area of the spatial blurring attribute within the foveal visual acuity field of an eye of the viewer as a function of time.

Embodiments may also include dynamically altering the spatial blurring attribute for the number of projections for each eye of the viewer as a function of time may include altering the dimensions of the area of the spatial blurring attribute within the foveal visual acuity field of an eye of the viewer as a sinusoidal function of time. Embodiments may also include altering the dimensions of the area of the spatial blurring attribute to maintain a cognitive load may include inferring the cognitive load from the eye tracking information.

Embodiments may also include determining a count of projections and a three-dimensional distribution of the projections for each eye of the viewer based on the eye tracking information may include determining the count of projections based at least in part on one or more of a refresh rate of the 3D-enabled digital display, a defined segment of video, a sampling rate of at least one camera of the 3D-enabled digital display, and the visual blurring function for each eye of the viewer.

Embodiments may also include determining an image attribute for the number of projections for each eye of the viewer based on the received visual blurring kernel of the viewer may include using the eye tracking information to determine an area of interest of the 3D-enabled digital display. Embodiments may also include correlating the area of interest of the 3D-enabled digital display to the number of projections and the distribution of projections for each eye of the viewer. Embodiments may also include applying the visual blurring kernel of the viewer to an area of interest of a projected image for at least one eye of the viewer.

Embodiments may also include applying the visual blurring function of the viewer to an area of interest of a projected image for the at least one eye of the viewer may include spatially-adjusting the area of interest of the projected image for the at least one eye. In some embodiments, the method may include using the eye tracking information to determine an area of interest via the point-of-regard of the 3D-enabled digital display. Embodiments may also include correlating the area of interest of the 3D-enabled digital display to the number of projections and the distribution of projections for each eye of the viewer.

Embodiments may also include applying the visual blurring function of the viewer to an area of interest of a projected image for at least one eye of the viewer. Embodiments may also include spatially-adjusting the area of interest of the projected image for the at least one eye. Embodiments may also include displaying the number of projections for each eye of the viewer based on the received visual blurring function of the viewer.

In some embodiments, the method for assessing the visual acuity of a viewer of a 3D display may include rendering a diagnosis of amblyopia based at least in part on the assessment of the ability of the viewer to follow a movement of the at least one object of interest towards the second location and an ability of the viewer to fixate on the at least one object.

In some embodiments, the visual blurring function for each of the eyes of the viewer may be associated with the viewer in a digital record, the digital record including at least one of a viewer identification, an age appropriate content for 3D display, an interest appropriate content for 3D display, insurance carrier information, a prescribing medical professional, and an access frequency for administering treatment.

In some embodiments, the method, the method further including receiving a visual blurring function for a second eye of the viewer. Embodiments may also include determining a gaze direction and the point of regard of the second eye of the viewer with regard to the 3D display. Embodiments may also include rendering a dynamic viewing session containing at least one object of interest.

In some embodiments, the dynamic viewing session may include a plurality of images for projection by the 3D display for the second eye, the rendering based at least in part on the visual blurring function for the second eye, the determined gaze direction and the point of regard of the second eye of the viewer, and the at least one object of interest.

Embodiments may also include performing an assessment of an ability of the second eye to follow a movement of the at least one object of interest and an ability of the second eye of the viewer to fixate on the at least one object. Embodiments may also include adjusting spatially and temporally the at least one object in the rendered dynamic viewing session based at least in part on the assessment.

In some embodiments, the method, the method further including conducting a calibration of the 3D display system. Embodiments may also include conducting a calibration of the 3D display may include obtaining face image data and eye region image data for a viewer within a field of view of at least one camera in proximity to a 3D-enabled digital display. Embodiments may also include detecting face and eye landmarks for the viewer in one or more image frames based on the face image data.

Embodiments may also include determining head pose information based on the face image data and eye region image data. Embodiments may also include determining eye tracking information for the viewer based on the face image data, eye region image data, and head pose information, the eye tracking information including a point of regard (POR) of each eye of the viewer.

Embodiments may also include eye state of each eye of the viewer. Embodiments may also include gaze direction of each eye of the viewer. Embodiments may also include eye region illumination information for each eye of the viewer. Embodiments may also include a position of each eye of the viewer relative to the 3D-enabled digital display.

Embodiments of the present disclosure may also include a method for assessing a visual acuity of a viewer of a 3D display, the method including using the 3D display to project a first sequence of images in three-dimensional space containing at least one object of interest. Embodiments may also include determining a first area of interest of each eye of the viewer via a point of regard.

Embodiments may also include determining a first level of fixation of each eye of the viewer. Embodiments may also include correlating the determined area of interest of each eye of the viewer with the determined fixation of each eye of the viewer. Embodiments may also include using the 3D display to project a second sequence of image in three-dimensional space containing at least one object of interest in a second location.

Embodiments may also include determining a second area of interest of each eye of the viewer. Embodiments may also include determining a second level of fixation of each eye of the viewer. Embodiments may also include correlating the determined area of interest of each eye of the viewer with the determined second area of fixation of each eye of the viewer. Embodiments may also include assessing an ability of the viewer to follow a movement of the at least one object of interest towards the second location and an ability of the viewer to fixate on the at least one object.

In some embodiments, the method may include prescribing a prescription for a treatment of amblyopia using a 3D display. In some embodiments, the prescription may include a visual blurring function for each of the eyes of the viewer. Embodiments may also include a desired performance to fixate on an object of interest. Embodiments may also include a desired ability of the viewer to follow a movement of the object of interest.

Embodiments of the present disclosure may also include a method for treating amblyopia in a user using a 3D display, the method including receiving a visual blurring function for a first eye of the viewer. Embodiments may also include determining a gaze direction and the point of regard of the first eye of the viewer with regard to the 3D display. Embodiments may also include rendering a dynamic viewing session containing at least one object of interest.

In some embodiments, the dynamic viewing session may include a plurality of images for projection by the 3D display for the first eye, the rendering based at least in part on the visual blurring function for the first eye, the determined gaze direction and the point of regard of the first eye of the viewer, and the at least one object of interest. Embodiments may also include performing an assessment of an ability of the first eye to follow a movement of the at least one object of interest and an ability of the first eye of the viewer to fixate on the at least one object. Embodiments may also include adjusting spatially and temporally the at least one object in the rendered dynamic viewing session based at least in part on the assessment.

Embodiments of the present disclosure may also include a computer program product including instructions which, when executed by a computer, cause the computer to carry out the following steps obtaining face image data and eye region image data for a viewer within a field of view of at least one camera in proximity to a 3D-enabled digital display. Embodiments may also include obtaining a distance between the viewer and the 3D-enabled digital display.

Embodiments may also include determining a point of regard of the viewer of the 3D-enabled digital display. Embodiments may also include associating the point of regard of the viewer of the 3D-enabled digital display with a region of media displayed by the 3D-enabled digital display. Embodiments may also include applying a visual blurring function associated with at least one eye of the viewer to at least a portion of the region of media displayed by the 3D-enabled digital display.

In some embodiments, the computer program product, may include receiving a visual blurring function of the viewer. Embodiments may also include receiving a visual blurring function of the viewer may include receiving a contrast sensitivity function (CSF) indicative of a visual acuity field of the viewer.

Embodiments may also include a contrast sensitivity function (CSF) indicative of a visual acuity of the viewer may include data indicative of an amblyopic performance of a contrast function sensitivity performance. Embodiments may also include a contrast sensitivity function (CSF) indicative of a visual acuity of the viewer may include data indicative of a performance of a spatial frequency sensitivity performance.

Embodiments may also include a contrast sensitivity function (CSF) indicative of a visual acuity of the viewer may include a function indicative of a visual acuity performance of the user at a distance from the 3D-enabled digital display and its minimal Spatial Frequency Threshold for a trackable object on the digital display. Embodiments may also include receiving a visual blurring function of the viewer may include receiving viewer digital identification data indicative of the viewer. Embodiments may also include transmitting a request for a visual acuity profile of the viewer. Embodiments may also include receiving the visual acuity profile. In some embodiments, the visual acuity profile includes at least the visual blurring function of the viewer.

Embodiments may also include a contrast sensitivity function (CSF) indicative of a visual acuity of the viewer may include a mathematical function for a Visual Blurring Function (VBF) as a function of time. In some embodiments, the mathematical function may include at least one variable for each of a treatment function for each eye of the viewer.

Embodiments may also include a two-dimensional boundary of a Point of Regard for each eye of the viewer. Embodiments may also include a distance between at least one eye of the viewer and the two-dimensional boundary of the area of focus for at least one eye of the viewer. Embodiments may also include at least one projection.

In some embodiments, the computer program product, may include rendering a first two-dimensional treatment area in three-dimensional space for each eye of the viewer based at least in part on the mathematical function at time t0. Embodiments may also include displaying the rendering of the first two-dimensional treatment area in three-dimensional space for each eye of the viewer. Embodiments may also include determining a visual acuity field for each eye of the viewer in response to the displayed rendering of the first treatment area for each eye of the viewer at time t0.

In some embodiments, the computer program product may include comparing the visual acuity performance for each eye of the viewer at time t0 with a historical visual acuity performance for each eye of the viewer. Embodiments may also include updating the visual blurring function for at least one eye of the viewer if the comparison indicates a change in the visual acuity performance for the at least one eye.

In some embodiments, the updating the visual blurring function for at least one eye of the viewer if the comparison indicates a change in the visual acuity performance for the at least one eye, the change in visual acuity may include at least one of an indication of an improvement in visual acuity and a deterioration in visual acuity. Embodiments may also include displaying the number of projections for each eye of the viewer based on the received visual blurring kernel of the viewer may include dynamically altering the spatial blurring attribute for the number of projections for each eye of the viewer as a function of time.

Embodiments may also include dynamically altering the spatial blurring attribute for the number of projections for each eye of the viewer as a function of time may include altering the dimensions of the area of the spatial blurring attribute within the foveal visual acuity field of an eye of the viewer as a function of time. Embodiments may also include dynamically altering the spatial blurring attribute for the number of projections for each eye of the viewer as a function of time may include altering the dimensions of the area of the spatial blurring attribute within the foveal visual acuity field of an eye of the viewer as a sinusoidal function of time.

Embodiments may also include dynamically altering the spatial blurring attribute for the number of projections for each eye of the viewer as a function of time may include altering the dimensions of the area of the spatial blurring attribute within the foveal visual acuity field of an eye of the viewer. In some embodiments, altering the dimensions of the area of the spatial blurring attribute to maintain a cognitive load.

Embodiments may also include altering the dimensions of the area of the spatial blurring attribute to maintain a cognitive load may include inferring the cognitive load from the eye tracking information. Embodiments may also include determining a count of projections and a three-dimensional distribution of the projections for each eye of the viewer based on the eye tracking information may include determining the count of projections based at least in part on one or more of a refresh rate of the 3D-enabled digital display, a defined segment of video, a sampling rate of at least one camera of the 3D-enabled digital display, and the visual blurring function for each eye of the viewer.

Embodiments may also include receiving the visual acuity profile may include an amblyopic eye classification for each eye of the viewer. Embodiments may also include receiving a visual blurring kernel of the viewer may include receiving a contrast sensitivity function (CSF). In some embodiments, the contrast sensitivity function (CSF) may include at least one instruction for determining the spatial blurring attribute based at least in part on one or more visual acuity fields of the viewer.

Embodiments may also include at least one instruction for determining the spatial blurring attribute based at least in part on one or more visual acuity field of the viewer, the one or more visual acuity field may include at least one of a foveal visual acuity field. Embodiments may also include a parafoveal visual acuity field. Embodiments may also include a peripheral visual acuity field.

In some embodiments, the computer program product may include displaying the number of projections for each eye of the viewer based on the received visual blurring kernel of the viewer. In some embodiments, the computer program product may include determining an image attribute for the number of projections for each eye of the viewer based on the received visual blurring kernel of the viewer.

Embodiments may also include determining an image attribute for the number of projections for each eye of the viewer based on the received visual blurring kernel of the viewer may include using the eye tracking information to determine an area of interest of the 3D-enabled digital display. Embodiments may also include correlating the area of interest of the 3D-enabled digital display to the number of projections and the distribution of projections for each eye of the viewer. Embodiments may also include applying the visual blurring kernel of the viewer to an area of interest of a projected image for at least one eye of the viewer. Embodiments may also include applying the visual blurring function of the viewer to an area of interest of a projected image for the at least one eye of the viewer may include spatially-adjusting the area of interest of the projected image for the at least one eye.

BRIEF DESCRIPTION OF THE DRAWINGS

FIGS. 12A, 12B, and 13 are flowcharts illustrating methods for multi-user gaze-tracking for personalized rendering from a single 3D display, according to some embodiments of the present disclosure.

FIG. 26A is a flowchart further illustrating the method for enabling projection of images from FIG. 18, according to some embodiments of the present disclosure.

DETAILED DESCRIPTION

Embodiments of the present disclosure include multi-user gaze-tracking for personalized rendering from a single 3D display. Immersive 3D visual experiences are often calibrated to a single viewer's position for accurate projection of objects to be displayed for the viewer. It is envisioned herein that an accurate and low-latency rendering, or "fast rendering," of 3D images for multiple viewers, each presented with a perspective of that which is displayed results in a seamless viewing experience of multiple viewers of content on a single display. This is made possible through viewer-specific point-of-regard estimation via gaze tracking of each viewer, processed in parallel.

Implementations described herein provide a viewer experience that is enhanced by rendering voxels that create a perspective of a displayed object, e.g., a soccer ball, that is appropriate for the position of each viewer relative to the displayed object. According to embodiments herein, projecting multi-viewer-object 3D image perspectives from a single 3D display is achieved by acquiring eye region image data of a plurality of viewers within a field of view of at least one camera associated with a 3D-enabled digital display. Trained neural networks are then used to calculate point-of-regard for each viewer, and projections can then be calculated and rendered based on each viewer's position and point-of-regard with respect to the 3D-enabled digital display.

Figure 1:
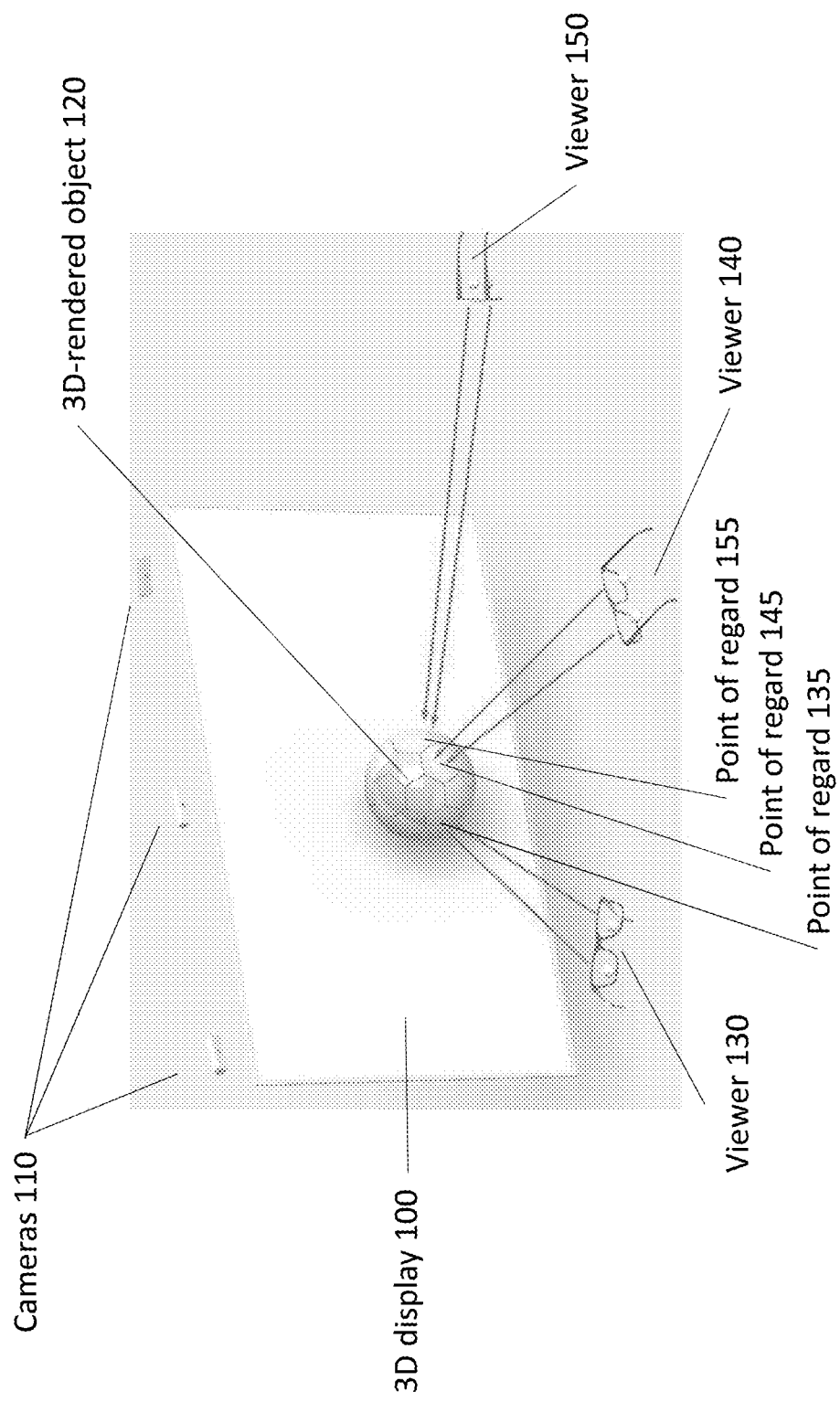
FIG. 1 depicts a system environment in which a single 3D display and associated cameras may predict gaze or point-of-regard for multiple viewers for personalized rendering of a 3D projected image of an object.

FIG. 1 depicts a system environment showing a single 3D display 100, according to some embodiments of the present disclosure. A 3D-enabled digital display, or simply a 3D display 100, refers to a display that generates three-dimensional (3D) output for a viewer, for example, one that uses lenticular lenses. The 3D display 100 may be a head-mounted display, a projection display, wide spectrum displays, digital billboards, or any other 3D display form factor.

The 3D display 100 may render output in any suitable manner that gives the viewer an impression of depth in the image(s) being viewed. For example, the 3D display 100 may render separate 2D images to the viewer's left eye and right eye, creating the illusion of depth, for example by using a lenticular lens display, parallax barriers, or other technology for glasses-free 3D displays or 3D displays requiring special glasses. In some displays, 2D images are offset and displayed separately to the viewer's left eye and right eye. The separate 2D images are combined in the viewer's brain to give the viewer the perception of depth.

Other technologies for implementing the 3D display 100 are also considered as being within the scope of the disclosure. Volumetric displays, for example, display points of light within a volume (e.g., using voxels instead of pixels). Volumetric displays may include multiple stacked planes and/or rotating display panels. Infrared laser displays focus light on a point in space, generating a plasma that emits visible light. Holographic displays implement a multi-directional backlight that enable a wide parallax angle view to display 3D images. Integral imaging displays implement an array of microlenses in front of an image and reproduces a 3D light field that exhibit parallax as the viewer moves. Compressive light field displays implement layered panels that are algorithm-driven to generate 3D content for the viewer. The 3D display 100 may implement any of these and/or a wide variety of technologies now known or later developed.

FIG. 1 shows a plurality of cameras 110 (shown above the 3D display 100), and three viewers represented in the figure by the glasses shown looking at a 3D-rendered object being displayed (the soccer ball). It is noted that based on where the viewers are located relative to the display, the cameras may receive image data at different angles and distances for the different viewers. The different cameras' fields of view may encompass the same viewer, from different angles. Accordingly, the viewers may be identified by the present system (e.g., via a digital signature or unique identifier for each viewer) and shared between the separate cameras so that the system knows when the separate cameras are viewing the same viewer.

Figure 2:
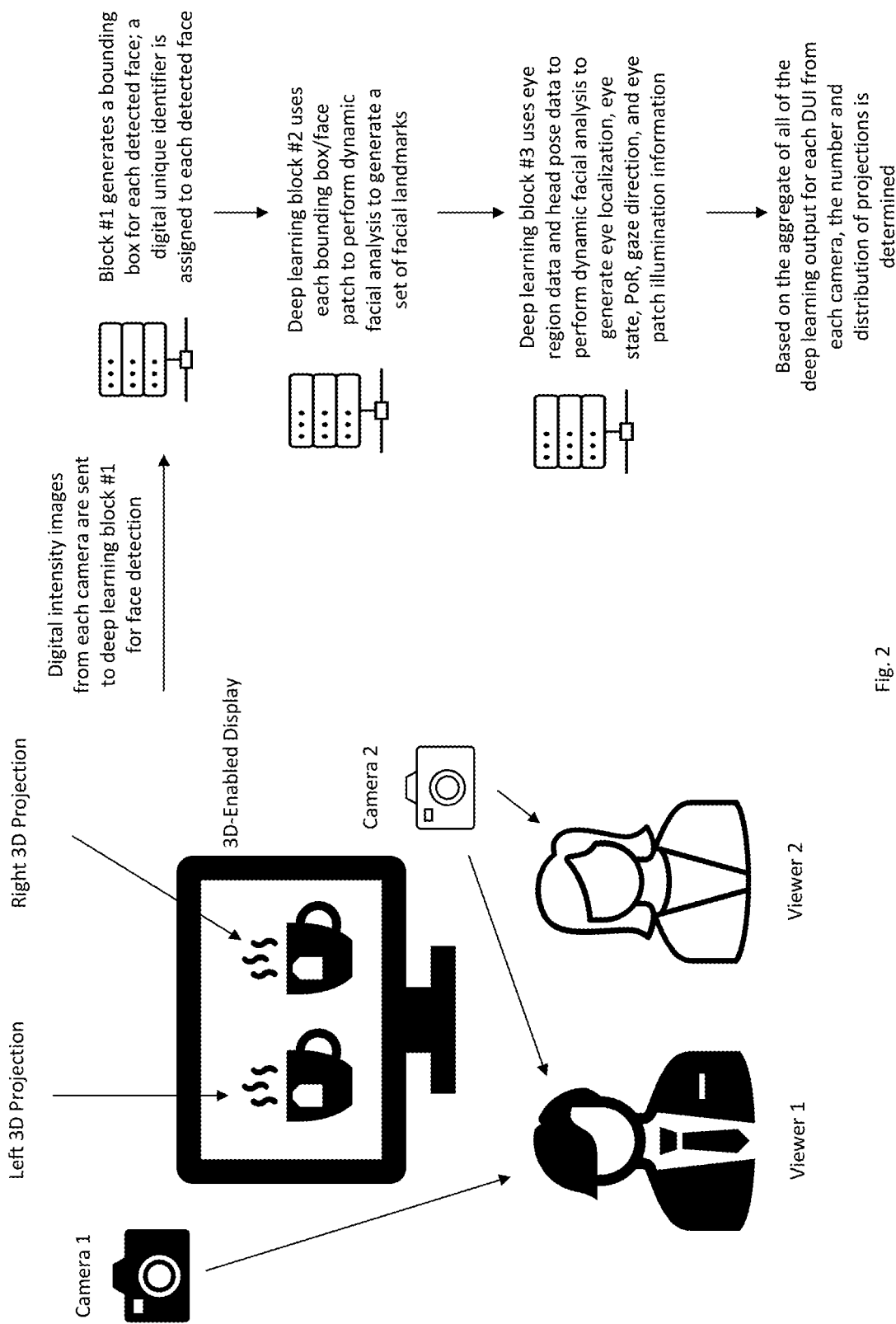
FIG. 2 depicts a high-level flow illustrating components and functions in a 3D multi-viewer gaze inferencing and object rendering system according to the instant application.

FIG. 2 depicts a system environment in which two viewers are viewing a 3D-enabled display, each viewer being analyzed for their point of regard on the display screen, and presented with 3D images appropriate to their position and gaze direction or point of regard. For example, the system may receive digital intensity images from one or more cameras in proximity to the 3D-enabled display, which may then be analyzed for face detection, position detection, and identification. Face detection may be carried out by a deep learning network as described below, e.g., a bounding box may be generated for each detected face, and a unique digital user identifier (DUI) may be assigned to each detected face as a mechanism for tracking which viewer should be shown which 3D images as their respective positions and gaze direction changes over time. The unique identifier may be associated with a viewer's face in an anonymized manner so as to not perpetuate a record of faces that would raise privacy concerns.

Position information, including distance of the viewer from the display is an important aspect of the present disclosure. The systems depicted and described in this application are uniquely suited to detecting when viewers are within the range necessary for acceptable 3D image rendering. Many systems are not equipped to make this determination, and project images to viewers in blind fashion, not knowing whether the projections will be seen by viewers as the desired 3D images, or rather as broken images due to out-of-specification distancing, inadequate viewing angle, or other positional problem with a viewer relative to the display. This wastes processing and bandwidth, resulting in increased latency and a poor user experience due to distorted, out of position, or missing 3D images.

Additional deep learning blocks use each bounding box/face patch, in the image plane, to perform facial analysis to generate a set of facial landmarks for each viewer.

Additional deep learning blocks then use eye region data and head pose data: X, Y, Z, yaw, pitch, and roll, which are the six degrees of freedom (6DOF) of the head (assumed to be a rigid body), to perform dynamic facial analysis to generate eye localization, eye state, point of regard, gaze direction, and eye patch illumination information.

Based on the aggregate of the deep learning output for each tracked viewer, from each camera, a number of 3D projections is determined, as is information about the distribution of projections for each viewer.

Figure 3:
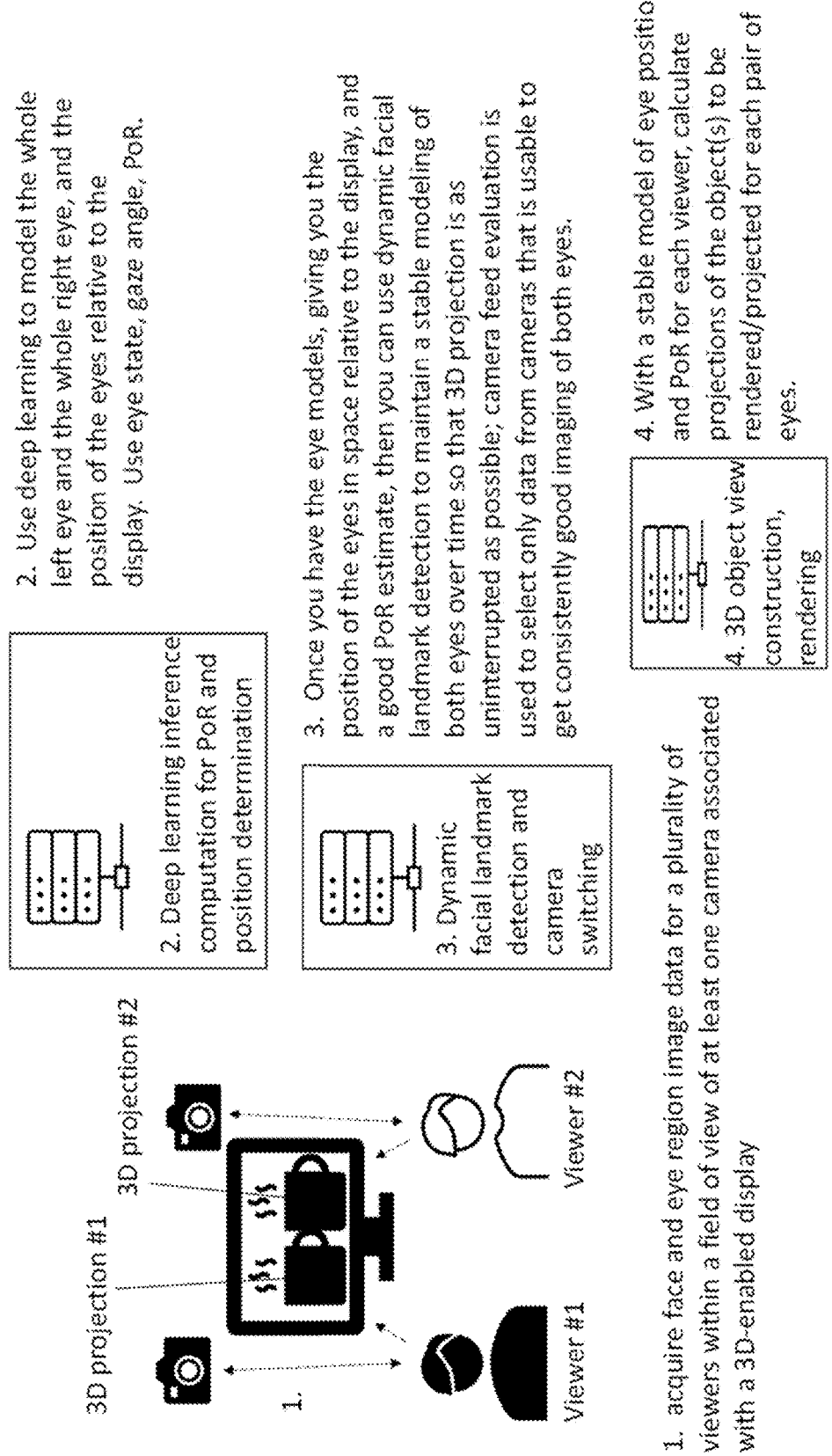
FIG. 3 depicts another high-level flow illustrating components and functions in a 3D multi-viewer gaze inferencing and object rendering system according to the instant application.

FIG. 3 also depicts a system environment in which two viewers are viewing a 3D-enabled display, each viewer being presented with a personalized 3D projection, e.g., 3D projection #1 for viewer #1, and 3D projection #2 for viewer #2. As an initial operation, the system may acquire face and eye region image data for a plurality of viewers within a field of view of at least one camera associated with a 3D-enabled display. As described above, positional information including distance from the viewer to the display screen and viewer angle relative to the plane or curve of the display screen may be evaluated in order to make a decision to render 3D images for specific viewers, or not. If position analysis indicates that the viewer is too far away for accurate gaze tracking analysis, and therefore too far away for the system to position the 3D projection appropriately for the viewer, then the system may default to a 2D image rather than project a poor quality or broken 3D image. Similar determinations may be made if viewing angle changes make it impossible for the viewer to see 3D images properly.

Returning to FIG. 3, the system may use deep learning to model the whole left eye and whole right eye, as well as the position of the eyes relative to the display, and eye state, gaze angle, and point of regard.

Once these models are built for each viewer, giving position of the eyes in space relative to the display, and a good point of regard estimate, dynamic facial landmark detection is used to maintain a stable modeling of both eyes over time so that 3D projections are as uninterrupted as possible. This also permits a novel and desirable switching between 3D and 2D image presentation, so that the user does not experience broken or missing 3D projections when not positioned appropriately to view them.

Importantly, camera image feed evaluation can be done at one or more stages in this process so that only camera image data that is usable to get consistently good imaging of both eyes of each viewer is selected. This conserves processing resources and bandwidth in situations in which, for example, an obstruction or lack of light makes the images from a given camera unusable in informing the deep learning systems in order to calculate viewer position, facial landmark, gaze direction, point of regard, or other parameter.

With a stable model of eye position and point of regard for each viewer, the system may then calculate 3D projections of the object(s) to be rendered for each pair of eyes, for each viewer.

Figure 4:
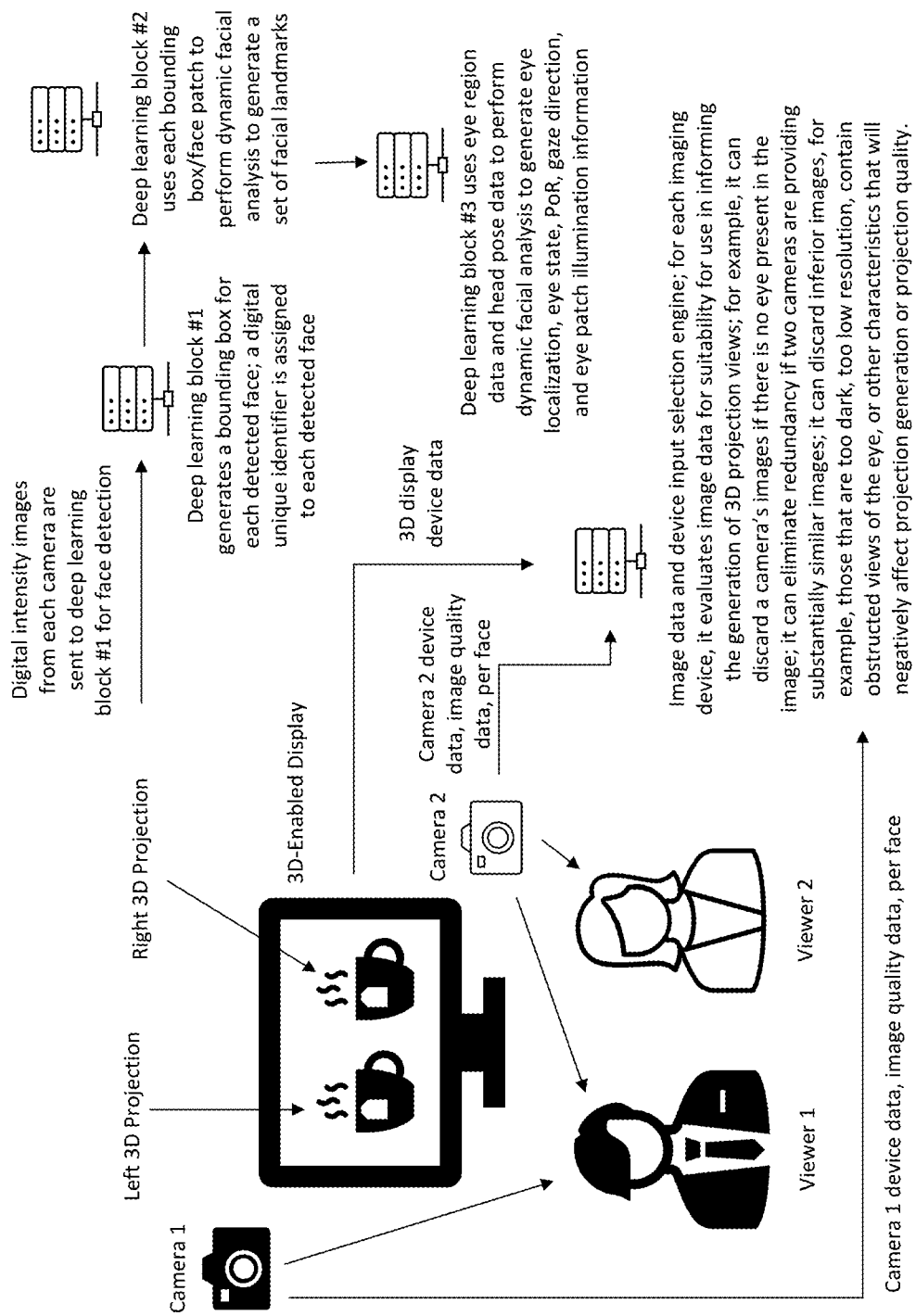
FIG. 4 depicts yet another high-level flow illustrating components and functions in a 3D multi-viewer gaze inferencing and object rendering system according to the instant application.

FIG. 4 also depicts a system environment in which two viewers are viewing a 3D-enabled display, each viewer being presented with a personalized 3D projection. Here, in addition to the deep learning blocks that perform face detection, facial landmark detection, eye localization, eye state, point of regard, gaze direction, and eye patch illumination information, image data from each active camera associated with the 3D enabled display may be analyzed by an image data and device input selection engine. This is an evaluation of image data from each imager, in which each image feed is evaluated for its suitability in informing the generation of 3D projections for each viewer. For example, this system may discard a camera's image data if there is no eye present in the images, saving processor cycles accordingly. The system may also eliminate redundancy in image data if two cameras are providing substantially similar images, and it can discard inferior image data. For example, images that are too dark, that are of too low resolution, which contain obstructed views of the eye, or other characteristics that will negatively affect projection generation or projection quality.

Figure 5:
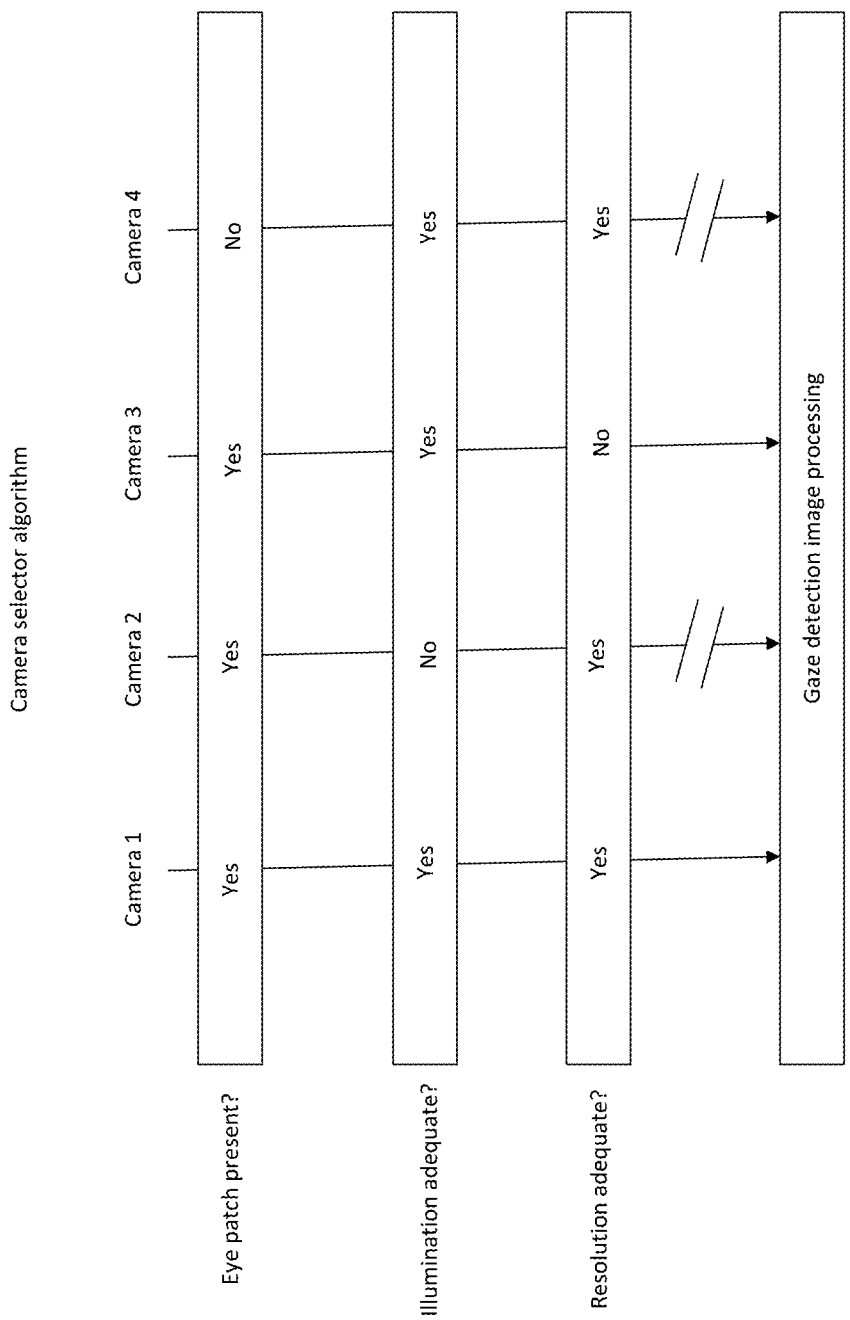
FIG. 5 depicts a set of algorithms for evaluating camera image data according to the present disclosure.

FIG. 5 depicts a camera selector algorithm for four different camera feeds. The algorithm is programmed to evaluate the presence of an eye patch in image data from each camera, illumination level, and resolution. Evaluation may consider binary conditions, a range of values, or threshold values. For example, binary conditions indicating the presence of an eye patch, adequate illumination, and adequate resolution may result in acceptance of the image data from camera 1 for further processing in informing face and gaze tracking for 3D projection rendering. However, if important parameters are missing or are at sub-threshold levels, the image data may be blocked from further processing (see cameras 2 and 4). In some cases, however, a failure of one parameter may still result in overall use of the image data for further processing. For example, camera 3 image data has an eye patch, adequate illumination, but lower than desired resolution. This image data may still be acceptable and passed through for further processing.

Figure 6:
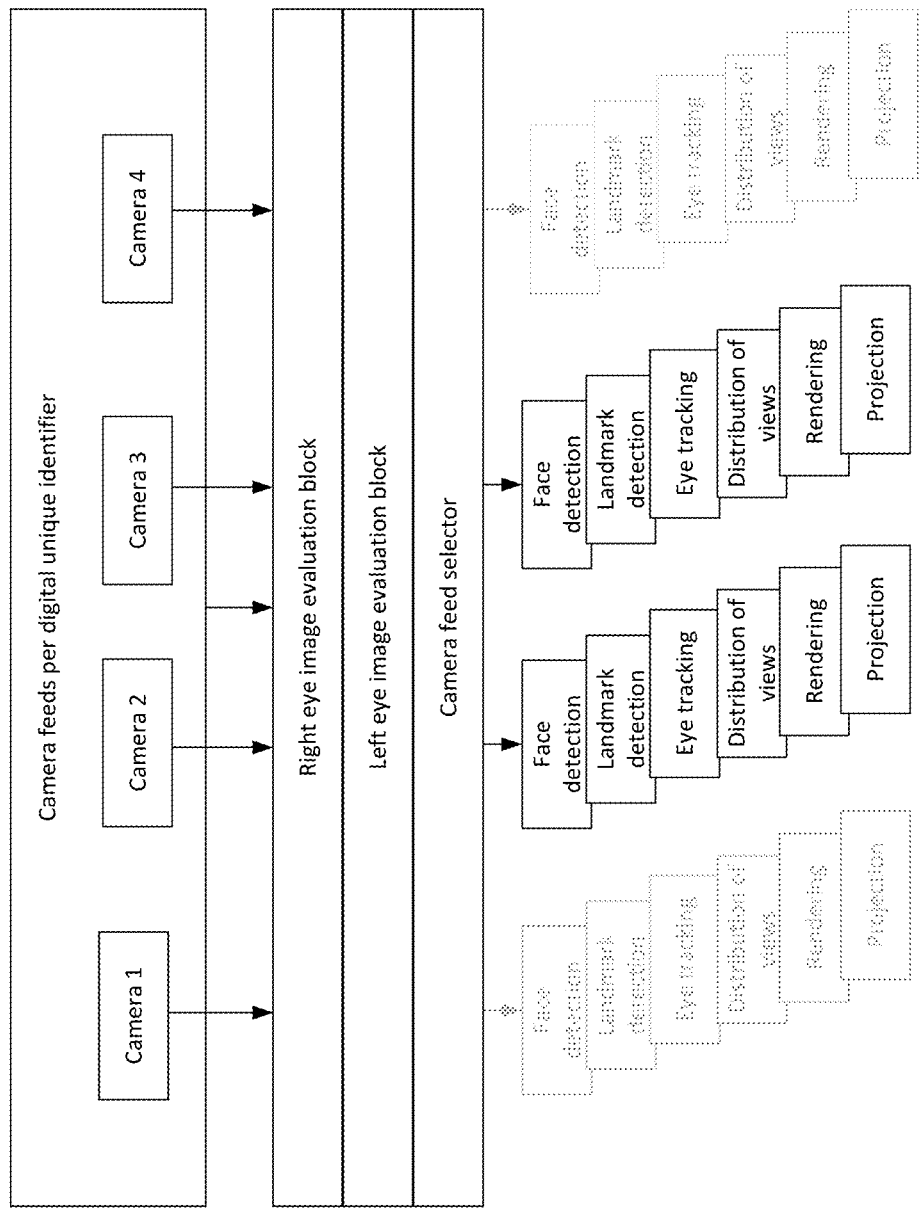
FIG. 6 also depicts a set of algorithms for evaluating camera image data according to the present disclosure.

FIG. 6 depicts an alternate view of a camera selector algorithm for four different camera feeds. In this example, camera feeds that meet minimum requirements for use as described in FIG. 5 above, may be passed through evaluation blocks for each eye, left and right, for each viewer. As shown in FIG. 6, the image feeds from cameras 2 and 3 are good enough to proceed through the additional processing operations of face detection, facial landmark detection, eye tracking, distribution of projection calculations, rendering of 3D images, and display projection. Thus, the evaluation and selection of image feeds potentially avoids large amounts of wasted processing when poor images are being captured of the viewer(s).

Additional parameters that the camera selector algorithm can evaluate include viewer distance and angle relative to the display screen. If a viewer exceeds the minimum acceptable distance to the display, or if the viewer moves to an angle such that they will no longer see projected 3D images in three dimensions, the camera selector algorithm may block those image feeds and, in the absence of adequate image data to inform 3D projections, signal a switch to a default 2D projection so that the system does not project broken or unviewable 3D images. This will in many cases rescue a viewing experience, which can be unsettling when 3D images disappear or become distorted.

Figure 7:
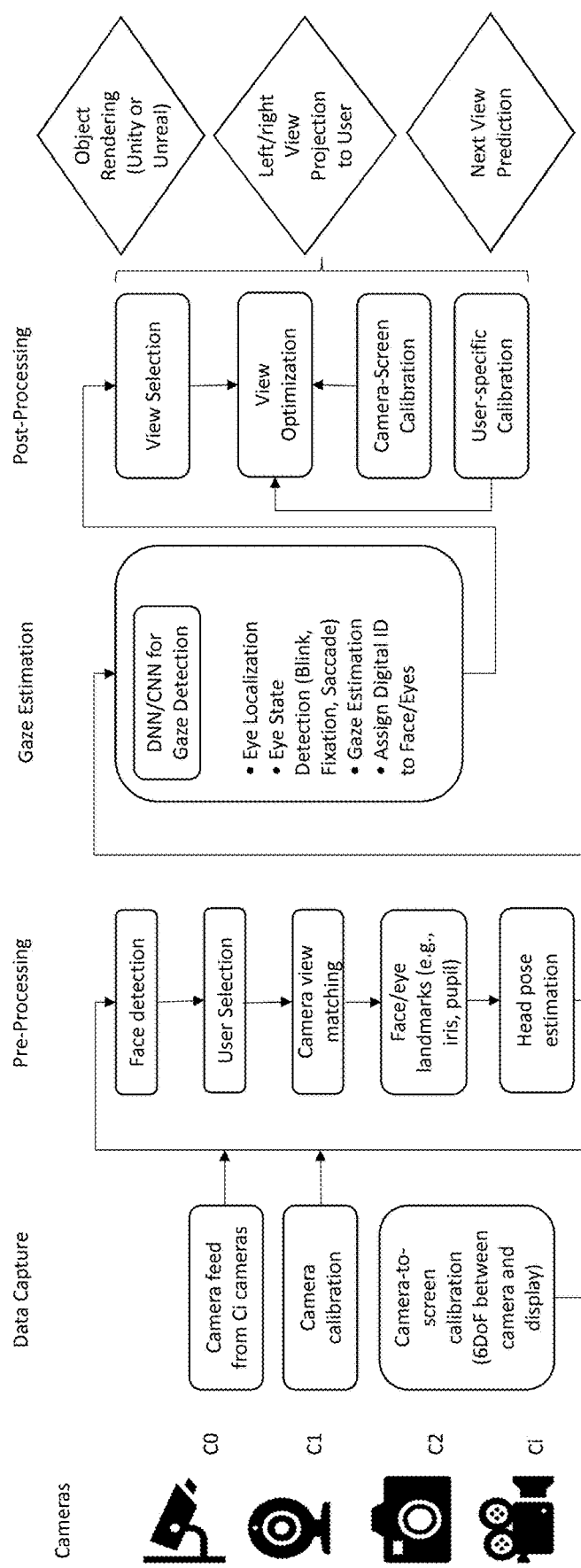
FIG. 7 depicts a high-level block diagram illustrating a multi-user gaze or PoR estimation and 3d rendering inference flow.

FIG. 7 is a high-level block diagram illustrating an example of a multi-user gaze or PoR estimation and 3D rendering inference flow according to the instant application. In this example, multiple cameras may capture viewer image data, e.g., camera C0, camera C1, camera C2, or camera Ci. Example data capture may include, but is not limited to camera feeds, camera calibration, and screen calibration. The term "screen calibration," as used herein, refers to calibrating the cameras relative to the display. In an example, the data may be pre-processed via face detection of multiple users, user selection, camera view matching (e.g., which camera works best for a particular viewer and/or timeframe), face/eye landmarks (e.g., iris or pupil), and head pose estimation. In an example, the number of supported users may be determined as a parameter to the system and may be based at least in part on the number of cameras in the system. In an example, camera view matching helps ensure that only the minimum number of cameras needed for a number of viewers are activated, to reduce data transmission bandwidth requirements, and to reduce computation necessary to process the data.

A deep gaze unit may be implemented to determine eye localization, eye state detection (e.g., blinks, eye movements, or eye fixations), gaze estimation, and assigning a digital ID to the face/eyes of each viewer. In an example, face identification may accommodate situations in which a viewer's face is obstructed (e.g., if a viewer is wearing a mask or is wearing glasses).

Post-processing may include view selection, view optimization, camera-screen calibration, and user-specific calibration. View optimization may be based on parameters from neural networks such as DNNs or CNNs for gaze detection, or from user-specific calibration.

The display may be configured for object rendering, left/right view projection to the user, and next view estimation. In an example, a view optimizer may be implemented to refresh only those pixels where the user is fixating her gaze, and not the full object. This may save computing in terms of projection calculation and rendering, with attendant benefits to resolution (e.g., more pixels can be used to render the area of focus to give a high resolution of that focal area of the projected content). In an example, the next view prediction involves the rendering engine preparing a 3D object or portion of a 3D object ahead of time, to be cached for later projection and viewing.

Figure 8:
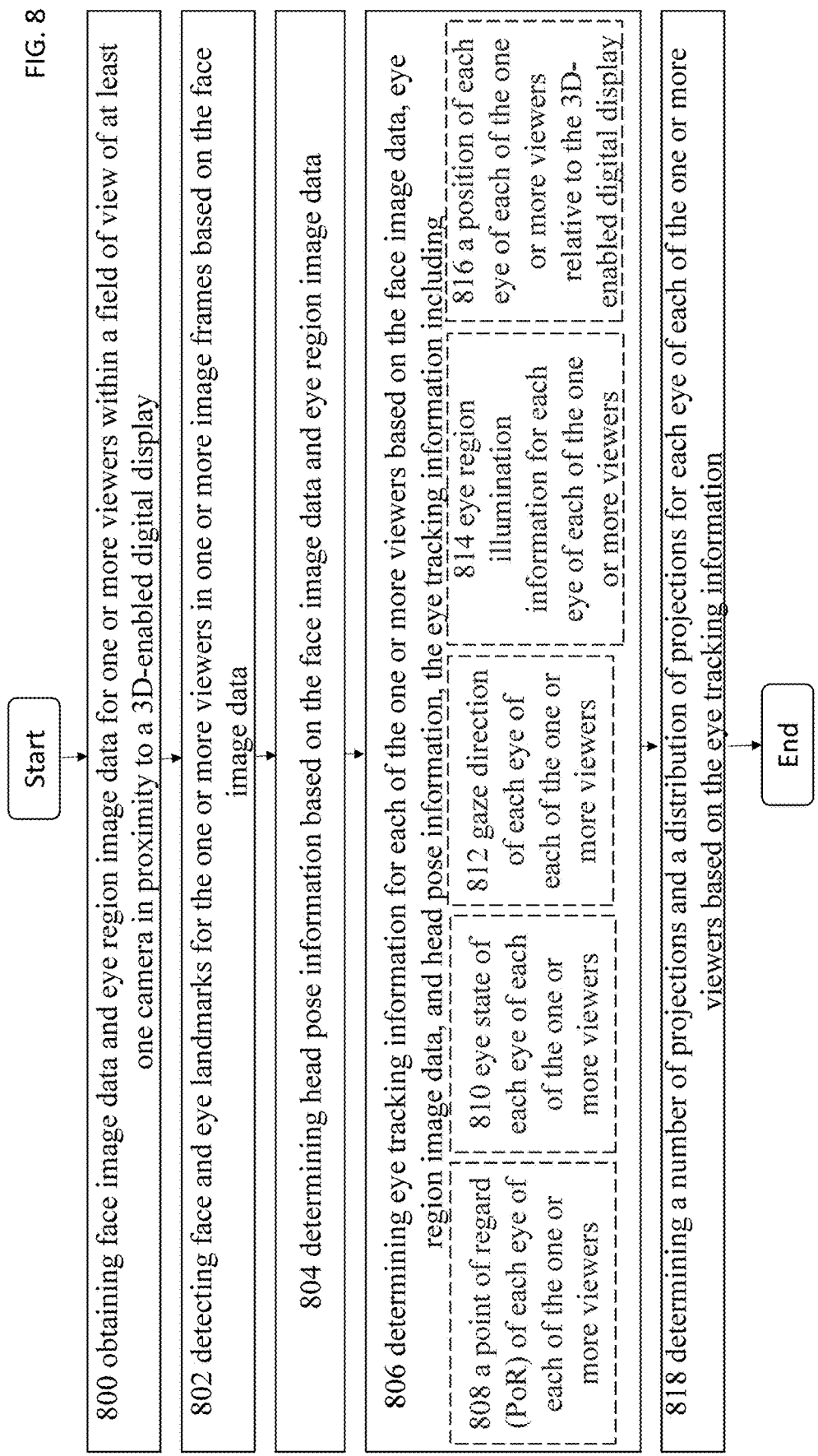
FIGS. 8-10 are flowcharts illustrating method for projecting multi-viewer-specific 3D object perspectives, according to some embodiments of the present disclosure.

FIG. 8 is a flowchart that shows a method for projecting multi-viewer-specific 3D object perspectives, according to some embodiments of the present disclosure. At 800, the method may include obtaining face image data and eye region image data for one or more viewers within a field of view of at least one camera in proximity to a 3D-enabled digital display. The camera may be integrated into with the 3D display or provided separately. More than one camera may be implemented, for example, to combine input data from multiple vantage points. At 802, the method may include detecting face and eye landmarks for the one or more viewers in one or more image frames based on the face image data. In some embodiments, the eye region image data may include at least one of pupil image data, iris image data, or eyeball image data.

By way of illustration, the 3D eye position may include the distance of the viewer's eye from the 3D display, or the location of the viewer's eye ball(s) in an x, y, z coordinate reference grid including the 3D display. Accordingly, the 3D eye position may refer to the position of one or more viewer's eyes in space, for example based on the viewer's height. Gaze angle may vary based on whether the viewer is looking up, down, or sideways. Both 3D eye position and gaze angle may depend at least in part on the viewer's physical characteristics (e.g., height), physical position (e.g., standing or sitting), and head position (which may change with movement).

Point-of-regard refers to a point on the display that the viewer's eye(s) are focused on, for example, the position of rendered content being viewed by the viewer's eyes at a given point in time. Point-of-regard may be determined based on gaze tracking, the position of content being rendered, focus of the content, and viewer selection.

In some embodiments, the at least one gaze angle comprises yaw and pitch. Yaw refers to movement around a vertical axis. Pitch refers to movement around the transverse or lateral axis. In some embodiments, the analyzing the eye region image data further comprises analyzing at least one eye state characteristic. In some embodiments, the eye state characteristic comprises at least one of a blink, an open state being either a fixation or a saccade (movement), or a closed state. The open state refers to an eye being fully open or at least partially open, such that the viewer is receiving visual data. The closed state refers to fully closed or mostly closed, such that the viewer is not receiving significant visual data. In some embodiments, the acquiring eye region image data may be performed by a camera at a distance of at least 0.2 meters from the plurality of viewers. It is noted, however, that the viewer(s) may be located at any suitable distance.

In some embodiments, the acquiring eye region image data may be performed by at least one of a laptop camera, tablet camera, a smartphone camera, a digital billboard camera, or a digital external camera. In some embodiments, the acquiring eye region image data may be performed with active illumination. In some embodiments, the acquiring eye region image data may be performed without active illumination. In some embodiments, the analyzing the eye region image data to determine at least one 3D eye position, at least one gaze angle, and at least one point-of-regard for at least one viewer relative to at least one camera associated with the 3D-enabled digital display may include mapping the eye region image data to a Cartesian coordinate system and unprojecting the pupil and limbus of both eyeballs.

At 804, the method may include determining head pose information based on the face image data and eye region image data.

At 806, the method may include determining eye tracking information for each of the one or more viewers based on the face image data, eye region image data, and head pose information, the eye tracking information including a point of regard (PoR) of each eye of each of the one or more viewers, eye state of each eye of each of the one or more viewers, gaze direction of each eye of each of the one or more viewers, eye region illumination information for each eye of each of the one or more viewers, and a position of each eye of each of the one or more viewers relative to the 3D-enabled digital display.

In some embodiments, the eye region image data may be mapped to a Cartesian coordinate system. The Cartesian coordinate system may be defined according to any suitable parameters, and may include for example, a viewer plane with unique pairs of numerical coordinates defining distance(s) from the viewer to the image plane. In some embodiments, the method may include unprojecting the pupil and limbus of both eyeballs into the Cartesian coordinate system to give 3D contours of each eyeball. Unprojecting refers to defining 2D coordinates to a plane in a 3D space with perspective. In an example, a 3D scene may be uniformly scaled, and then plane may be rotated around an axis and a view matrix computed.

At 818, the method may include determining a number of projections and a distribution of projections for each eye of each of the one or more viewers based on the eye tracking information. In some embodiments, at least one of the plurality of projections may be calculated to be appropriate for each respective viewer's position and point-of-regard relative to the 3D-enabled digital display.

In some embodiments, the method may include detecting degradation in the eye region image data. For example, a viewer may move or turn at an angle to the camera, reducing the quality of image data captured by a particular camera. In some embodiments, the method may include switching to a different camera based on the degradation in the eye region image data. For example, another camera may have a better view of the viewer as the viewer turns his or her head or walks toward or away from the camera.

In some embodiments, the method may include analyzing the eye region image data for at least one of engagement with the 3D-enabled digital display, fixation, or saccade. For example, a viewer may be engaged with the content on the display, or the viewer may be disengaged (e.g., looking toward the display without engaging with the content). The viewer may become fatigued, for example, by having looked at the content for too long a time, or otherwise being tired. The viewer may also not be paying attention to the content (e.g., if the user is distracted by a loud noise, a phone ringing, someone talking nearby, etc.). In some embodiments, the method may include assigning a unique digital identifier to each face for each viewer among the one or more viewers. In some embodiments, the identifier may be associated with at least one sequence of image projections calculated for each viewer. The identifier may be any suitable sequence of numbers and/or characters and/or other data to identify, differentiate, or otherwise track the viewer.

In some embodiments, the method may include acquiring eye region image data of a plurality of viewers within a field of view of at least one camera associated with a 3D-enabled digital display. The field of view may be defined in two-dimensional or three-dimensional space, such as from side-to-side, top-to-bottom, and far or near. The method may include analyzing the eye region image data to determine at least one 3D eye position, at least one gaze angle, and at least one point-of-regard for at least one viewer relative to at least one camera associated with the 3D-enabled digital display, from which to estimate gaze direction or PoR. Input from more than one source (e.g., multiple cameras) may be received. In some embodiments, the method may include analyzing the eye region image data for at least one of engagement with the 3D-enabled digital display, fixation, or saccade. In some embodiments, the method may include assigning an identifier to each face, one for each respective viewer. This operation may occur at any point in the method, but preferably before or near the time that eye region image data for each viewer is acquired, so that the eye region image data for each viewer may be associated with that viewer's identifier in order to personalize the projection rendering for each specific viewer.

In some embodiments, the method may include calculating a plurality of image projections for display by the single 3D display. Image projections refer to the rendered and presented result of mapping display image data to pixels or other output of a 3D display to create a viewable 3D image or series of images. In some embodiments, at least one of the plurality of projections may be calculated to be appropriate for each viewer's position and point-of-regard with respect to the 3D-enabled digital display. Different projections may be calculated for different viewers. Viewers may also be prioritized. For example, personalized projections for viewers engaged with or otherwise paying attention may be prioritized over projections for viewers who are farther away or not engaged with the display. In some embodiments, the eye region image data comprises at least one of pupil image data, iris image data, or eyeball image data.

In some embodiments, the at least one gaze angle comprises yaw and pitch. Yaw and pitch may change as the viewer moves their eye, their head, or their position (e.g., moving side-to-side or toward or away from a camera or display). In some embodiments, the analyzing the eye region image data further comprises analyzing at least one eye state characteristic. In some embodiments, the eye state characteristic comprises at least one of a blink, an open state being either fixation or saccade, or a closed state. Blink may be defined by a threshold. For example, the eye state characteristic may ignore routine eye blinks, but trigger on multiple and/or slow eye blinks. In some embodiments, the acquiring eye region image data may be performed by a camera at a distance of at least 0.2 meters from at least one of the plurality of viewers.

In some embodiments, the acquiring eye region image data may be performed by at least one of a laptop camera, a tablet camera, a smartphone camera, a digital billboard camera, or a digital external camera. In some embodiments, the acquiring eye region image data may be performed with active illumination. In some embodiments, the acquiring eye region image data may be performed without active illumination.

Figure 9:
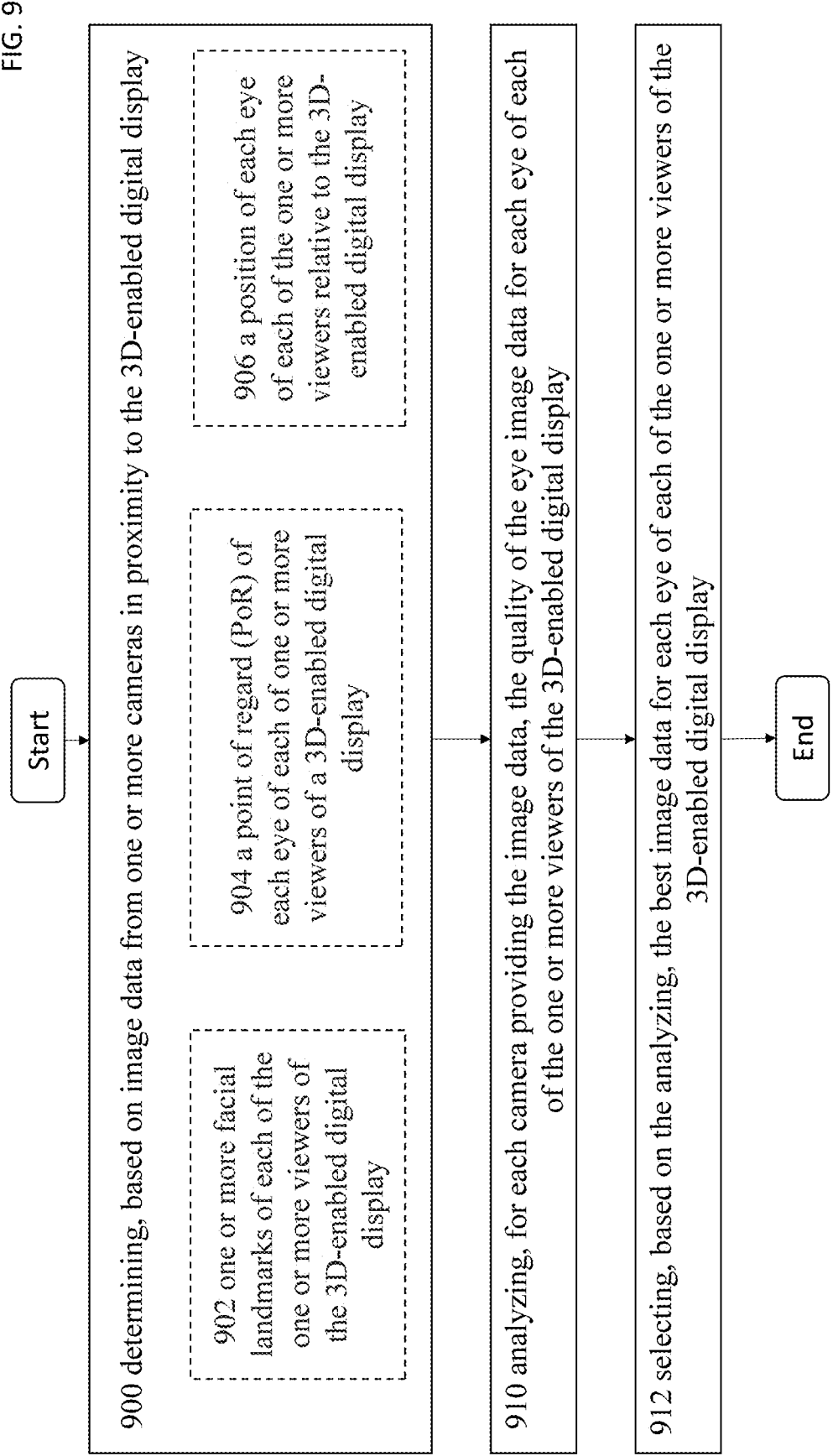

FIG. 9 is a flowchart that shows a method for selecting image data to be used in 3D image projection, according to some embodiments of the present disclosure. At 900, the method may include determining, based on image data from one or more cameras in proximity to the 3D-enabled digital display a) one or more facial landmarks of each of the one or more viewers of the 3D-enabled digital display 902; b) a point of regard (PoR) of each eye of each of one or more viewers of a 3D-enabled digital display 904; and c) a position of each eye of each of the one or more viewers relative to the 3D-enabled digital display 906.

At operation 910, the method may include analyzing, for each camera providing the image data, the quality of the eye image data for each eye of each of the one or more viewers of the 3D-enabled digital display.

At operation 912, the method may include selecting, based on the analyzing, image data for each eye of each of the one or more viewers of the 3D-enabled digital display.

Figure 10:
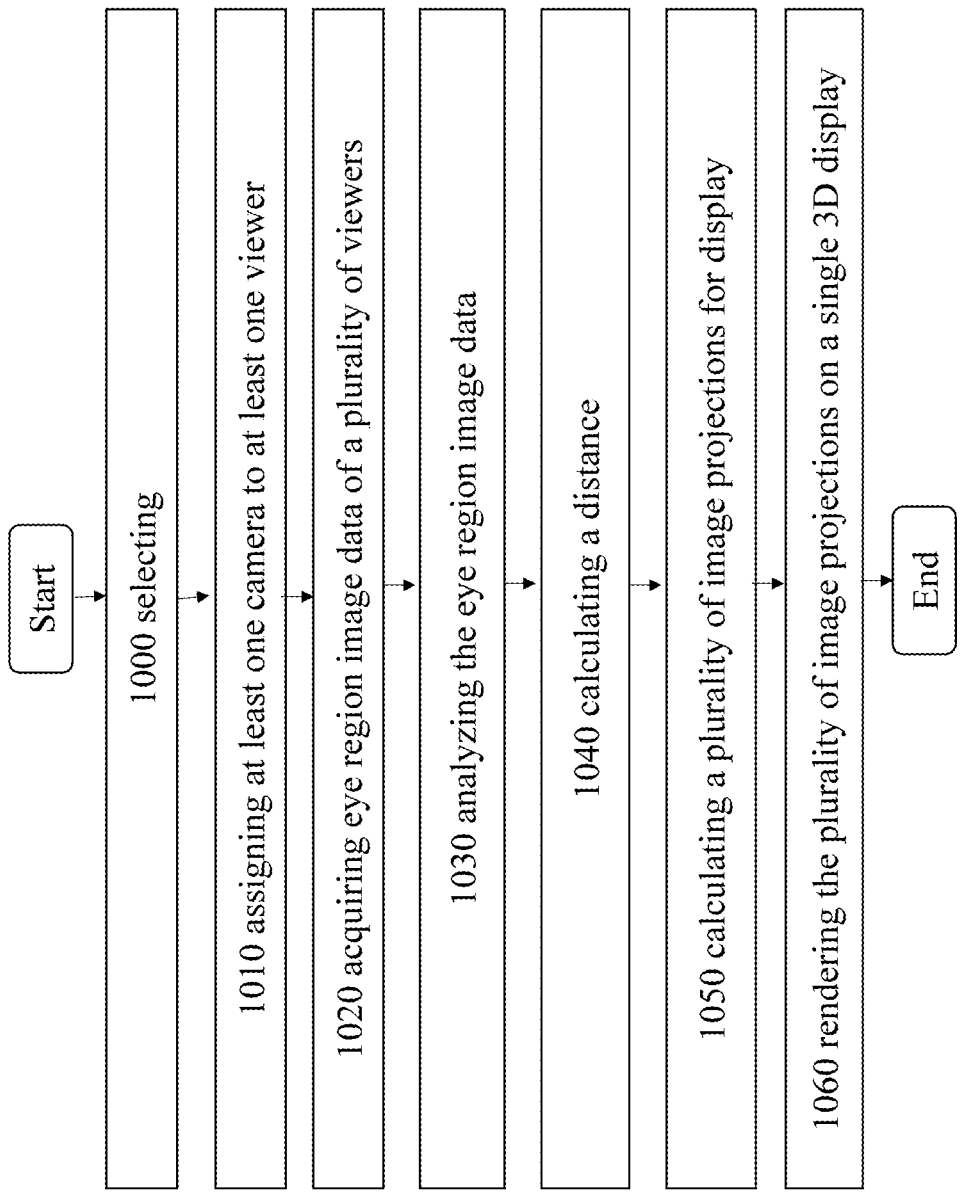

FIG. 10 is a flowchart that shows a method for projecting multi-viewer-specific 3D object perspectives, according to some embodiments of the present disclosure. At 1000, the method may include selecting at least two viewers based on at least one property of a 3D display (e.g., resolution, size, single camera or multi-camera scenario) or at least one eye property of the at least two viewers. Properties of the viewer may include, but are not limited to, the position of the viewer, physical characteristic(s) of the viewer, or viewer action or reaction (e.g., engagement). At 1010, the method may include assigning at least one camera to at least one viewer based on an assessment of which camera among a plurality of cameras has the best viewing angle and imaging conditions of an eye region of at least one viewer. In an example, the term "best" may be relative to viewing conditions of other cameras having a specific user/viewer in the field of view. For example, the term "best" may be between two or more cameras or users/viewers present at the moment. In another example, the term "best" may refer to a predetermined standard of comparison, in which case there may not be any cameras that meet the standard at times, i.e., no camera is able to image a user/viewer well.

At 1020, the method may include acquiring eye region image data of a plurality of viewers within a field of view of at least one camera associated with a 3D-enabled digital display. At 1030, the method may include analyzing the eye region image data to determine at least one 3D eye position, at least one gaze angle, at least one point-of-regard, and at least one eye state for at least one viewer relative to at least one camera or display region associated with the 3D-enabled digital display.

At 1040, the method may include calculating a distance between at least one camera and at least one viewer using image analysis (See, e.g., K. A. Rahman, M. S. Hossain, M. A. -A. Bhuiyan, T. Zhang, M. Hasanuzzaman and H. Ueno, "Person to Camera Distance Measurement Based on Eye-Distance," 2009 Third International Conference on Multimedia and Ubiquitous Engineering, 2009, pp. 137-141, doi: 10.1109/MUE.2009.34; https://ieeexplore.ieee.org/document/5319035.

At 1050, the method may include calculating a plurality of image projections for display by the single 3D display. In some embodiments, at least one of the plurality of projections may be calculated to be appropriate for each viewer's position and point-of-regard with respect to the 3D-enabled digital display. For example, projections for viewers that are closer and/or engaged with the display may receive priority over projections for viewers who are farther away and/or are not engaged. At 1060, the method may include rendering the plurality of image projections for respective viewers on the single 3D display.

Facial Landmark Detection

In some embodiments, facial landmark analysis may be performed, for example to distinguish one viewer from another for the purpose of assigning unique identifiers to each viewer of a single display. Face data for analysis by the facial landmark detector may be obtained from any suitable source, as described above, such as images in a proprietary dataset or other image database. In one example, a facial landmark detector may perform farthest point sampling of the data for each session while using head rotation as the feature to sample. Data may include some variety of head poses, although most recordings use a frontal head pose. Data may also include faces from a wide variety of people. The dataset should include good image quality, a wide variety of head poses, a wide variety of people, and a wide variety of facial expressions.

An example data preparation process includes generating a ground truth by using a pre-trained landmark detector. Data preparation may also include generating emotion classification by using a pre-trained emotion recognition algorithm. Data preparation may also include computing a head pose using the detected landmarks.

In another example, the data may be filtered in such a way that only the images with "interesting" facial expressions are kept. The term "interesting" facial expressions as used in this context may include distinct expressions, common expressions, unusual expressions, or other category of expression depending on the desired output.

For each frame, the facial landmark detector may compute additional frames. For example, frames may be computed where the face bounding box is slightly moved in a random direction, in order to prevent the model from being limited to facial landmarks that are in the middle of a frame. Some frames that are sampled from the data may not have any faces in them. These frames may be used as negative examples to help the neural network understand the absence of a face.

As part of the training process, the facial landmark detector may use different data augmentation techniques. Example techniques may include random zoom in/out. This increases the model's ability to predict different face bounding box borders. Example techniques may also include random rotation. This increases the model's ability to predict different head poses. Example techniques may also include random translation. This also increases the model's ability to predict different head poses. Example techniques may also include impulse noise. This increases the model performance on noisy data. Example techniques may also include random illumination. This technique can be used to add an illumination effect to the image. Example techniques may also include a random black box as an obstruction or occlusion. This technique increases the model's ability to deal with occlusions.

In one example embodiment of the facial landmark detector model, the input to the model is a 192×192 single-channel image. The image includes a face. An output is generated with N×2, where N is the number of landmarks the model outputs. For each landmark, the facial landmark detector model predicts its X,Y location in the input frame. The output is normalized between 0 and 1. A binary classifier predicts whether there is a face in the input frame, and outputs a score between 0 and 1.

FIGS. 14-17 show example landmark generation and flows according to the methods described herein.

The model architecture may include a common backbone that receives the image as input and produces an embedding of it. Landmarks may be split into different groups that share some similarities. Each head is fed by the common embedding, and outputs some subset of the landmarks. Each computed head has its own computation graph. Groups may include, for example, eyes, mouth, and exterior of the face. Using the groups helps the model to perform independent prediction of different facial landmark groups. These groups help the model to avoid biasing, do symmetry prediction, and compute some landmarks even though other landmarks are occluded. For example, the model works well on face images with masks, although the model never saw masks in the training process.

In some embodiments, the loss function is a variant of Adaptive wing loss, but in some embodiments, the theta changes linearity during the training so the model is punished more on small errors as the training progresses. See Adaptive Wing Loss for Robust Face Alignment via Heatmap Regression; Xinyao Wang, Liefeng Bo, Li Fuxin; arXiv:1904.07399; https://arxiv.org/abs/1904.07399; https://dio.org/10.48550/arXiv.194.07399; hereby incorporated by reference.

In an example, the failure rate of images can be determined based on the normalized mean error (NME) being larger than some value (e.g., 0.1). Frames with large NME are considered to be frames on which the prediction failed.

Gaze Estimation Methods and Systems Using Deep Learning

As described in U.S. patent application Ser. No. 17/298,935 titled "SYSTEMS AND METHODS FOR ANATOMY-CONSTRAINED GAZE ESTIMATION," incorporated by reference herein, real-time methods and systems using non-specialty cameras are disclosed for providing a point-of-regard (PoR) in a 3D space and/or 2D plane, based on user-personalized constrained oculometry (identified for each eye).

This is achieved, partly, through deep-learning-based, landmark detection of iris and pupil contours on recorded images obtained by the imaging module comprising an optical sensor that is directed toward the user, as well as deep-learning-based algorithm for estimating user's head pose with six (6) degrees of freedom (DOF), namely localization in 3D space (x, y, z) and angular positioning (pitch, yaw, roll)). Additionally, geometrical and ray tracing methods can be employed to unproject the iris and pupil contours from the optic sensors in the imaging module's plane onto 3D space, thus, allowing the system to estimate the personalized, user-specific eye (used interchangeably with "eyeball") location (based on an initial geometry eyeball-face model, that relates between visible feature such as facial-landmarks to non-visible features such as eyeball center, refraction index, corneal-eyeball deviation, etc.) and gaze direction in the imaging module's space (e.g., Cartesian) coordinate system (in other words, a system of representing points in a space of given dimensions by coordinates). Likewise, the term "Cartesian coordinate system" denotes a system where each point in a 3D space may be identified by a trio of x, y, and z coordinates. These x, y, and z coordinates are the distances to fixed X, Y and Z axes. In the context of the implementations disclosed, the 3D coordinate system refers to both the 3D position (x, y, z) and 3D orientation (pitch, roll, yaw) of the model coordinate system relative to the camera coordinate system.

The components used for the operation of the system can be, for example, an imaging module with a single optical (e.g., passive) sensor having known distortion and intrinsic properties, obtained for example, through a process of calibration. These distortion and intrinsic properties are, for example, modulation-transfer function (MTF), focal-length for both axes, pixel-size and pixel fill factor (fraction of the optic sensor's pixel area that collects light that can be converted to current), lens distortion (e.g., pincushion distortion, barrel distortion), sensor distortion (e.g., pixel-to-pixel on the chip), anisotropic modulation transfer functions, space-variant impulse response(s) due to discrete sensor elements and insufficient optical low-pass filtering, horizontal line jitter and scaling factors due to mismatch of sensor-shift- and analog-to-digital-conversion-clock (e.g., digitizer sampling), noise, and their combination. In an exemplary implementation, determining these distortion and intrinsic properties is used to establish an accurate sensor model, which can be used for calibration algorithm to be implemented.

As part of the analysis of the recorded image, the left or right eye region of the user can be defined as the region encompassing the corners of the eye as well as the upper and lower eyelids, having a minimal size of 100×100 pixels, in other words, each of the left, and right eyes' region comprises a quadrilateral polygon (e.g., a rectangle) of at least 100 pixels by 100 pixels extending between the corners of each eye as well as between the upper and lower eyelids, when the eye is open.

To build an accurate eye model, the locations of the iris of both eyes is established in a 3D coordinate system in which the eyeball center is fixed. The head pose coordinate system can serve as the basis for establishing the iris location. In an example, an eye-face model—the location of both eyeball centers is determined in head coordinates (with regard to facial landmarks). An example of a pseudo code for the algorithm of the eye-model building is:
Eye Face Model Building Example:

---

Input:
- ○ $\{F\}_{i=1 \ldots N}$—N Image Frames
- ○ C—Camera's intrinsics, projection matrix and distortion coefficients
- ○ K—Camera Matrix Output
- ○ $E_L$, $E_R$—Left and Right Eyeball centers
- ○ $IE_L$, $IE_R$-iris—Eye center offsets Algorithm:
- ○ 1. For each Frame, F
  - ■ a. ←IntrinsicDistortionCorrection($F_i$, C)
    - ■ Was done by multiplying with a camera projection matrix in order to bring the data to a similar form to what the network knows how to handle.
  - ■ b. $\{LP\}_{j,eye}$, $R_H$, $T_H$, Landmarks$_i$←HeadposeLandmarkIrisDetection($\{\text{tilde over }(F)\}_i$)
    - ■ Was done by deep neural networks. $R_H$, $T_H$ denote head rotation and translation respectively.
  - ■ c. For each eye:
    - ■ i. ProjectedIrisEllipse(a,b,φ,$x_c$,$y_c$)←EllipseFitting($\{LP\}_{j,eye}$)
  - ■ The iris was estimated as a circle mapped to an ellipse by the camera's projection:
    - ■ ii. IrisConeccs←Unproject(ProjectedIrisEllipse, K) (307a)— Produces a cone in Camera's Coordinate System which is the result of multiplying the projected ellipse points with the inverse of the camera projection matrix (each point is mapped to a line in 3D).
    - ■ iii. IrisCone$_{HCS}$←ApplyRotationTranslation($R_H$, $T_H$, IrisCone$_{CCS}$)
      This stage was done to bring the cone (and by extension the Iris circle) to a coordinate system in which the eyeball center is fixed
      $\{3DIrisCircle_{HCS}\}_{+,-}$←CircularConeIntersection (IrisCone$_{HCS}$,$r_I$)

---

As specified in the step (i) hereinabove; the Iris circle was brought to a coordinate system in which the eyeball center was fixed, which was done assuming that the iris is a circle positioned on the surface of the eyeball sphere (which projection results in the ellipse detected by the camera). Thus the circular intersections with the cone, were its possible locations; and using rI=6 mm–population mean (of iris' dimensions) resulted in 2 possible iris circles— denoted +,−. The Iris(Circle) rotation angles were then denoted η, ξ.

2. {E, reye}Eye∈L,R'i←Swirsky ({{3DIrisCircleHCS}+,−}i=1N)

An initial guess for eyeball centers and Radii was achieved using the algorithm specified in [2]—for each eye the Iris circles was found, which a normal vector intersects in a single point, and that point. The eyes' rotations (i) was also obtained—which are the Iris circle normal in the head coordinate system:

In this step, the (rotated) eye model was obtained from the head coordinate system and the projection operator was computed by first applying rotation and translation with RH−1, −TH followed by multiplication with the camera projection matrix K of the 3D eye, while Ri was the established eye rotation in every frame Fi—also applied using matrix multiplication of the simplified 3D eye model (a sphere of radius $r_{eye}$ with limbus in radius IE centered at ER,L). These parameters defined the (hidden from camera) eyeball center positions with regard to head-pose, and thus mapping to the facial landmarks which allowed the inference of the eyeball center from the camera-detected visible landmarks.

The process was repeated for both eyes resulting in EL, ER, IEL, IER leading to a personalized parameter of the locations of both eyes as related to each other, constrained anatomically by the eyeball centers.

For example, the algorithm used for eye region localization can comprise assigning a vector to every pixel in the edge map of the eye area, which points to the closest edge pixel. The length and the slope information of these vectors can consequently be used to detect and localize the eyes by matching them with a training set (obtained ion the intrinsic calibration phase). Additionally, or alternatively, a multi-stage approach may be used for example to detect facial features (among them are the eye centers, or pupils) using a face detector, with pairwise reinforcement of feature responses, and a final refinement by using an active appearance model (AAM). Other methods of eye region localization can be employed, for example: using edge projection (GPF) and support vector machines (SVMs) to classify estimates of eye centers using an enhanced version of Reisfeld's generalized symmetry transform for the task of eye location, using Gabor filters, using feature triplets to generate a face hypothesis, register them for affine transformations, and verify the remaining configurations using two SVM classifiers, and using an eye detector to validate the presence of a face and to initialize an eye locator, which, in turn, refines the position of the eye using the SVM on optimally selected Haar wavelet coefficients. These methods can be used either alone or in combination with the face detection algorithm.

The face detection algorithm may be further used to compute head pose in six degrees of freedom (DOF). Some exemplary methods for estimating head pose localization and angular orientation can be a detector array method (DAM), in which a series of head detectors are trained, each configured to classify a specific pose and assign a discrete pose to the detector with the greatest support, a technique using machine learning and neural networks. This method can be supplanted or replaced by Nonlinear Regression Methods (NRM), which estimates head pose by learning a nonlinear functional mapping from the image space to one or more pose directions, normally using regression tools and neural networks. Additional methods can be, for example: a flexible algorithm, in which a non-rigid model is fit to the facial structure of the user in the image and wherein head pose is estimated from feature-level comparisons or from the instantiation of the parameters, using the location of extracted features such as the eyes, mouth, and nose tip to determine pose from their relative configuration, recovering the global pose change of the head from the observed movement between video frames then using weighted least squares on particle filtering to discern the head pose. In an exemplary implementation, the head pose determination method used may be a hybrid method, combining one or more of the aforementioned methods to overcome the limitations inherent in any single approach. For example, using local feature configuration (eyes, nose tip, lips, e.g.,) and sum of square differences (SSD) tracking, or principal component analysis comparison and continuous density hidden Markov modeling (HMM). The existing models are additionally extended to include, for example eyeball landmarks, both visible (e.g., pupil-center, pupil contour and limbus contour) as well as non-visible (e.g., eyeball center, iris-corneal offset, cornea major axis). These are determined through a calibration process between the visible facial-eye landmarks (or feature) to the non-visible face-eye landmarks (or features) through a process of fixation, or focusing, by a subject on a known target presented to the subject. The final outcome of this procedure is a personalized face-eye model (which is configured per-user) that best estimates the location of the visible and non-visible landmarks (or features) in the sense of Gaze-reprojection (matrix)-error (GRE).

In an exemplary implementation, using DNN architecture of stacked hourglass is used because of the need to make the system user specific, implying the ability to capture data over numerous (application-specific) scales and resolutions. Thus, the DNN can consist of, for example, at least three (3) Stacked Hourglass heat-maps, in three pipelines; one for the face (a scale larger than the eyes landmark localizing), left eye, and right eye modules (L and R eyes—same scale), with an input of eyes region image, each of at least the size 100 by 100 pixels in another implementation.

In the context of the disclosed methods, systems and programs provided, the term "stacked hourglass" refers in some implementations to the visualization of the initial sampling followed by the steps of pooling and subsequent convolution (or up-sampling) used to get the final output of the fully connected (FC) stack layers. Thus, the DNN architecture is configured to produce pixel-wise heat maps, whereby the hourglass network pools down to a very low resolution, then reconvolutes and combines features across multiple resolutions.

In an exemplary implementation, for each eyeball region that was successfully located by the detection algorithm, the DNN outputs the subject's iris and pupil elliptical contours, defined by the ellipse center, radii of ellipse, and their orientation. In addition, for each face image that was successfully located by the detection algorithm, the DNN outputs the subject's head location in 3D space (x, y, z, coordinates) in the camera coordinate system as well as the subject's roll, yaw, and pitch. Additionally, another DNN receives as an input the face region to train on estimating the gaze direction and origin. This DNN consists of a convolutional layer, followed by pooling, and another convolution layer which is then used as input to a fully connected layer. The fully connected layer also obtains input from the eye-related DNN.

The instant gaze estimation (interchangeable with point of reference or point-of-regard (PoR)) system is of high-precision (less than 1 degree of error accuracy referring to the angular location of the eye relative to the optic sensor array).

Figure 11:
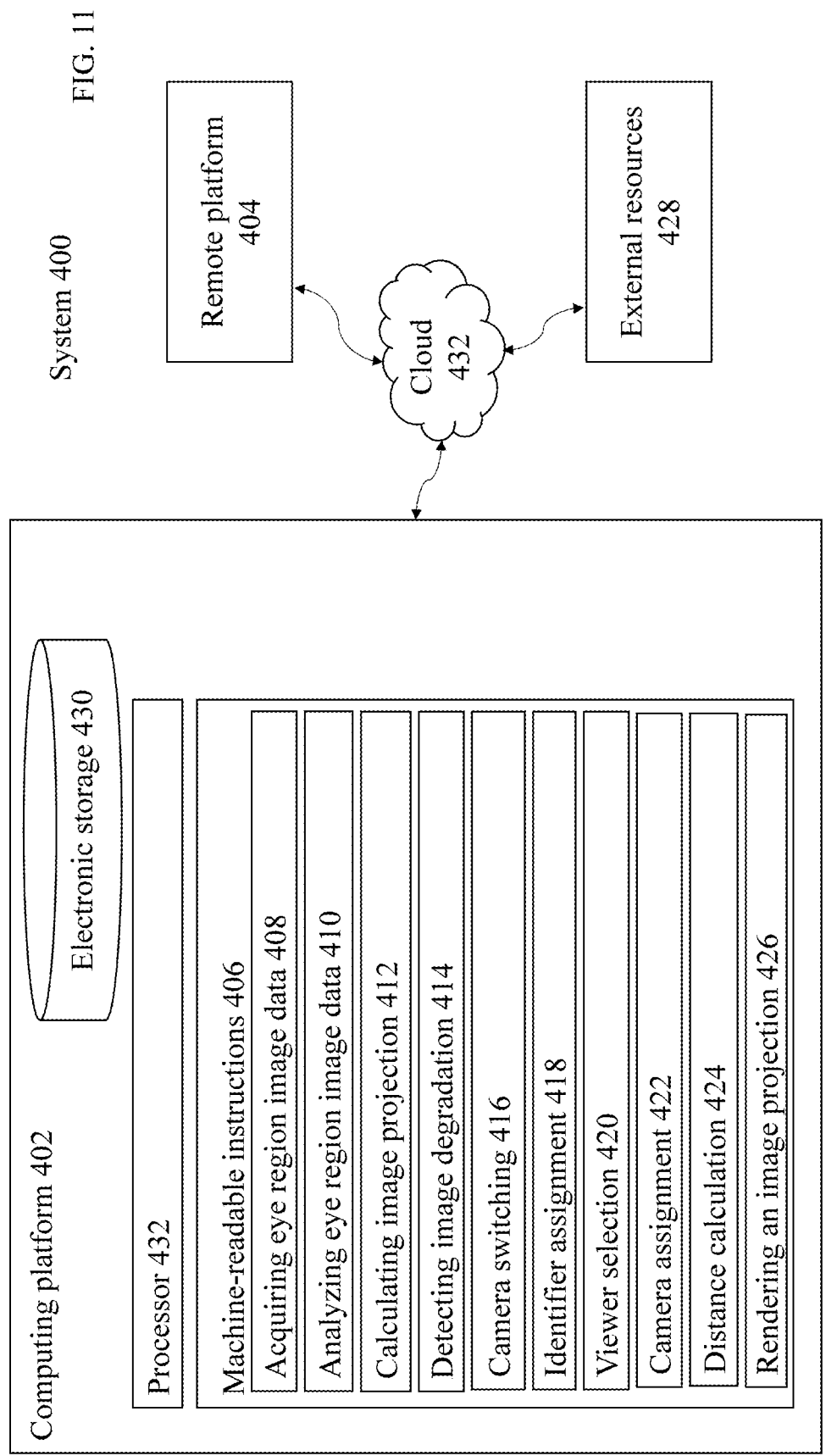
FIG. 11 illustrates an example system configured for multi-user gaze-tracking for personalized rendering from a single 3D display, according to some embodiments of the present disclosure.

FIG. 11 illustrates an example system 400 configured for multi-user gaze-tracking for personalized rendering from a single 3D display, according to some embodiments of the present disclosure. In some implementations, system 400 may include one or more computing platforms 402. Computing platform(s) 402 may be configured to communicate with one or more remote platforms 404 according to a client/server architecture, a peer-to-peer architecture, cloud architecture, or other architectures. Remote platform(s) 404 may be configured to communicate with other remote platforms via computing platform(s) 402 and/or according to a client/server architecture, a peer-to-peer architecture, cloud architecture, or other architectures. Users may access system 400 via remote platform(s) 404. It is noted that the system 400 and computing platform 402 may be integrated with a 3D display (e.g., as a part of the display electronics), or provided physically separately but in communication with the electronics of the 3D display. In some embodiments, computing platform 402 may be located in a cloud environment as in cloud 432 (e.g., public, private, or hybrid).

Computing platform 402 may include one or more processors 434 configured by machine-readable instructions 406 that are configured to implement the camera evaluation, position detection, gaze tracking, and 3D display rendering methods described herein. Machine-readable instructions 406 may include one or more instruction sets. The instruction sets may include computer program sets. The instruction sets may perform one or more functions when executed on a computing system, including acquiring eye region image data 408, e.g., by using a camera to obtain images of a viewer; analyzing eye region image data 410 to obtain gaze tracking or PoR estimates, e.g., using the algorithms described above; calculating image projection 412; detecting image degradation 414; camera switching 416; identifier assignment 418; viewer selection 420; camera assignment 422, distance calculation 424, rendering an image projection 426, and/or other instruction sets.

Acquiring eye region image data 408 may be configured to acquire eye region image data of a plurality of viewers within a field of view of at least one camera associated with a 3D-enabled digital display. Any suitable camera may be provided, including but not limited to cameras for recording or processing image data, such as still images or video images. Acquiring eye region image data may be performed by a camera at a distance of at least 0.2 meters from at least one of the plurality of viewers. Suitable distances may include acquiring eye region image data at a distance from about 0.2 meters to about 3 meters. In some implementations, by way of non-limiting example, acquiring eye region image data may be performed by at least one of a laptop camera, a tablet camera, a smartphone camera, a digital billboard camera, or a digital external camera. A smartphone camera may be any camera provided with a mobile device such as a mobile phone or other mobile computing device. A digital external camera may include any other stand-alone camera including but not limited to a surveillance camera, or a body-mounted camera or wearable camera that can be mounted or otherwise provided on the viewer (e.g., on glasses, a watch, or otherwise strapped or affixed to the viewer). In some implementations, acquiring eye region image data may be performed with active illumination. In other implementations, acquiring eye region image data may be performed without active illumination. Active illumination may include a camera flash and/or any other suitable lighting that is provided for the purpose of image capture separate and apart from artificial or natural lighting of the surrounding environment. By way of non-limiting example, the eye region image data may include at least one of pupil image data, iris image data, or eyeball image data.

For example, pupil image data, iris image data, and eyeball image data may be obtained from images of the viewer. Pupil image data may refer to the data regarding the viewer's pupil, or the darker colored opening at the center of the eye that lets light through to the retina. Iris image data may refer to data regarding the viewer's iris, or the colored part of the eye surrounding the pupil. Eyeball image data may refer to data regarding any portion of the viewer's eyeball, including the sclera, the limbus, the iris and pupil together, or the area within the neurosensory retina (the portion of the macula responsible for capturing incident light).

Analyzing eye region image data 410 may be involve analyzing the eye region image data to determine at least one 3D eye position, at least one gaze angle, and at least one point-of-regard for at least one viewer relative to at least one camera associated with the 3D-enabled digital display. The at least one gaze angle may include yaw and pitch. By way of non-limiting example, the analyzing the eye region image data to determine at least one 3D eye position, at least one gaze angle, and at least one point-of-regard for at least one viewer relative to at least one camera associated with the 3D-enabled digital display may include mapping the eye region image data to a Cartesian coordinate system. By way of non-limiting example, the analyzing the eye region image data to determine at least one 3D eye position, at least one gaze angle, and at least one point-of-regard for at least one viewer relative to at least one camera associated with the 3D-enabled digital display may include unprojecting the pupil and limbus of both eyeballs onto the Cartesian coordinate system to give 3D contours of each eyeball. The limbus forms the border between the cornea and the sclera (or "white") of the eyeball.

Analyzing eye region image data 410 may include analyzing the eye region image data for at least one of engagement with the 3D-enabled digital display. By way of non-limiting example, the analyzing the eye region image data 410 may further include analyzing at least one eye state characteristic selected from at least one of a blink, an open state being either fixation or saccade, or a closed state.

Calculating image projection 412 may include calculating a plurality of image projections for display by the single 3D display. Image projections may be rendered as pixels of a 2D or 3D display, as voxels, or as any other suitable output of the 3D display (e.g., a point in space for a light field display or a holographic display). Suitable 3D displays include, e.g., lenticular displays, stereoscopic displays, light field displays, and holographic displays. At least one of the plurality of projections may be calculated to be appropriate for each viewer's position and point-of-regard with respect to the 3D-enabled digital display.

Detecting image degradation 414 may include detecting image degradation in the eye region image data. For example, the viewer may turn his or her head or walk toward or away from the camera, thus degrading the eye region image data obtainable by one of the cameras.

Camera switching 416 may include switching to a different camera based on the conditions or degradation in the eye region image data. For example, another camera may have a better or worse view of the viewer as the viewer turns his or her head or walks toward or away from the camera.

Identifier assignment 418 may include assigning a unique identifier such as a digital identifier or a digital embedding identifier to each face corresponding to each viewer among the plurality of viewers. The identifier may be associated with at least one sequence of image projections calculated for each viewer. Any suitable identifier may be used, such as alpha and/or numerical sequence(s), bits, or other coded means of identification. Identifiers may be predefined or defined based on a calculation or determination of a processing algorithm. By way of these identifiers, multiple viewers can be tracked relative to cameras associated with a 3D display, and 3D rendered projections specific to each viewer can be embedded with the identifier to ensure that each viewer is shown a rendered image appropriate to that viewer's head pose and point-of-regard in relation to the 3D display.

Viewer selection 420 may include selecting at least two viewers based on at least one property of a 3D display or at least one eye property of the at least two viewers.

Camera assignment 422 may include assigning at least one camera to at least one viewer based on an assessment of which camera among a plurality of cameras has the best viewing angle or imaging conditions of an eye region of at least one viewer. Assessment may be any suitable evaluation or estimation of the nature or quality of the imaging conditions, such as lighting, distance, resolution, obstruction or lack thereof, movement or lack thereof, or camera zoom capability. Imaging conditions may include the ability of the camera to capture imaging data and may be based on any of a variety of different factors, such as physical conditions of the viewer, environmental conditions, or the 3D display itself.

Distance calculation 424 may be configured to calculate a distance from at least one camera to at least one viewer using image analysis. Any suitable image analysis may be implemented, such that meaningful information is extracted from digital images via algorithmic analysis and processing of data captured by the camera(s).

Rendering an image projection 426 may include rendering the plurality of image projections on the single 3D display.

In some implementations, computing platform(s) 402, remote platform(s) 404, and/or external resources 428 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which computing platform(s) 402, remote platform(s) 404, and/or external resources 428 may be operatively linked via some other communication media.

A given remote platform 404 may include one or more processors configured to execute computer instruction sets. The computer program instruction sets may be configured to enable an expert or user associated with the given remote platform 404 to interface with system 400 and/or external resources 428, and/or provide other functionality attributed herein to remote platform(s) 404. By way of non-limiting example, a given remote platform 404 and/or a given computing platform 402 may include one or more of a cloud or datacenter, a virtual private network, a server, a desktop computer, a laptop computer, a handheld computer, a tablet computing platform, a NetBook, a Smartphone, a gaming console, and/or other computing platforms.

External resources 428 may include sources of information outside of system 400, such as external entities participating with system 400, and/or other resources. In some implementations, some or all of the functionality attributed herein to external resources 428 may be provided by resources included in system 400.

Computing platform(s) 402 may include non-transitory electronic storage 430 operable to store any of machine readable instructions 406-426, one or more processors 432, and/or other components. Computing platform 402 may include communication lines, or ports to enable the exchange of information with a network and/or other computing platforms. Illustration of computing platform 402 in FIG. 11 is not intended to be limiting. Computing platform 402 may include a plurality of hardware, software, and/or firmware components operating together to provide the functionality attributed herein to computing platform 402. For example, computing platform 402 may be implemented by one or more clouds of computing environments operating together as computing platform 402.

Electronic storage 430 may comprise non-transitory storage media that electronically stores information. The electronic storage media of electronic storage 430 may include one or both of system storage that is provided integrally (i.e., substantially non-removable) with computing platform(s)

402 and/or removable storage that is removably connectable to computing platform(s) 402 via, for example, a port (e.g., a USB port, a firewire port, etc.) or a drive (e.g., a disk drive, etc.). Electronic storage 430 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 430 may include one or more virtual storage resources (e.g., cloud storage, a virtual private network, and/or other virtual storage resources). Electronic storage 430 may store software algorithms, information determined by processor(s) 432, information received from computing platform(s) 402, information received from remote platform(s) 404, and/or other information that enables computing platform(s) 402 to function as described herein.

Processor(s) 434 may be configured to provide information processing capabilities in computing platform(s) 402. As such, processor(s) 434 may include one or more of a digital processor, an analog processor, a digital circuit designed to process information, an analog circuit designed to process information, a state machine, and/or other mechanisms for electronically processing information. Although processor(s) 434 is shown in FIG. 11 as a single entity, this is for illustrative purposes only. In some implementations, processor(s) 434 may include a plurality of processing units. These processing units may be physically located within the same device, or processor(s) 434 may represent processing functionality of a plurality of devices operating in coordination. Processor(s) 434 may be configured to execute instruction sets 408, 410, 412, 414, 416, 418, 420, 422, 424, and/or 426, and/or other instruction sets. Processor(s) 434 may be configured to execute instruction sets 408, 410, 412, 414, 416, 418, 420, 422, 424, and/or 426, and/or other modules by software; hardware; firmware; some combination of software, hardware, and/or firmware; and/or other mechanisms for configuring processing capabilities on processor(s) 434. As used herein, the term "instruction set" may refer to any structure, component, or set of components that enable the performance of the functionality attributed to the instruction set. This may include one or more physical processors during execution of processor readable instructions, the processor readable instructions, circuitry, hardware, storage media, or any other components.

It should be appreciated that although instruction sets 408, 410, 412, 414, 416, 418, 420, 422, 424, and/or 426 are illustrated in FIG. 11 as being implemented within a single processing unit, in implementations in which processor(s) 432 includes multiple processing units, one or more of instruction sets 408, 410, 412, 414, 416, 418, 420, 422, 424, and/or 426 may be implemented remotely from the other instruction sets. The description of the functionality provided by the different instruction sets 408, 410, 412, 414, 416, 418, 420, 422, 424, and/or 426 described below is for illustrative purposes, and is not intended to be limiting, as any of instruction sets 408, 410, 412, 414, 416, 418, 420, 422, 424, and/or 426 may provide more or less functionality than is described. For example, one or more of instruction sets 408, 410, 412, 414, 416, 418, 420, 422, 424, and/or 426 may be eliminated, and some or all of its functionality may be provided by other ones of instruction sets 408, 410, 412, 414, 416, 418, 420, 422, 424, and/or 426. As another example, processor(s) 434 may be configured to execute one or more additional instruction sets that may perform some or all of the functionality attributed below to one of instruction sets 408, 410, 412, 414, 416, 418, 420, 422, 424, and/or 426.

Figure 12B:
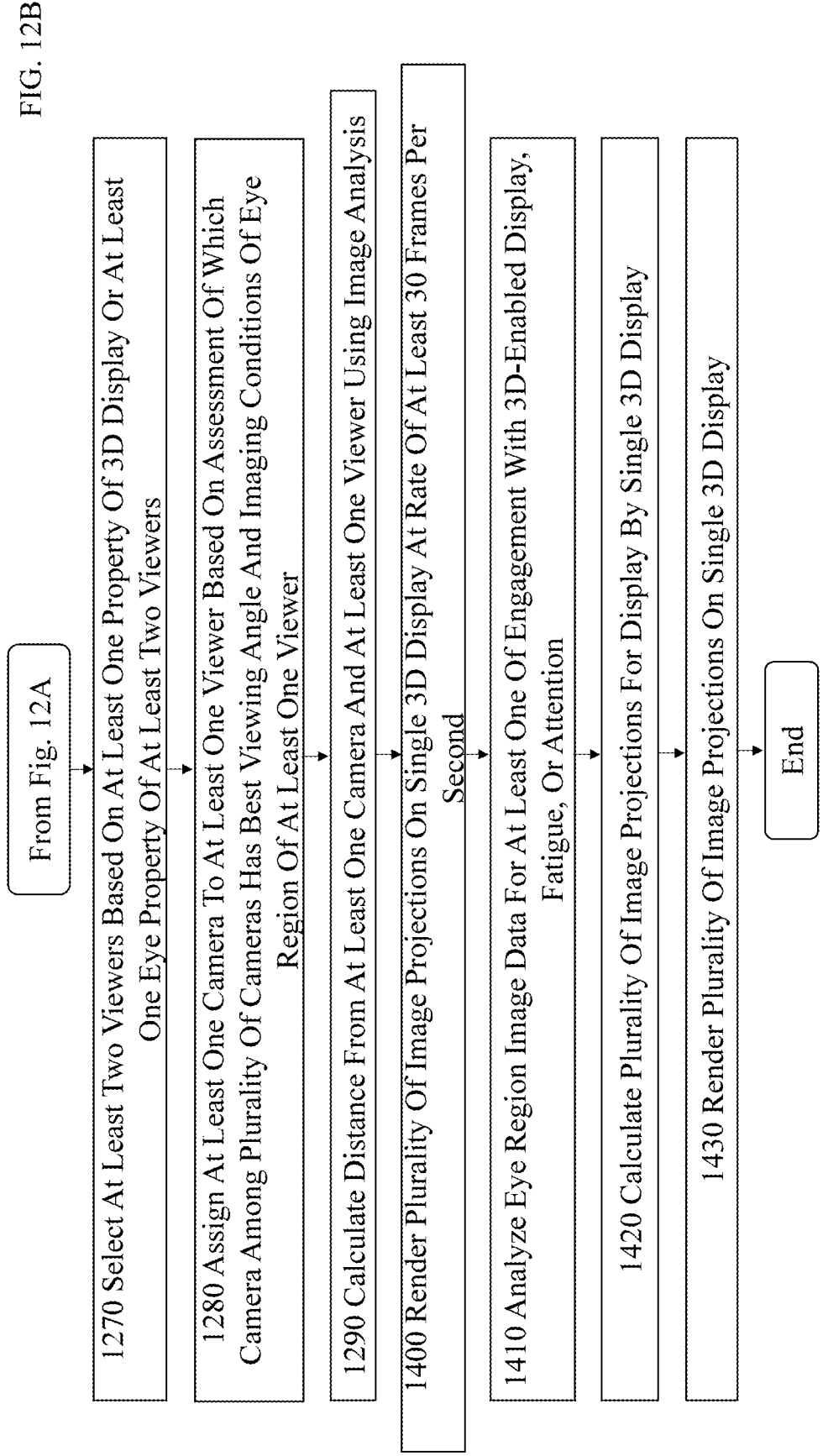
Figure 14C:
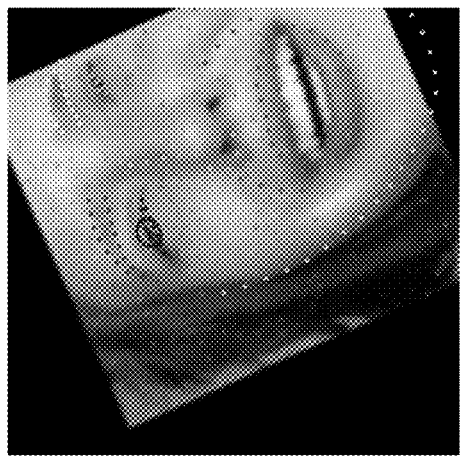
FIGS. 14A, 14B, and 14C show facial landmark tagging according to some embodiments of the present disclosure, showing example images containing a face and landmarks output by a facial landmark detector model.
Figure 14B:
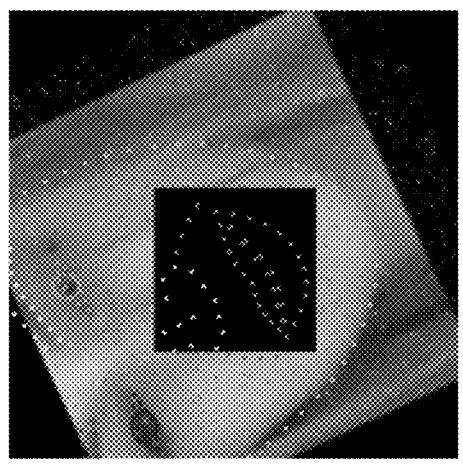
Figure 14A:
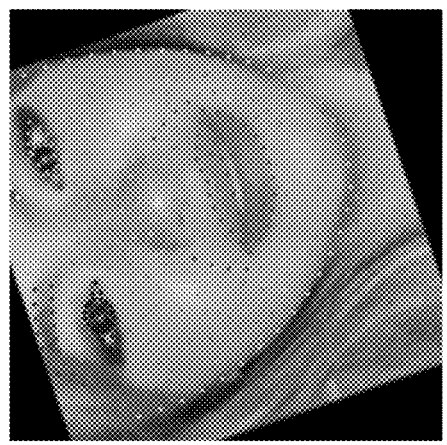
Figure 15:
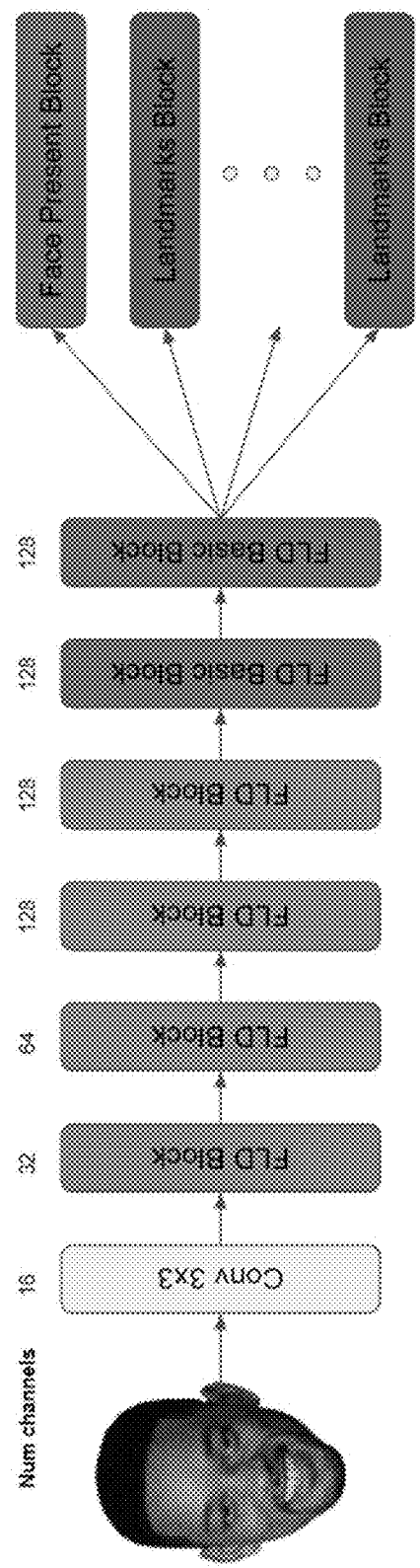
FIG. 15 depicts a deep learning architecture for face landmark detection.
Figure 16C:
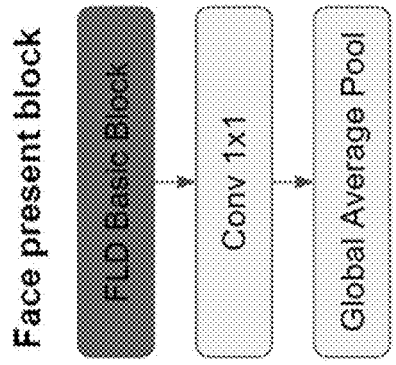
FIGS. 16A, 16B, and 16C show component flows of a face landmark detection network according to the present disclosure.
Figure 16B:
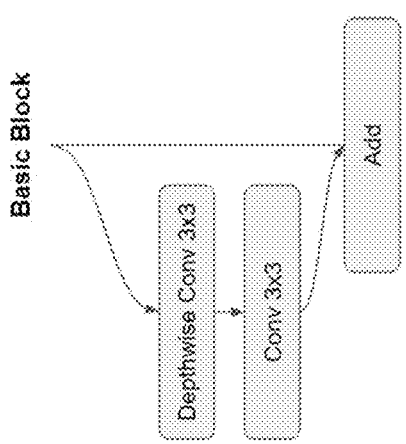
Figure 16A:
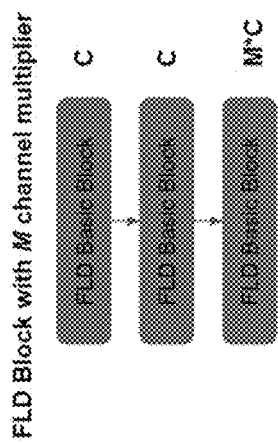
Figure 17:
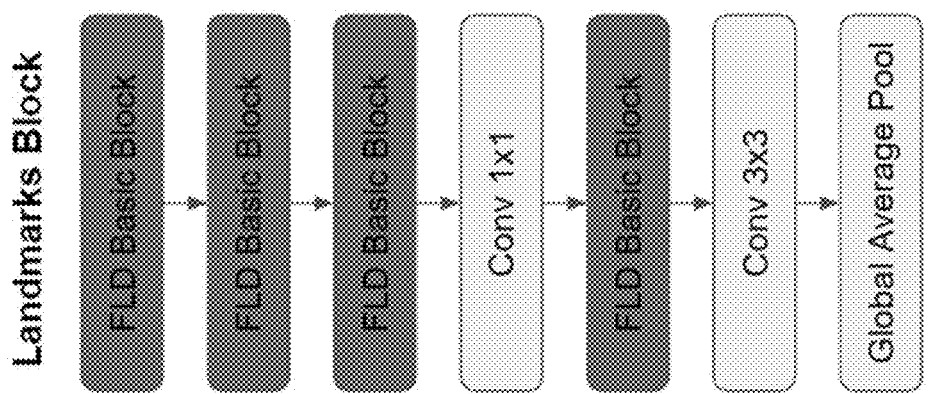
FIG. 17 depicts a component flow of the landmark detection network according to the present disclosure.

FIGS. 12A and 12B are flowcharts illustrating a method for multi-user gaze-tracking for personalized rendering from a single 3D display, according to some embodiments of the present disclosure. The operations of the methods of FIGS. 12A and 12B presented below are intended to be illustrative. In some implementations, these methods may be accomplished with one or more additional operations not described, and/or without one or more of the operations discussed. Additionally, the order in which the operations are illustrated in FIGS. 12A and 12B and described below is not intended to be limiting.

In some implementations, the methods of FIGS. 12A and 12B may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations in response to instructions stored electronically on a non-transitory electronic storage medium. The one or more processing devices may include one or more devices configured through hardware, firmware, and/or software to be specifically designed for execution of one or more of the operations of the methods of FIGS. 12A and 12B.

As FIG. 12A illustrates, an operation 1200 may include acquiring eye region image data of a plurality of viewers within a field of view of at least one camera associated with a 3D-enabled digital display. Operation 1200 may be performed by one or more hardware processors configured by machine-readable instructions including an instruction set that is the same as or similar to acquiring eye region image data 408, in accordance with one or more implementations.

An operation 1210 may include analyzing the eye region image data to determine at least one 3D eye position, at least one gaze angle, and at least one point-of-regard for at least one viewer relative to at least one camera associated with the 3D-enabled digital display. Operation 1210 may be performed by one or more hardware processors configured by machine-readable instructions including an instruction set that is the same as or similar to analyzing eye region image data 410, in accordance with one or more implementations.

An operation 1220 may include calculating a plurality of image projections for display by the single 3D display. At least one of the plurality of projections may be calculated to be appropriate for each viewer's position and point-of-regard with respect to the 3D-enabled digital display. Operation 1220 may be performed by one or more hardware processors configured by machine-readable instructions including an instruction set that is the same as or similar to calculating image projection 412, in accordance with one or more implementations.

An operation 1230 may include detecting degradation in the eye region image data. Operation 1230 may be performed by one or more hardware processors configured by machine-readable instructions including an instruction set that is the same as or similar to detecting image degradation 414, in accordance with one or more implementations.

An operation 1240 may include switching to a different camera based on the degradation in the eye region image data. Operation 1240 may be performed by one or more hardware processors configured by machine-readable instructions including an instruction set that is the same as or similar to camera switching 416, in accordance with one or more implementations.

An operation 1250 may include analyzing the eye region image data for at least one of engagement with the 3D-enabled digital display, fixation or saccade. Operation 1250 may be performed by one or more hardware processors configured by machine-readable instructions including an instruction set that is the same as or similar to eye region image data analysis 410, in accordance with one or more implementations.

An operation 1260 may include assigning a digital embedding identifier to each face for each viewer among the plurality of viewers. The identifier may be associated with at least one sequence of image projections calculated for each viewer. Operation 1260 may be performed by one or more hardware processors configured by machine-readable instructions including an instruction set that is the same as or similar to identifier assignment 418, in accordance with one or more implementations.

Referring now to FIG. 12B, an operation 1270 may include selecting at least two viewers based on at least one property of a 3D display or at least one eye property of the at least two viewers. Operation 1270 may be performed by one or more hardware processors configured by machine-readable instructions including an instruction set that is the same as or similar to viewer selection 420, in accordance with one or more implementations.

An operation 1280 may include assigning at least one camera to at least one viewer based on an assessment of which camera among a plurality of cameras has the best viewing angle and imaging conditions of an eye region of at least one viewer. Operation 1280 may be performed by one or more hardware processors configured by machine-readable instructions including an instruction set that is the same as or similar to camera assignment 422, in accordance with one or more implementations.

An operation 1290 may include calculating a distance from at least one camera and at least one viewer using image analysis. Operation 1290 may be performed by one or more hardware processors configured by machine-readable instructions including an instruction set that is the same as or similar to distance calculation 424, in accordance with one or more implementations.

An operation 1400 may include rendering the plurality of image projections on the single 3D display. Operation 1400 may be performed by one or more hardware processors configured by machine-readable instructions including an instruction set that is the same as or similar to rendering an image projection 426, in accordance with one or more implementations.

An operation 1410 may include analyzing the eye region image data for at least one of engagement with the 3D-enabled digital display, fixation, or saccade. Operation 1410 may be performed by one or more hardware processors configured by machine-readable instructions including an instruction set that is the same as or similar to analyzing eye region image data 410, in accordance with one or more implementations.

An operation 1420 may include calculating a plurality of image projections for display by the single 3D display. Operation 1420 may be performed by one or more hardware processors configured by machine-readable instructions including an instruction set that is the same as or similar to calculating image projection 412, in accordance with one or more implementations.

An operation 1430 may include rendering the plurality of image projections on the single 3D display. Operation 1430 may be performed by one or more hardware processors configured by machine-readable instructions including an instruction set that is the same as or similar to rendering an image projection 426, in accordance with one or more implementations.

Referring now to FIG. 13, an operation 1300 may include acquiring face and eye region image data for a plurality of viewers within a field of view of at least one camera associated with a 3D-enabled display.

Operation 1310 may include analyzing the eye region image data to determine at least one 3D eye position, at least one eye state, at least one gaze angle, and at least one point-of-regard for at least one viewer relative to at least one camera associated with the 3D-enabled display.

Operation 1320 may include calculating a plurality of image projections for display by the single 3D display, wherein at least one of the plurality of projections is calculated to be appropriate for each viewer's position and point-of-regard with respect to the 3D-enabled display.

This 3D Display technology when paired with gaze tracking, is also suited as a treatment tool for a variety types of eye aberrations, including, but not limited to Amblyopia and its effect in stereoscopic vision, as it's simulated through the Gaze-Tracking the ability to deliver equivalent optical input to each eye that simulates an authentic 3D-perception.

Figure 18:
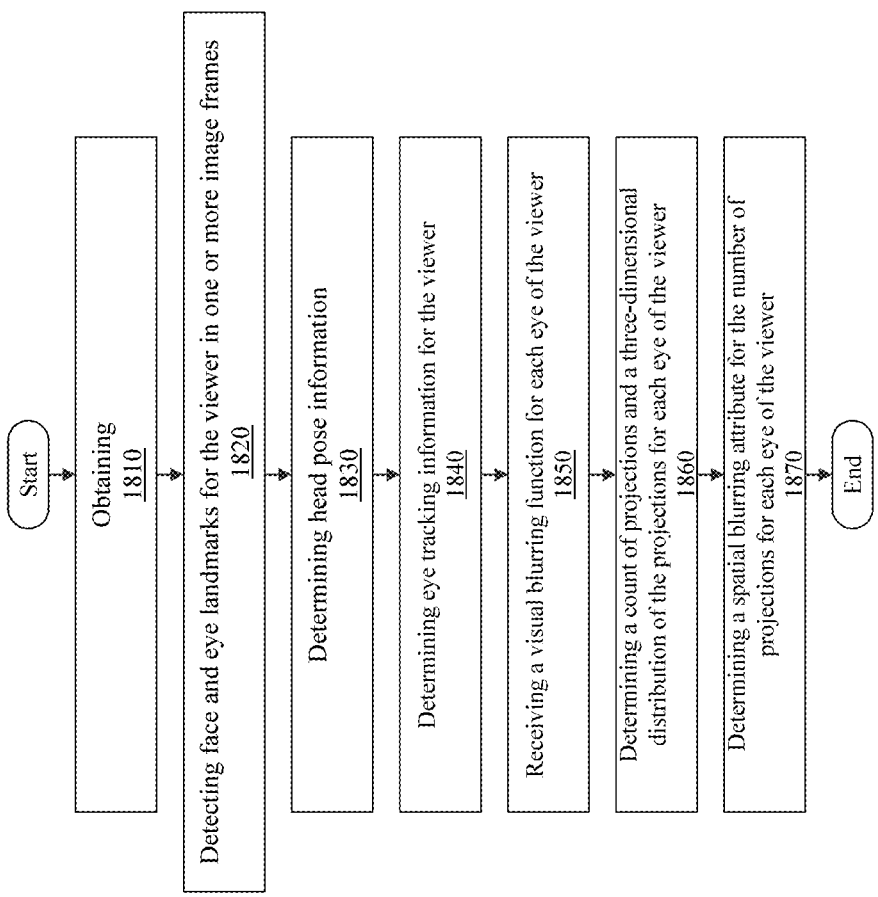
FIG. 18 is a flowchart illustrating a method for enabling projection of images, according to some embodiments of the present disclosure.

FIG. 18 is a flowchart that describes a method for enabling projection of images, according to some embodiments of the present disclosure. In some embodiments, at 1810, the method may include obtaining face image data and eye region image data for a viewer within a field of view of at least one camera in proximity to a 3D-enabled digital display. At 1820, the method may include detecting face and eye landmarks for the viewer in one or more image frames based on the face image data. At 1830, the method may include determining head pose information based on the face image data and eye region image data.

In some embodiments, at 1840, the method may include determining eye tracking information for the viewer based on the face image data, eye region image data, and head pose information, and the eye tracking information. At 1850, the method may include receiving a visual blurring function for each eye of the viewer. In some embodiments, $$f_{blur}(d, vfov, t) = A \cdot |\sin(\alpha \pi t)| \cdot \begin{cases} K_{foveal} & vfov \in \text{foveal } (d) \\ K_{parafoveal} & vfov \in \text{parafoveal} \\ K_{peripheral} & vfov \in \text{peripheral} \end{cases}$$

t=temporal interval, d=distance to scrteen, vfov=visual field of view, A—blureing Amplitude, |·|=absolute value operator $$K_{peripheral} = \begin{cases} \begin{bmatrix} k_{diag} & k(n\text{Diag}) & d_{diag} \\ k(n\text{Diag}) & k(\text{center}) & k(n\text{Diag}) \\ k_{diag} & k(n\text{Diag}) & k_{diag} \end{bmatrix} & \alpha t \notin \mathbb{Z} \\ I_{3\times 3} & \text{else} \end{cases}$$

$$K_{parafoveal} = \begin{cases} \begin{bmatrix} \frac{k_{diag}}{2} & \frac{k_{nDiag}}{2} & \frac{k_{nDiag}}{2} & \frac{k_{nDiag}}{2} & \frac{k_{diag}}{2} \\ \frac{k_{nDiag}}{2} & k_{diag} & k_{nDiag} & k_{diag} & \frac{k_{nDiag}}{2} \\ \frac{k_{nDiag}}{2} & k_{nDiag} & k(\text{center}) & k_{nDiag} & \frac{k_{nDiag}}{2} \\ \frac{k_{nDiag}}{2} & k_{diag} & k_{nDiag} & k_{diag} & \frac{k_{nDiag}}{2} \\ \frac{k_{diag}}{2} & \frac{k_{nDiag}}{2} & \frac{k_{nDiag}}{2} & \frac{k_{nDiag}}{2} & \frac{k_{diag}}{2} \end{bmatrix} & \alpha t \notin \mathbb{Z} \\ I_{5\times 5} & \text{else} \end{cases}$$

$$K_{foveal} =$$

$$\begin{cases} \begin{bmatrix} \frac{k_{diag}}{4} & \frac{k_{nDiag}}{4} & \frac{k_{nDiag}}{4} & \frac{k_{nDiag}}{4} & \frac{k_{nDiag}}{4} & \frac{k_{nDiag}}{4} & \frac{k_{diag}}{4} \\ \frac{k_{nDiag}}{4} & \frac{k_{diag}}{2} & \frac{k_{nDiag}}{2} & \frac{k_{nDiag}}{2} & \frac{k_{nDiag}}{2} & \frac{k_{diag}}{2} & \frac{k_{nDiag}}{4} \\ \frac{k_{nDiag}}{4} & \frac{k_{nDiag}}{2} & k_{diag} & k_{nDiag} & k_{diag} & \frac{k_{nDiag}}{2} & \frac{k_{nDiag}}{4} \\ \frac{k_{nDiag}}{4} & \frac{k_{nDiag}}{2} & k_{nDiag} & k(center) & k_{nDiag} & \frac{k_{nDiag}}{2} & \frac{k_{nDiag}}{4} \\ \frac{k_{nDiag}}{4} & \frac{k_{nDiag}}{2} & k_{diag} & k_{nDiag} & k_{diag} & \frac{k_{nDiag}}{2} & \frac{k_{nDiag}}{4} \\ \frac{k_{nDiag}}{4} & \frac{k_{diag}}{2} & \frac{k_{nDiag}}{2} & \frac{k_{nDiag}}{2} & \frac{k_{nDiag}}{2} & \frac{k_{diag}}{2} & \frac{k_{nDiag}}{4} \\ \frac{k_{diag}}{4} & \frac{k_{nDiag}}{4} & \frac{k_{nDiag}}{4} & \frac{k_{nDiag}}{4} & \frac{k_{nDiag}}{4} & \frac{k_{nDiag}}{4} & \frac{k_{diag}}{4} \end{bmatrix} & \alpha t \notin \mathbb{Z} \\ I_{7\times 7} & \text{else} \end{cases}$$

In some embodiments, the final output for the rendering module is the 2D image projection per each eye that is then arbitrated by the AI module, to distribute the views correctly and efficiently to the user:

1.

$$\text{Point-Of-Regard-Group } (PORG) =$$
$$\{\text{foveal } (d), \text{parafoveal } (d), \text{peripheral } (d)\}$$

$$\text{Image}_{Non-Amblyopic}(X, Y) =$$
$$\begin{cases} \text{Image}_{Original}(X, Y) * f_{blur}(d, vfov, t) & X, Y \in PORG \\ \text{Image}_{Original}(X, Y) & \text{else} \end{cases}$$

2.

$$\text{Image}_{Amblyopic}(X, Y) = \text{Image}_{Original}(X, Y)$$

$(X, Y)$–pixel location in the image plane, $*$ –is the 2D covolution operation $\text{Image}_{Original}$ = digital image presneted on the digital display At 1860, the method may include determining a count, or otherwise identifying a suitable count of projections and a three-dimensional distribution of the projections for each eye of the viewer based on the eye tracking information.

At 1870, the method may include determining a spatial blurring attribute for the number of projections for each eye of the viewer based at least in part on the received visual blurring function of the viewer. A point of regard (PoR) of each eye of the viewer. Eye state of each eye of the viewer. Gaze direction of each eye of the viewer. Eye region illumination information for each eye of the viewer. A position of each eye of the viewer relative to the 3D-enabled digital display.

In some embodiments, a contrast sensitivity function (CSF) indicative of a visual acuity of the viewer further comprises, the method may include performing one or more additional steps. Data indicative of a performance of a contrast function sensitivity performance. In some embodiments, a contrast sensitivity function (CSF) indicative of a visual acuity of the viewer further comprises, the method may include performing one or more additional steps. Data indicative of a performance of a spatial frequency sensitivity performance.

In some embodiments, a contrast sensitivity function (CSF) indicative of a visual acuity of the viewer further comprises, the method may include performing one or more additional steps. A function indicative of a visual acuity performance of the user at a distance from the 3D-enabled digital display and its minimal Spatial Frequency Threshold for a trackable object on the digital display. In some embodiments, receiving the visual acuity profile may further comprise an amblyopic eye classification for each eye of the viewer.

In some embodiments, determining a count of projections and a three-dimensional distribution of the projections for each eye of the viewer based on the eye tracking information further comprises, the method may include performing one or more additional steps. In some embodiments, applying the visual blurring function of the viewer to an area of interest of a projected image for the at least one eye of the viewer further comprises, the method may include performing one or more additional steps. Spatially adjusting the area of interest of the projected image for at least one eye.

Figure 19:
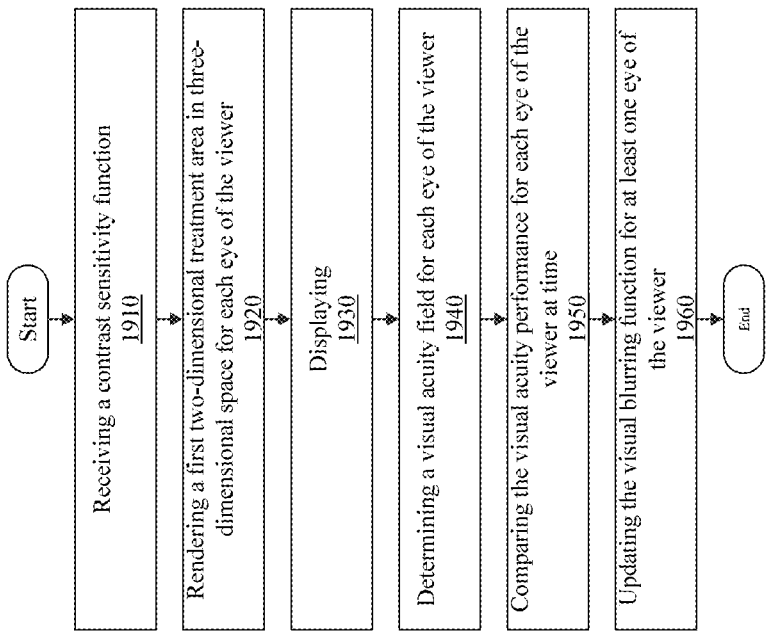
FIG. 19 is a flowchart further illustrating the method for enabling projection of images from FIG. 18, according to some embodiments of the present disclosure.

FIG. 19 is a flowchart that further describes the method for enabling projection of images from FIG. 18, according to some embodiments of the present disclosure. In some embodiments, receiving a visual blurring function of the viewer further comprises, the method may include 1910. In some embodiments, a contrast sensitivity function (CSF) indicative of a visual acuity of the viewer further comprises, the method may include performing one or more additional steps. For an exemplary description of a CSF, see National Research Council (US) Committee on Vision. Emergent Techniques for Assessment of Visual Performance. Washington (DC): National Academies Press (US); 1985. CONTRAST SENSITIVITY FUNCTION. Available from: https://www.ncbi.nlm.nih.gov/books/NBK219042/; and Vision Models for High Dynamic Range and Wide Colour Gamut Imaging, Techniques and Applications, Computer Vision and Pattern Recognition, Chapter 5—Brightness perception and encoding curves; Bertalmio, Marcelo, 2020, Pages 95-129; both of which are hereby incorporated by reference.

A mathematical function for a Visual Blurring Function (VBF) as a function of time. The mathematical function further comprises at least one variable for each of a treatment function for each eye of the viewer, a two-dimensional boundary of a Point of Regard for each eye of the viewer, a distance between at least one eye of the viewer and the two-dimensional boundary of the area of focus for at least one eye of the viewer, and at least one projection.

In some embodiments, at 1920, the method may include rendering a first two-dimensional treatment area in three-dimensional space for each eye of the viewer based at least in part on the mathematical function at time $t_0$. At 1930, the method may include displaying the rendering of the first two-dimensional treatment area in three-dimensional space for each eye of the viewer. At 1940, the method may include determining a visual acuity field for each eye of the viewer in response to the displayed rendering of the first treatment area for each eye of the viewer at time t0. For an exemplary overview of visual acuity, see: Visual Acuity (no date) Wikipedia. Available at: https://en.wikipedia.org/wiki/Visual_acuity (Accessed: Feb. 11, 2023); hereby incorporated by reference.

In some embodiments, at 1950, the method may include comparing the visual acuity performance for each eye of the viewer at time t0 with a historical visual acuity performance for each eye of the viewer. At 1960, the method may include updating the visual blurring function for at least one eye of the viewer if the comparison indicates a change in the visual acuity performance for the at least one eye. In some embodiments, the updating the visual blurring function for at least one eye of the viewer if the comparison may indicate a change in the visual acuity performance for the at least one eye, the change in visual acuity further comprises at least one of an indication of an improvement in visual acuity and a deterioration in visual acuity.

Figure 20:
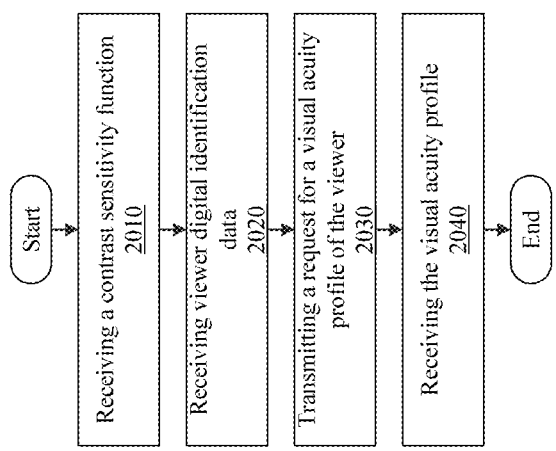
FIG. 20 is a flowchart further illustrating the method for enabling projection of images from FIG. 18, according to some embodiments of the present disclosure.

FIG. 20 is a flowchart that further describes the method for enabling projection of images from FIG. 18, according to some embodiments of the present disclosure. In some embodiments, receiving a visual blurring function of the viewer further comprises, the method may include 1910. In some embodiments, receiving a visual blurring function of the viewer further comprises, the method may include 2020 to 2040. The visual acuity profile may include at least the visual blurring function of the viewer.

Figure 21:
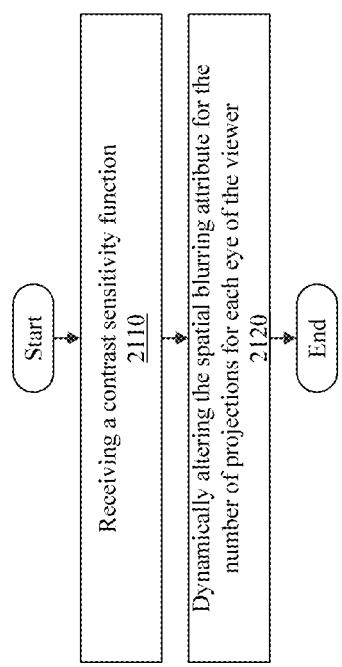
FIG. 21 is a flowchart further illustrating the method for enabling projection of images from FIG. 18, according to some embodiments of the present disclosure.

FIG. 21 is a flowchart that further describes the method for enabling projection of images from FIG. 18, according to some embodiments of the present disclosure. In some embodiments, receiving a visual blurring kernel of the viewer further comprises, the method may include 2110. The contrast sensitivity function (CSF) further may comprise at least one instruction for determining the spatial blurring attribute based at least in part on one or more visual acuity fields of the viewer. In some embodiments, at least one instruction for determining the spatial blurring attribute based at least in part on one or more visual acuity field of the viewer, the one or more visual acuity field further comprises at least one of, the method may include performing one or more additional steps. A foveal visual acuity field. A para-foveal visual acuity field. A peripheral visual acuity field. In some embodiments, displaying the number of projections for each eye of the viewer based on the received visual blurring kernel of the viewer further comprises, the method may include 2120.

Figure 22:
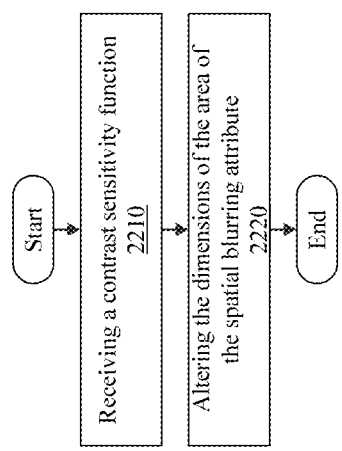
FIG. 22 is a flowchart further illustrating the method for enabling projection of images from FIG. 18, according to some embodiments of the present disclosure.

FIG. 22 is a flowchart that further describes the method for enabling projection of images from FIG. 18, according to some embodiments of the present disclosure. In some embodiments, receiving a visual blurring kernel of the viewer further comprises, the method may include 2110. The contrast sensitivity function (CSF) further may comprise at least one instruction for determining the spatial blurring attribute based at least in part on one or more visual acuity fields of the viewer. In some embodiments, at least one instruction for determining the spatial blurring attribute based at least in part on one or more visual acuity field of the viewer, the one or more visual acuity field further comprises at least one of, the method may include performing one or more additional steps. A foveal visual acuity field. A para-foveal visual acuity field. A peripheral visual acuity field. In some embodiments, Dynamically, in time-space, altering the spatial blurring attribute for the number of projections for each eye of the viewer as a function of time further comprises, the method may include 2220. Altering the dimensions of the area of the spatial blurring attribute to maintain a cognitive load. For examples of measuring cognitive load, see Sweller, J., Ayres, P., Kalyuga, S. (2011). Measuring Cognitive Load. In: Cognitive Load Theory. Explorations in the Learning Sciences, Instructional Systems and Performance Technologies, vol 1. Springer, New York, NY. https://doi.org/10.1007/978-1-4419-8126-4_6; and Stewart Martin (2014) Measuring cognitive load and cognition: metrics for technology-enhanced learning, Educational Research and Evaluation, 20:7-8, 592-621, DOI: 10.1080/13803611.2014.997140; which are hereby incorporated by reference.

Figure 23:
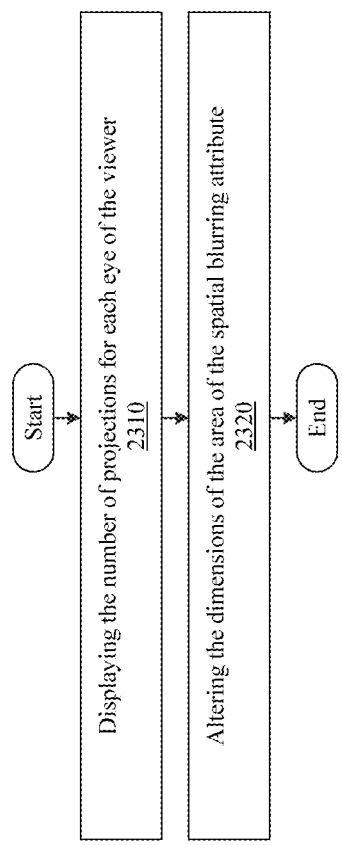
FIG. 23 is a flowchart further illustrating the method for enabling projection of images from FIG. 18, according to some embodiments of the present disclosure.

FIG. 23 is a flowchart that further describes the method for enabling projection of images from FIG. 18, according to some embodiments of the present disclosure. In some embodiments, at 2310, the method may include displaying the number of projections for each eye of the viewer based on the received visual blurring kernel of the viewer. In some embodiments, dynamically altering the spatial blurring attribute for the number of projections for each eye of the viewer as a function of time further comprises, the method may include 2320.

Figure 24:
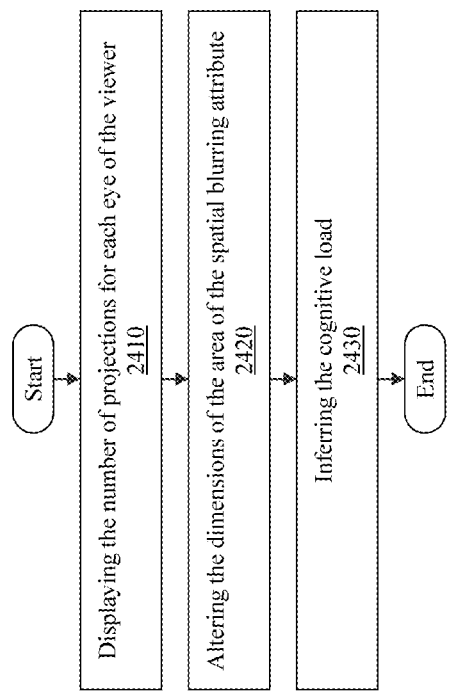
FIG. 24 is a flowchart further illustrating the method for enabling projection of images from FIG. 18, according to some embodiments of the present disclosure.

FIG. 24 is a flowchart that further describes the method for enabling projection of images from FIG. 18, according to some embodiments of the present disclosure. In some embodiments, at 2310, the method may include displaying the number of projections for each eye of the viewer based on the received visual blurring kernel of the viewer. In some embodiments, dynamically altering the spatial blurring attribute for the number of projections for each eye of the viewer as a function of time further comprises, the method may include 2420. In some embodiments, altering the dimensions of the area of the spatial blurring attribute to maintain a cognitive load further comprises, the method may include 2430.

Figure 25:
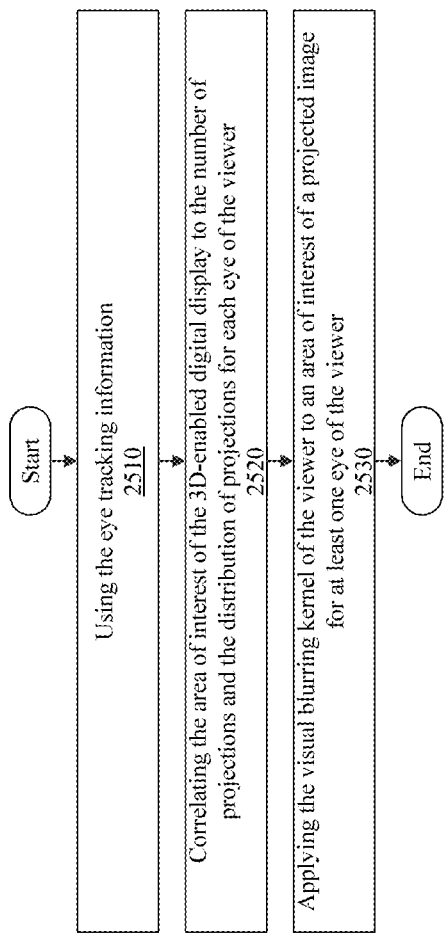
FIG. 25 is a flowchart further illustrating the method for enabling projection of images from FIG. 18, according to some embodiments of the present disclosure.
Figure 26B:
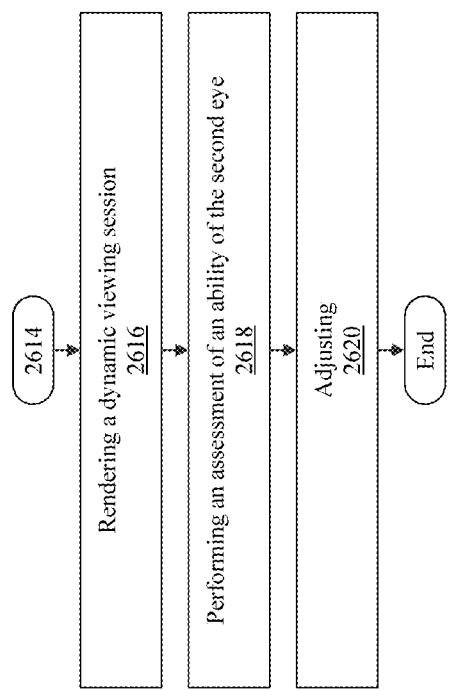
FIG. 26B is a flowchart extending from FIG. 26A and further illustrating the method for enabling projection of images, according to some embodiments of the present disclosure.

FIG. 25 is a flowchart that further describes the method for enabling projection of images from FIG. 18, according to some embodiments of the present disclosure. In some embodiments, determining an image attribute for the number of projections for each eye of the viewer based on the received visual blurring kernel of the viewer further comprises, the method may include 2510 to 2530.

FIGS. 9A to 9B are flowcharts that further describe the method for enabling projection of images from FIG. 18, according to some embodiments of the present disclosure. In some embodiments, at 2602, the method may include using the eye tracking information to determine an area of interest via the point-of-regard of the 3D-enabled digital display. At 2604, the method may include correlating the area of interest of the 3D-enabled digital display to the number of projections and the distribution of projections for each eye of the viewer. At 2606, the method may include applying the visual blurring function of the viewer to an area of interest of a projected image for at least one eye of the viewer. At 2608, the method may include displaying the number of projections for each eye of the viewer based on the received visual blurring function of the viewer. Spatially-adjusting the area of interest of the projected image for the at least one eye.

In some embodiments, at 2610, the method may include rendering a diagnosis of amblyopia based at least in part on the assessment of the ability of the viewer to follow a movement of the at least one object of interest towards the second location and an ability of the viewer to fixate on the at least one object. In some embodiments, the visual blurring function for each of the eyes of the viewer may be associated with the viewer in a digital record, the digital record comprising at least one of, the method may include performing one or more additional steps. A viewer identification, an age-appropriate content for 3D display, an interest appropriate content for 3D display, insurance carrier information, a prescribing medical professional, and an access frequency for administering treatment. In some embodiments, age-appropriate content may include visual media content ratings, such as the television content rating system and movie content rating system.

In some embodiments, the method. At 2612, the method may include receiving a visual blurring function for a second eye of the viewer. At 2614, the method may include determining a gaze direction and the point of regard of the second eye of the viewer with regard to the 3D display. At 2616, the method may include rendering a dynamic viewing session containing at least one object of interest. At 2618, the method may include performing an assessment of an ability of the second eye to follow a movement of the at least one object of interest and an ability of the second eye of the viewer to fixate on the at least one object. At 2620, the method may include adjusting spatially and temporally the at least one object in the rendered dynamic viewing session based at least in part on the assessment. The dynamic viewing session may comprise a plurality of images for projection by the 3D display for the second eye, the rendering based at least in part on the visual blurring function for the second eye, the determined gaze direction and the point of regard of the second eye of the viewer, and the at least one object of interest.

Figure 27:
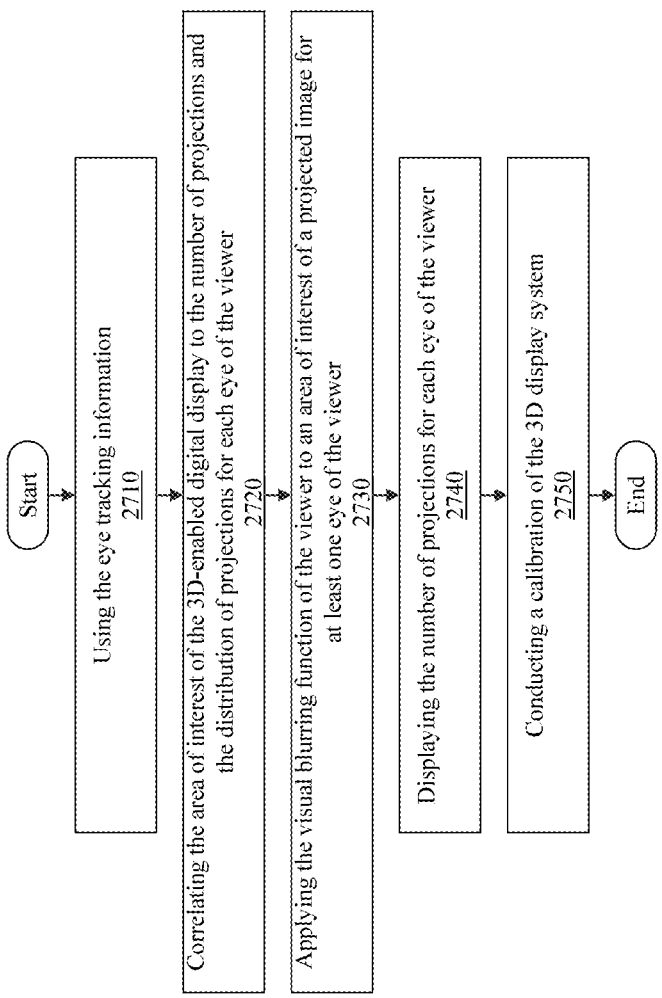
FIG. 27 is a flowchart further illustrating the method for enabling projection of images from FIG. 18, according to some embodiments of the present disclosure.
Figure 28A:
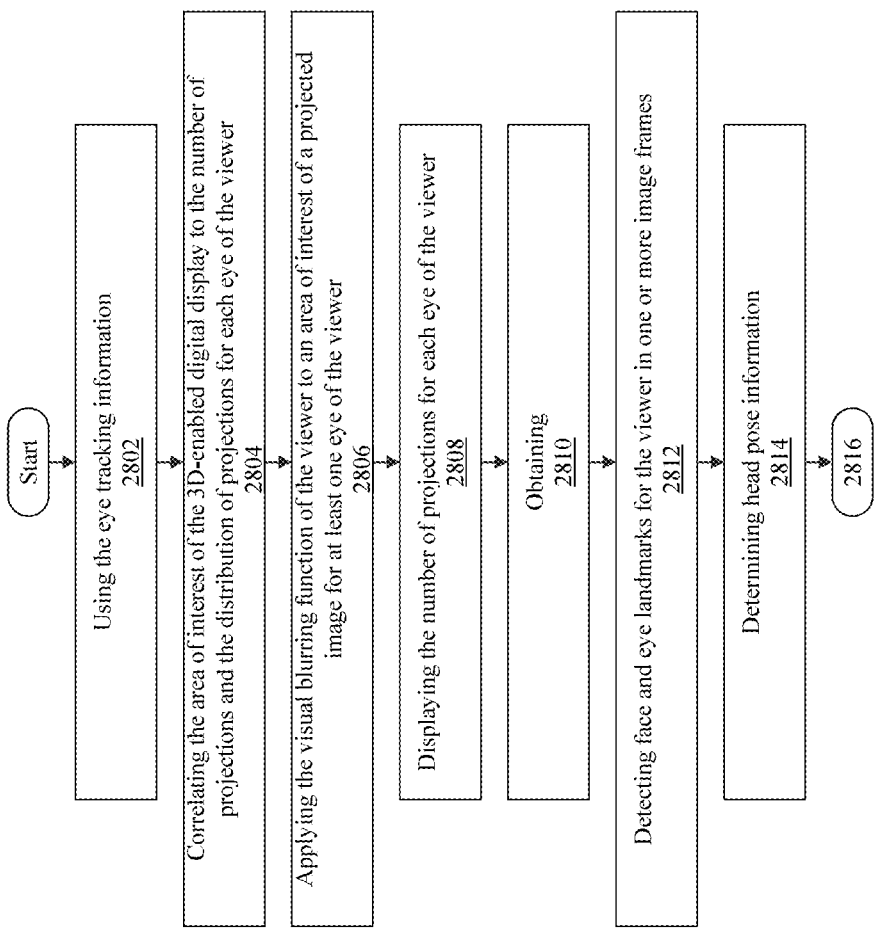
FIG. 28A is a flowchart further illustrating the method for enabling projection of images from FIG. 18, according to some embodiments of the present disclosure.
Figure 28B:
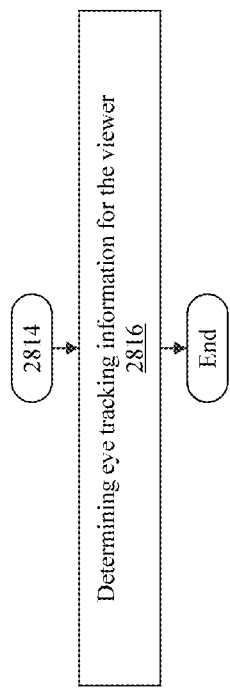
FIG. 28B is a flowchart extending from FIG. 28A and further illustrating the method for enabling projection of images, according to some embodiments of the present disclosure.
Figure 29A:
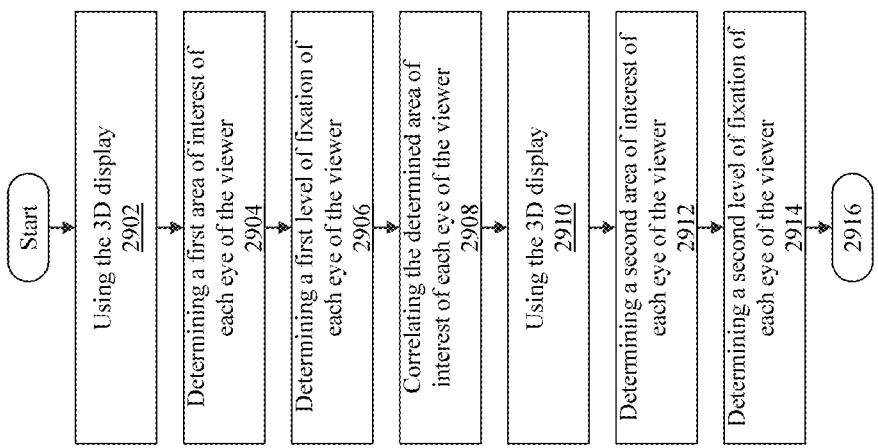
FIG. 29A is a flowchart illustrating a method for assessing a visual acuity of a viewer of a 3D display, according to some embodiments of the present disclosure.
Figure 29B:
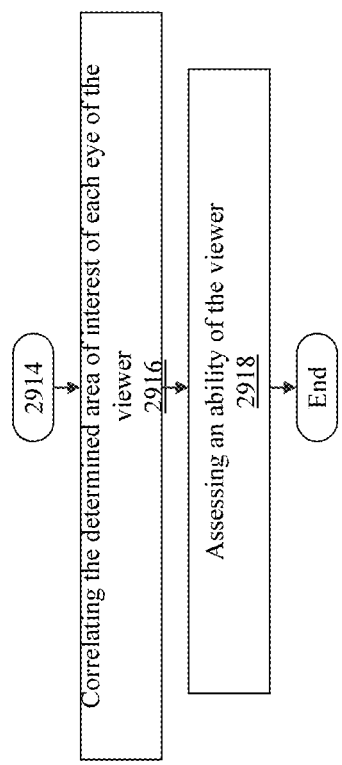
FIG. 29B is a flowchart extending from FIG. 29A and further illustrating the method for assessing a visual acuity of a viewer of a 3D display, according to some embodiments of the present disclosure.

FIG. 27 is a flowchart that further describes the method for enabling projection of images from FIG. 18, according to some embodiments of the present disclosure. In some embodiments, at 2602, the method may include using the eye tracking information to determine an area of interest via the point-of-regard of the 3D-enabled digital display. At 2604, the method may include correlating the area of interest of the 3D-enabled digital display to the number of projections and the distribution of projections for each eye of the viewer. At 2606, the method may include applying the visual blurring function of the viewer to an area of interest of a projected image for at least one eye of the viewer. At 2608, the method may include displaying the number of projections for each eye of the viewer based on the received visual blurring function of the viewer. Spatially-adjusting the area of interest of the projected image for the at least one eye. In some embodiments, the method. At 2750, the method may include conducting a calibration of the 3D display system.

FIGS. 11A to 11B are flowcharts that further describe the method for enabling projection of images from FIG. 18, according to some embodiments of the present disclosure. In some embodiments, at 2602, the method may include using the eye tracking information to determine an area of interest via the point-of-regard of the 3D-enabled digital display. At 2604, the method may include correlating the area of interest of the 3D-enabled digital display to the number of projections and the distribution of projections for each eye of the viewer. At 2606, the method may include applying the visual blurring function of the viewer to an area of interest of a projected image for at least one eye of the viewer. At 2608, the method may include displaying the number of projections for each eye of the viewer based on the received visual blurring function of the viewer. Spatially-adjusting the area of interest of the projected image for at least one eye. In some embodiments, conducting a calibration of the 3D display further comprises, the method may include 2810 to 2816. A point of regard (POR) of each eye of the viewer. Eye state of each eye of the viewer. Gaze direction of each eye of the viewer. Eye region illumination information for each eye of the viewer. A position of each eye of the viewer relative to the 3D-enabled digital display.

FIGS. 12A to 12B are flowcharts that describe a method for assessing a visual acuity of a viewer of a 3D display, according to some embodiments of the present disclosure. In some embodiments, at 2902, the method may include using the 3D display to project a first sequence of images in three-dimensional space containing at least one object of interest. At 2904, the method may include determining a first area of interest of each eye of the viewer via a point of regard. At 2906, the method may include determining a first level of fixation of each eye of the viewer. At 2908, the method may include correlating the determined area of interest of each eye of the viewer with the determined fixation of each eye of the viewer.

In some embodiments, at 2910, the method may include using the 3D display to project a second sequence of image in three-dimensional space containing at least one object of interest in a second location. At 2912, the method may include determining a second area of interest of each eye of the viewer. At 2914, the method may include determining a second level of fixation of each eye of the viewer. At 2916, the method may include correlating the determined area of interest of each eye of the viewer with the determined second area of fixation of each eye of the viewer. At 2918, the method may include assessing an ability of the viewer to follow a movement of the at least one object of interest towards the second location and an ability of the viewer to fixate on the at least one object.

In some embodiments, the method may include prescribing a prescription for a treatment of amblyopia using a 3D display. The prescription further comprises, the method may include performing one or more additional steps. A visual blurring function for each of the eyes of the viewer. A desired performance to fixate on an object of interest. A desired ability of the viewer to follow a movement of the object of interest.

Figure 30:
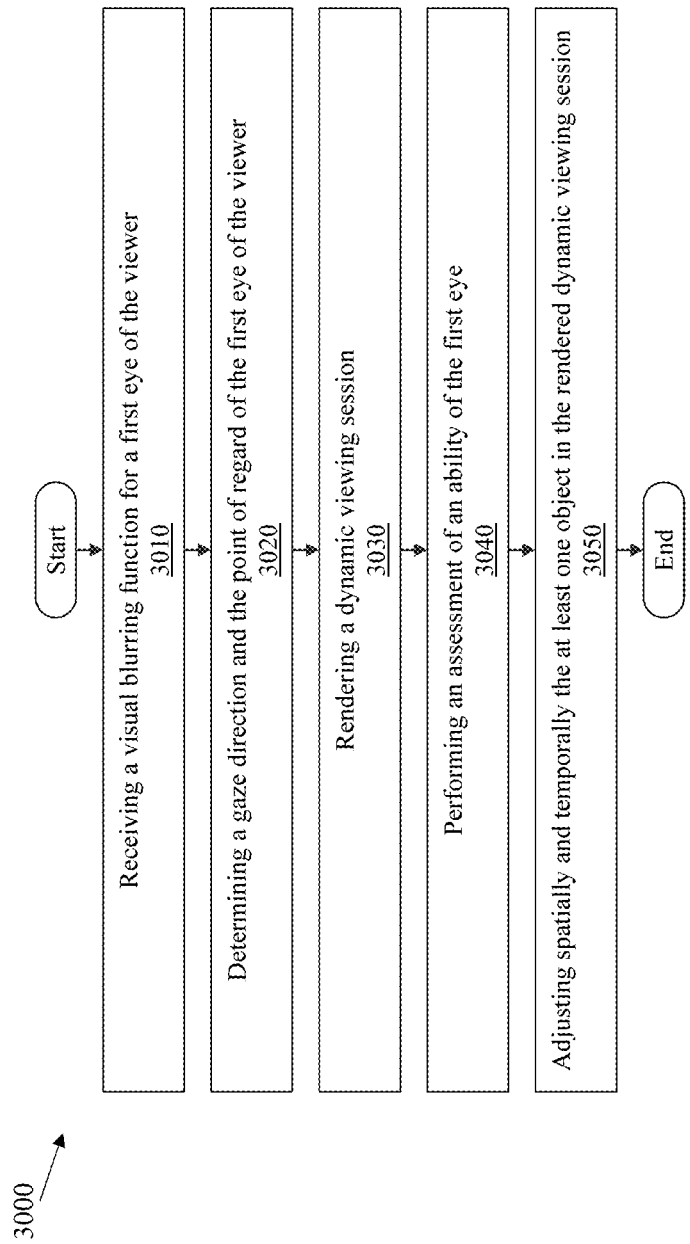
FIG. 30 is a flowchart illustrating a method for treating amblyopia in a user, according to some embodiments of the present disclosure.

FIG. 30 is an exemplary 3000 system diagram and information flow that depicts a method for treating amblyopia in a user, according to some embodiments of the present disclosure. In some embodiments, at 3010, the method may include receiving a visual blurring function for a first eye of the viewer. In some embodiments, the blurring function may be stored in memory on a remote server and transmitted to the system 3000 upon verification of the viewer's identity. At 3020, the method may include determining a gaze direction and the point of regard of the first eye of the viewer with regard to the 3D display. In some embodiments, the system may include one or more cameras directed towards the user to determine a gaze direction of the viewer. Processing the gaze direction may be determined by processing a video feed from the system 3000 cameras by a local CPU or GPU. In an alternative embodiment, the camera system may be a dedicated gaze detection system in communication with a display, such as a 3D display.

At 3030, the method may include rendering a dynamic viewing session containing at least one object of interest. In some embodiments, rendering may include receiving a video feed comprising a series of projections that make up the three-dimensional image displayed to the viewer. The received visual blurring function and the determined gaze direction and the point of regard of the first eye of the viewer 3020 may be used to apply the blurring function for the first eye of the viewer 3020 to render a dynamic viewing session of an object of interest 3030. In some embodiments, the dynamic nature of the viewing session may refer to the application of the blurring function, varying the impacted two-dimensional area of the blurred pixels of the projection such that the area may increase, decrease, or cease presenting an area of blurred images in the gaze direction of the first eye.

At 3040, the method may include performing an assessment of an ability of the first eye to follow a movement of the at least one object of interest and an ability of the first eye of the viewer to fixate on the at least one object. In some embodiments, an assessment may comprise varying the impacted two-dimensional area of the blurred pixels of the projection and monitoring the weak eye's ability to track the object of interest within the projected images. The area of the impacted two-dimensional area may increase, decrease, or cease presenting an area of blurred images in the gaze direction of the first eye. In some embodiments, the shape of the two-dimensional surface may be varied, for example blurring images between two or more of a circular, rectangular, or irregular shape and assessing the viewer's ability to fixate on the object of interest within the foveal or paraoveal area of interest. In some embodiments, the blurring function may dynamically alter based on the performance of the viewer. For example, an impacted two-dimensional area of the blurred pixels of the projection when an analysis of the viewer's performance indicates the viewer's amblyopia condition improves when the impacted two-dimensional area is increased for a portion of the viewing experience.

At 3050, the method may include adjusting spatially and temporally the at least one object in the rendered dynamic viewing session based at least in part on the assessment. The dynamic viewing session may comprise a plurality of images for projection by the 3D display for the first eye, the rendering based at least in part on the visual blurring function for the first eye, the determined gaze direction and the point of regard of the first eye of the viewer, and the at least one object of interest. While steps 3010 through 3050 are shown sequentially, in some embodiments the steps may be interchangeable. For example, steps 3020 and 3010 are interchangeable prior to step 3030.

Figure 31:
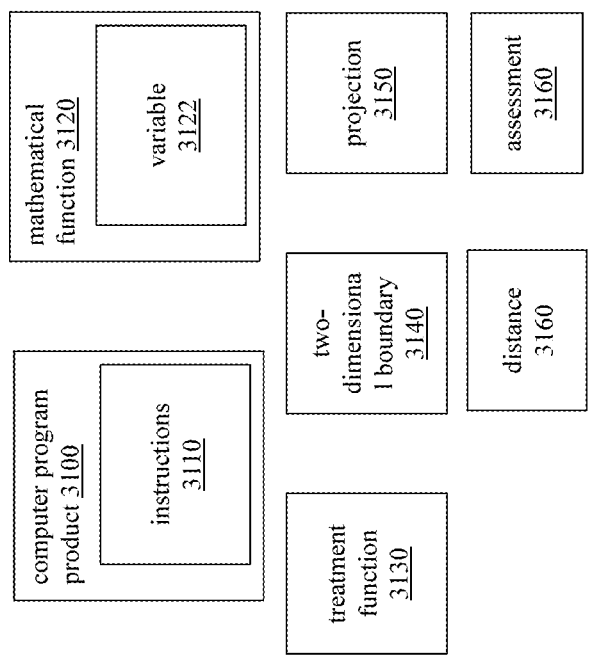
FIG. 31 is a block diagram illustrating a computer program product, according to some embodiments of the present disclosure.

FIG. 31 is a block diagram that describes a computer program product 3100, according to some embodiments of the present disclosure. In some embodiments, the computer program product 3100 may also include instructions 3110 which, when executed by a computer, cause the computer to carry out steps related to the diagnosis, development of an amblyopic eye profile of the viewer, and an amblyopic treatment regimen.

In some embodiments, instructions 3110 may include:
Obtaining face image data and eye region image data for a viewer within a field of view of at least one camera in proximity to a 3D-enabled digital display.
Obtaining a distance between the viewer and the 3D-enabled digital display.
Determining a point of regard of the viewer of the 3D-enabled digital display.
Associating the point of regard of the viewer of the 3D-enabled digital display with a region of media displayed by the 3D-enabled digital display.
Applying a visual blurring function associated with at least one eye of the viewer to at least a portion of the region of media displayed by the 3D-enabled digital display.
Receiving a visual blurring function of the viewer.

In some embodiments, instructions 3110 may include receiving a contrast sensitivity function (CSF) indicative of a visual acuity field of the viewer. The receiving instruction in some embodiments is proceeded by an instruction set for receiving viewer digital identification data indicative of the viewer. In some embodiments, the computer program product 3100 may include instructions 3110 for transmitting a request for a visual acuity profile of the viewer when the visual acuity profile of the viewer has not been received. Such transmitting instructions may be followed by receiving the visual acuity profile of the viewer. In some embodiments, the visual blurring function of the viewer may be received with additional information of the viewer. For example, viewer preferences, viewer information, previous assessments, and viewer identification information may be received to create a custom experience for the viewer.

In some embodiments, instructions 3110 may also include instructions for displaying the number of projections for each eye of the viewer based on the received visual blurring kernel of the viewer. In some embodiments, instructions 3110 include determining an image attribute for the number of projections for each eye of the viewer based on the received visual blurring kernel of the viewer. In some embodiments, instructions 3110 include determining an image attribute for the number of projections for each eye of the viewer based on the received visual blurring kernel of the viewer. Instructions 3110 in certain embodiments include steps for using the eye tracking information to determine an area of interest of the 3D-enabled digital display. Instructions 3110 may also include correlating the area of interest of the 3D-enabled digital display to the number of projections and the distribution of projections for each eye of the viewer and applying the visual blurring kernel of the viewer to an area of interest of a projected image for at least one eye of the viewer. In some embodiments, the computer program product 3100 may further include instructions 3110 for applying the visual blurring function of the viewer to an area of interest of a projected image for the at least one eye of the viewer and/or spatially-adjusting the area of interest of the projected image for the at least one eye.

In some embodiments, receiving a visual blurring function of the viewer. In some embodiments, instructions 3110 for a contrast sensitivity function (CSF) indicative of a visual acuity of the viewer may be augmented with a mathematical function 3120. The mathematical function 3120 may include at least one variable 3122 for each of a treatment function 3130 for each eye of the viewer, a two-dimensional boundary 3140 of a Point of Regard (PoR) for each eye of the viewer, a distance 3160 between at least one eye of the viewer and the two-dimensional boundary of the area of focus for at least one eye of the viewer, and at least one projection 3150, the projection 3150 containing information for displaying a projection with a 3D display. In some embodiments, rendering may include a first two-dimensional treatment area in three-dimensional space for each eye of the viewer based at least in part on the mathematical function 3120 at time $t_0$. In some embodiments, displaying the number of projections for each eye of the viewer can be based on the received visual blurring kernel of the viewer. Dynamically altering the spatial blurring attribute for the number of projections for each eye of the viewer may be altered as a function of time. In some embodiments, dynamically altering the spatial blurring attribute for the number of projections for each eye of the viewer as a function of time. In some embodiments, altering the dimensions of the area of the spatial blurring attribute may be done within the foveal visual acuity field of an eye of the viewer as a sinusoidal function of time.

In some embodiments, the computer program product 3100 may include instructions for performing an assessment 3160 of the viewer's performance while interacting with the 3D display. An assessment 3160 may include comparing the visual acuity performance for each eye of the viewer at time $t_0$ with a historical visual acuity performance for each eye of the viewer. Upon completion of the comparison, the assessment 3160 may include instructions for updating the visual blurring function for at least one eye of the viewer if the comparison may indicate a change in the visual acuity performance for the at least one eye. In some embodiments, the updating the visual blurring function for at least one eye of the viewer if the comparison may indicate a change in the visual acuity performance for the at least one eye, the change in visual acuity. At least one of an indication of an improvement in visual acuity and a deterioration in visual acuity.

In some embodiments, the projection 3150 may include steps displaying the number of projections for each eye of the viewer based on the received visual blurring kernel of the viewer. The visual blurring kernel may further include instructions for dynamically altering the spatial blurring attribute for the number of projections for each eye of the viewer as a function of time. In some embodiments, dynamically altering the spatial blurring attribute for the number of projections for each eye of the viewer as a function of time. In a still further embodiment, the dynamically altering the spatial blurring attribute may include altering the dimensions of the area of the spatial blurring attribute within the foveal visual acuity field of an eye of the viewer and/or to maintain a cognitive load.

In some embodiments, altering the dimensions of the area of the spatial blurring attribute to maintain a cognitive load. Inferring the cognitive load from the eye tracking information. In some embodiments, determining a count of projections and a three-dimensional distribution of the projections for each eye of the viewer based on the eye tracking information. Determining the count of projections based at least in part on one or more of a refresh rate of the 3D-enabled digital display, a defined segment of video, a sampling rate of at least one camera of the 3D-enabled digital display, and the visual blurring function for each eye of the viewer.

Figure 32A:
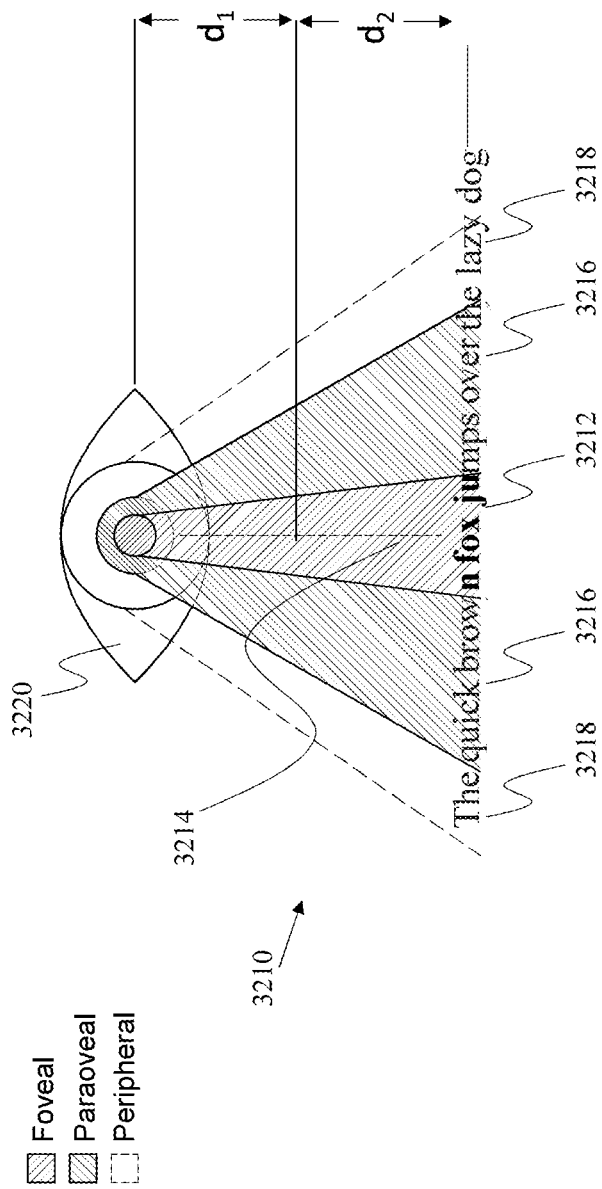
FIG. 32A is an image depicting the foveal, paraoveal, and peripheral field of views, each at different distances $d_n$, according to some embodiments of the present disclosure.

FIG. 32A is a schematic diagram depicting a visual acuity field 3210 within the point of regard of a viewer's eye 3220. As displayed, the visual acuity field 3210 includes three regions. The first region, the foveal region 3212 is a region where the visual acuity of the eye is greatest. The foveal region 3212 is generally the volume defined by a 2 degree ray as measured from a center line 3214 from the viewer's eye 3220. The visual acuity of the viewer's eye 3220 decreases further within the paraoveal field of view 3216 as compared to the visual acuity within the foveal field of view 3212. The paraoveal field of view 3216 extends about 5 degrees from the centre, while the peripheral field of view 3218 extends nearly 90 degrees. The area within the field of view corresponding to a region depends on how far the object of interest is away from the viewer eye 3220. For example, the area within the field of view increases from the area at $d_1$ to the area within the field of view at $d_2$. The area of focus varies as the square of the distance. For example, the area divided by the square of the distance is constant, and is called the solid angle. In some embodiments, the solid angle may be measured in units of steradians (sr). The foveal region has a 3.8 millisteradian (msr) solid angle, the foveal plus parafoveal regions comprise 24 msr, and the foveal, parafoveal plus peripheral regions have a $2\pi$ sr solid angle.

Figure 32B:
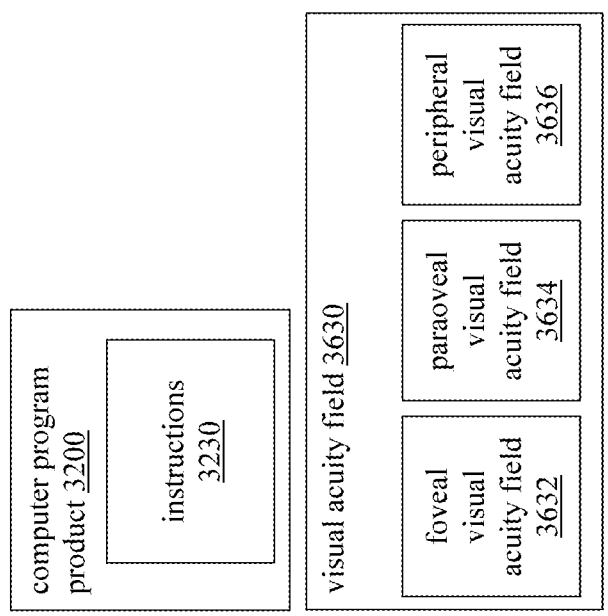
FIG. 32B is a block diagram further illustrating the computer program product from FIG. 31, according to some embodiments of the present disclosure.

The regions of visual acuity may be incorporated into the computer program product 3100 from FIG. 31. Referring now to FIG. 32B, a block diagram of the computer program product 3200 is depicted. In some embodiments, the computer program product includes instructions 3230 for using a 3D display and associated peripheral devices (e.g., a keyboard, cameras, network attached storage, media player) for the diagnosis and/or treatment of myopia of a viewer. Instruction 3230 may include steps for the receiving a visual blurring kernel of the viewer. In some embodiments, the visual blurring kernel may include instructions for receiving a contrast sensitivity function (CSF). The contrast sensitivity function (CSF) may include at least one instruction for determining the spatial blurring attribute based at least in part on one or more visual acuity fields 3630 of the viewer. The one or more visual acuity field 3630 may include a foveal visual acuity field 3632, a paraoveal visual acuity field 3634, and a peripheral visual acuity field 3636.

In some embodiments, the eye region image data may include at least one of pupil image data, iris image data, or eyeball image data. In some embodiments, the at least one gaze angle may include at least one of yaw or pitch. In some embodiments, the analyzing the eye region image data further may include analyzing at least one eye state characteristic. In some embodiments, the eye state characteristic may include at least one of a blink, an open state, or a closed state. Open states may be further characterized as dwells or fixations, or saccades (periods of movement of the eye from one point to another point).

In some embodiments, the acquiring eye region image data may be performed by a camera at a distance of at least 0.2 meters from the plurality of viewers. In some embodiments, the acquiring eye region image data may be performed by at least one of a laptop camera, tablet camera, a smartphone camera, or a digital external camera (e.g., a camera associated with a digital billboard or retail display designed for viewing by multiple people. In some embodiments, the acquiring eye region image data may be performed with or without active illumination.

In some embodiments, the analyzing the eye region image data to determine at least one 3D eye position, at least one gaze angle, and at least one point-of-regard for at least one viewer relative to at least one camera associated with the 3D-enabled digital display may include mapping the eye region image data to a Cartesian coordinate system. Embodiments may also include unprojecting the pupil and limbus of both eyeballs onto the Cartesian coordinate system to give 3D contours of each eyeball.

In some embodiments, the method further includes detecting degradation in the eye region image data. Embodiments may also include switching to a different camera having better eye region image data based on the detection of degradation in the eye region image data. In some embodiments, the method further includes analyzing the eye region image data for at least one of engagement with the 3D-enabled digital display, fixation, or saccade. In some embodiments, the method further includes assigning a unique digital identifier to each viewer's face. In some embodiments, the unique digital identifier may be associated with at least one sequence of image projections calculated for each viewer. In this way each viewer can be shown a sequence of 3D images that is appropriate to their position relative to the camera(s), and the system can process image input and perform projection rendering accordingly for each specific viewer.

Embodiments of the present disclosure may also include a method for projecting multi-viewer-specific 3D object perspectives from a single 3D display, the method including selecting at least two viewers based on at least one property of a 3D display (e.g., resolution, size, single viewer or multi-viewer) or at least one eye property of the at least two viewers. Embodiments may also include assigning at least one camera to at least one viewer based on an assessment of which camera among a plurality of cameras has the best viewing angle and imaging conditions of an eye region of the at least one viewer.

Embodiments may also include acquiring eye region image data of a plurality of viewers within a field of view of at least one camera associated with a 3D-enabled digital display. Embodiments may also include analyzing the eye region image data to determine at least one 3D eye position, at least one gaze angle, at least one point-of-regard, and at least one eye state for at least one viewer relative to at least one camera associated with the 3D-enabled digital display.

Embodiments may also include calculating a distance from at least one camera and at least one viewer using image analysis. Embodiments may also include calculating a plurality of image projections for display by the single 3D display. In some embodiments, at least one of the plurality of projections may be calculated to be appropriate for each viewer's position and point-of-regard with respect to the 3D-enabled digital display. Embodiments may also include rendering the plurality of image projections on the single 3D display.

Another aspect of the present disclosure relates to a system configured for projecting multi-viewer-specific 3D object perspectives from a single 3D display. The system may include one or more hardware processors configured by machine-readable instructions. The processor(s) may be configured to acquire eye region image data of a plurality of viewers within a field of view of at least one camera associated with a 3D-enabled digital display. The processor(s) may be configured to analyze the eye region image data to determine at least one 3D eye position, at least one gaze angle, and at least one point-of-regard for at least one viewer relative to at least one camera associated with the 3D-enabled digital display. The processor(s) may be configured to calculate a plurality of image projections for display by the single 3D display. At least one of the plurality of projections may be calculated to be appropriate for each viewer's position and point-of-regard with respect to the 3D-enabled digital display.

Yet another aspect of the present disclosure relates to a non-transient computer-readable storage medium having instructions embodied thereon, the instructions being executable by one or more processors to perform a method for projecting multi-viewer-specific 3D object perspectives from a single 3D display. The method may include acquiring eye region image data of a plurality of viewers within a field of view of at least one camera associated with a 3D-enabled digital display. The method may include analyzing the eye region image data to determine at least one 3D eye position, at least one gaze angle, and at least one point-of-regard for at least one viewer relative to at least one camera associated with the 3D-enabled digital display. The method may include calculating a plurality of image projections for display by the single 3D display. At least one of the plurality of projections may be calculated to be appropriate for each viewer's position and point-of-regard with respect to the 3D-enabled digital display.

Still another aspect of the present disclosure relates to a system configured for projecting multi-viewer-specific 3D object perspectives from a single 3D display. The system may include means for acquiring eye region image data of a plurality of viewers within a field of view of at least one camera associated with a 3D-enabled digital display. The system may include means for analyzing the eye region image data to determine at least one 3D eye position, at least one gaze angle, and at least one point-of-regard for at least one viewer relative to at least one camera associated with the 3D-enabled digital display. The system may include means for calculating a plurality of image projections for display by the single 3D display. At least one of the plurality of projections may be calculated to be appropriate for each viewer's position and point-of-regard with respect to the 3D-enabled digital display.

Figure 33:
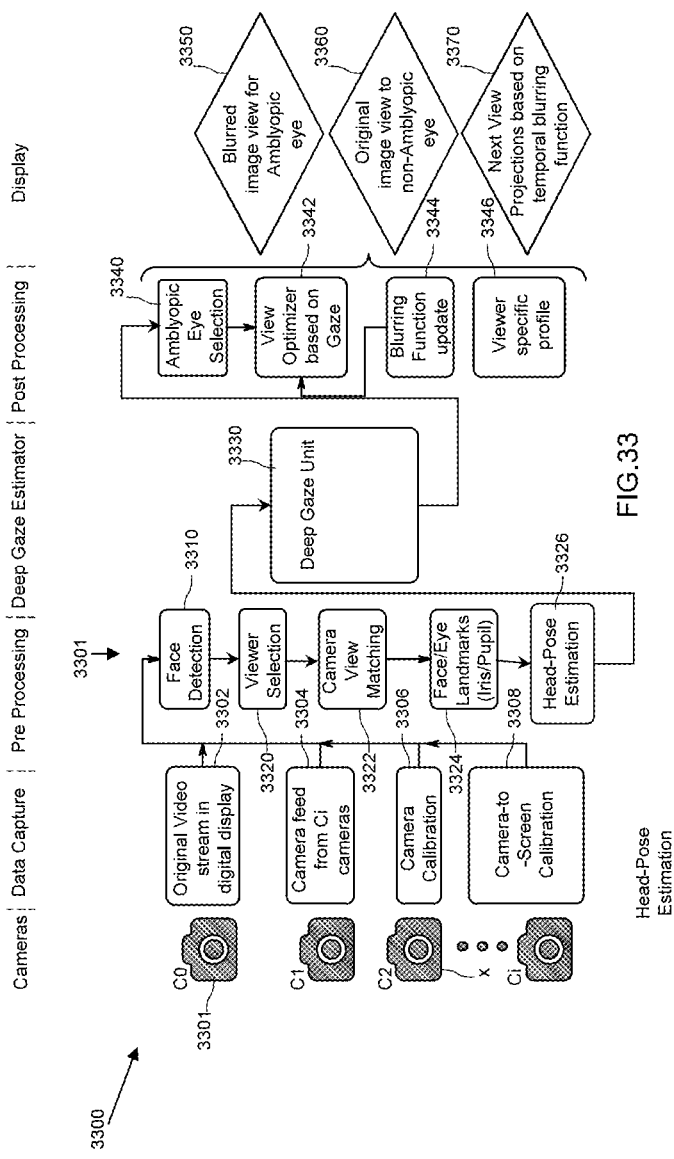
FIG. 33 is an exemplary system and processing flow to present two images on a 3D display for the treatment of amblyopia.

Referring now to FIG. 33, an exemplary system flow 3300 is depicted. The system flow 3300 may accept image data from the camera feed 3304 from cameras 3301 (e.g., $C_0$, $C_1$, $C_2 \ldots C_i$). One or more cameras 3301 may support a camera calibration flow 3306. The camera calibration flow 3306 may include image data that can be used to identify the viewer within the field of view, a distance of the user to the camera, a sensor check of the image sensor (e.g., the camera 3301 CMOS sensor), or a system control check to send and receive instructions to and from the cameras 3301. A camera-to-screen calibration 3308 may also be performed to calibrate the six degrees of freedom between the camera and 3D display. The image data from camera feeds 3304 are processed to determine facial features of the viewer at face detection 3310 of the image data pre-processing flow.

In some embodiments, additional image data pre-processing steps may be conducted to reduce the data processing burden of the CPU and/or GPU of the deep gaze unit 3330. A graphical user interface may be used to support a viewer selection 3320 to initiate an amblyopia treatment session. In some embodiments, recognition of one or more of face/eye landmarks 3324 may support a matching function of previous viewers with the viewer in the field of view of the cameras 3301. Additional image data processing across multiple cameras 3301 may be used to match views within each of the camera field of views. Image data processing may also be performed to identify facial landmarks 3324 and head-pose estimation 3326.

In some embodiments, the deep gaze unit 3330 may support key functions in the treatment of amblyopia including determining eye localization, eye state, fixation, saccade, and gaze estimation. Post processing steps 3340, 3342, 3344, and 3346 may collectively be used to apply a blurring function to the original video stream 3302 to provide a amblyopia treatment that is customized to the individual viewer. In some embodiments, the amblyopic eye is selected based on the loaded viewer specific profile 3346. The blurring function will be applied to the pixels correlated with the viewer's point-of-regard. In some embodiments, as the treatment progresses, a blurring function update 3344 may be implemented.

In some embodiments, the updated image view is displayed with a blurred image view for the amblyopic eye 3350 and an original image view to the non-amblyopic eye 3360. The display functions may also receive the next view projections based on the temporal blurring function 3370.

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having ordinary skill in the art will recognize that the state of the art has progressed to the point where there is little distinction left between hardware, software, and/or firmware implementations of aspects of systems; the use of hardware, software, and/or firmware is generally a design choice representing cost vs. efficiency tradeoffs (but not always, in that in certain contexts the choice between hardware and software can become significant). Those having ordinary skill in the art will appreciate that there are various vehicles by which processes and/or systems and/or other technologies described herein can be affected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be affected, none of which is inherently superior to the other in that any vehicle to be utilized is a choice dependent upon the context in which the vehicle will be deployed and the specific concerns (e.g., speed, flexibility, or predictability) of the implementer, any of which may vary.

In some implementations described herein, logic and similar implementations may include software or other control structures suitable to operation. Electronic circuitry, for example, may manifest one or more paths of electrical current constructed and arranged to implement various logic functions as described herein. In some implementations, one or more medias are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively, or additionally, in some variants, an implementation may include special-purpose hardware, software, firmware components, and/or general-purpose components executing or otherwise controlling special-purpose components. Specifications or other implementations may be transmitted by one or more instances of tangible or transitory transmission media as described herein, optionally by packet transmission or otherwise by passing through distributed media at various times.

Alternatively, or additionally, implementations may include executing a special-purpose instruction sequence or otherwise operating circuitry for enabling, triggering, coordinating, requesting, or otherwise causing one or more occurrences of any functional operations described above. In some variants, operational or other logical descriptions herein may be expressed directly as source code and compiled or otherwise expressed as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar modes of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those having ordinary skill in the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a USB drive, a solid state memory device, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read-only, etc.)), and/or electrical circuitry forming a communications device (e.g., a modem, communications switch, optical-electrical equipment, etc.). Those having ordinary skill in the art will recognize that the subject matter described herein may be implemented in an analog or digital fashion or some combination thereof.

Those skilled in the art will recognize that at least a portion of the devices and/or processes described herein can be integrated into a data processing system. Those having ordinary skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

In certain cases, use of a system or method as disclosed and claimed herein may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

One skilled in the art will recognize that the herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific example is intended to be representative of its class, and the non-inclusion of specific components (e.g., operations), devices, and objects should not be taken to be limiting.

With respect to the use of substantially any plural and/or singular terms herein, those having ordinary skill in the art can translate from the plural to the singular or from the singular to the plural as is appropriate to the context or application. The various singular/plural permutations are not expressly set forth herein for sake of clarity.

The herein described subject matter sometimes illustrates different components contained within, or connected with, different other components. It is to be understood that such depicted architectures are presented merely as examples, and that in fact many other architectures may be implemented which achieve the same functionality. In a conceptual sense, any arrangement of components to achieve the same functionality is effectively "associated" such that the desired functionality is achieved. Therefore, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of "operably couplable" include but are not limited to physically mateable or physically interacting components, wirelessly interactable components, wirelessly interacting components, logically interacting components, or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components, inactive-state components, or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such a recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having ordinary skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having ordinary skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented as sequences of operations, it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for enabling projection of images from a 3D digital display, the method comprising:
   obtaining face image data and eye region image data for a viewer within a field of view of at least one camera in proximity to a 3D-enabled digital display;
   detecting face and eye landmarks for the viewer in one or more image frames based on the face image data;
   determining head pose information based on the face image data and eye region image data;
   determining eye tracking information for the viewer based on the face image data, eye region image data, and head pose information, the eye tracking information including:
   a) a point of regard (POR) of each eye of the viewer;
   b) eye state of each eye of the viewer;
   c) gaze direction of each eye of the viewer;
   d) eye region illumination information for each eye of the viewer; and
   e) a position of each eye of the viewer relative to the 3D-enabled digital display;
   receiving a visual blurring function for each eye of the viewer;
   determining a count of projections and a three-dimensional distribution of the projections for each eye of the viewer based on the eye tracking information; and
   determining a spatial blurring attribute for the number of projections for each eye of the viewer based at least in part on the received visual blurring function of the viewer.

2. The method of claim 1, wherein receiving a visual blurring function of the viewer further comprises:
   receiving a contrast sensitivity function (CSF) indicative of a visual acuity field of the viewer.

3. The method of claim 2, wherein a contrast sensitivity function (CSF) indicative of a visual acuity of the viewer further comprises:
   data indicative of a performance of a contrast function sensitivity performance.

4. The method of claim 2, wherein a contrast sensitivity function (CSF) indicative of a visual acuity of the viewer further comprises:
   a mathematical function for a Visual Blurring Function (VBF) as a function of time, wherein the mathematical function further comprises at least one variable for each of:
   a. a treatment function for each eye of the viewer;
   b. a two-dimensional boundary of a Point of Regard for each eye of the viewer;
   c. a distance between at least one eye of the viewer and the two-dimensional boundary of the area of focus for at least one eye of the viewer; and
   d. at least one projection.

5. The method of claim 4, further comprises:
   a. rendering a first two-dimensional treatment area in three-dimensional space for each eye of the viewer based at least in part on the mathematical function at time $t_0$;
   b. displaying the rendering of the first two-dimensional treatment area in three-dimensional space for each eye of the viewer;
   c. determining a visual acuity field for each eye of the viewer in response to the displayed rendering of the first treatment area for each eye of the viewer at time $t_0$.

6. The method of claim 5, further comprising:
   a. comparing the visual acuity performance for each eye of the viewer at time $t_0$ with a historical visual acuity performance for each eye of the viewer; and
   b. updating the visual blurring function for at least one eye of the viewer if the comparison indicates a change in the visual acuity performance for the at least one eye.

7. The method of claim 6, wherein the updating the visual blurring function for at least one eye of the viewer if the comparison indicates a change in the visual acuity performance for the at least one eye, the change in visual acuity further comprises at least one of an indication of an improvement in visual acuity and a deterioration in visual acuity.

8. The method of claim 2, wherein a contrast sensitivity function (CSF) indicative of a visual acuity of the viewer further comprises:
   data indicative of a performance of a spatial frequency sensitivity performance.

9. The method of claim 2, wherein a contrast sensitivity function (CSF) indicative of a visual acuity of the viewer further comprises:
   a function indicative of a visual acuity performance of the user at a distance from the 3D-enabled digital display and its minimal Spatial Frequency Threshold for a trackable object on the digital display.

10. The method of claim 2, wherein receiving a visual blurring function of the viewer further comprises:
    receiving viewer digital identification data indicative of the viewer;
    transmitting a request for a visual acuity profile of the viewer;
    receiving the visual acuity profile wherein the visual acuity profile includes at least the visual blurring function of the viewer.

11. The method of claim 1, wherein receiving the visual acuity profile further comprises an amblyopic eye classification for each eye of the viewer.

12. The method of claim 1, wherein receiving a visual blurring kernel of the viewer further comprises:
    receiving a contrast sensitivity function (CSF), wherein the contrast sensitivity function (CSF) further comprises at least one instruction for determining the spatial blurring attribute based at least in part on one or more visual acuity fields of the viewer.

13. The method of claim 12, wherein at least one instruction for determining the spatial blurring attribute based at least in part on one or more visual acuity field of the viewer, the one or more visual acuity field further comprises at least one of:

a foveal visual acuity field;
a parafoveal visual acuity field; and
a peripheral visual acuity field.

14. The method of claim 13, wherein displaying the number of projections for each eye of the viewer based on the received visual blurring kernel of the viewer further comprises:
dynamically altering the spatial blurring attribute for the number of projections for each eye of the viewer as a function of time.

15. The method of claim 13, wherein dynamically altering the spatial blurring attribute for the number of projections for each eye of the viewer as a function of time further comprises:
altering the dimensions of the area of the spatial blurring attribute within the foveal visual acuity field of an eye of the viewer, wherein altering the dimensions of the area of the spatial blurring attribute to maintain a cognitive load.

16. The method of claim 1, further comprising:
displaying the number of projections for each eye of the viewer based on the received visual blurring kernel of the viewer.

17. The method of claim 16, wherein dynamically altering the spatial blurring attribute for the number of projections for each eye of the viewer as a function of time further comprises:
altering the dimensions of the area of the spatial blurring attribute within the foveal visual acuity field of an eye of the viewer as a function of time.

18. The method of claim 16, wherein dynamically altering the spatial blurring attribute for the number of projections for each eye of the viewer as a function of time further comprises:
altering the dimensions of the area of the spatial blurring attribute within the foveal visual acuity field of an eye of the viewer as a sinusoidal function of time.

19. The method of claim 18, wherein altering the dimensions of the area of the spatial blurring attribute to maintain a cognitive load further comprises:
inferring the cognitive load from the eye tracking information.

20. The method of claim 1, wherein determining a count of projections and a three-dimensional distribution of the projections for each eye of the viewer based on the eye tracking information further comprises:
determining the count of projections based at least in part on one or more of a refresh rate of the 3D-enabled digital display, a defined segment of video, a sampling rate of at least one camera of the 3D-enabled digital display, and the visual blurring function for each eye of the viewer.

21. The method of claim 1, wherein determining an image attribute for the number of projections for each eye of the viewer based on the received visual blurring kernel of the viewer further comprises:
using the eye tracking information to determine an area of interest of the 3D-enabled digital display;
correlating the area of interest of the 3D-enabled digital display to the number of projections and the distribution of projections for each eye of the viewer;
applying the visual blurring kernel of the viewer to an area of interest of a projected image for at least one eye of the viewer.

22. The method of claim 1, wherein applying the visual blurring function of the viewer to an area of interest of a projected image for the at least one eye of the viewer further comprises:
spatially-adjusting the area of interest of the projected image for the at least one eye.

23. The method of claim 1, further comprising:
using the eye tracking information to determine an area of interest via the point-of-regard of the 3D-enabled digital display;
correlating the area of interest of the 3D-enabled digital display to the number of projections and the distribution of projections for each eye of the viewer;
applying the visual blurring function of the viewer to an area of interest of a projected image for at least one eye of the viewer; and
spatially-adjusting the area of interest of the projected image for the at least one eye; and displaying the number of projections for each eye of the viewer based on the received visual blurring function of the viewer.

24. The method of claim 23, the method further comprising conducting a calibration of the 3D display system.

25. The method of claim 23, wherein conducting a calibration of the 3D display further comprises:
obtaining face image data and eye region image data for a viewer within a field of view of at least one camera in proximity to a 3D-enabled digital display;
detecting face and eye landmarks for the viewer in one or more image frames based on the face image data;
determining head pose information based on the face image data and eye region image data;
determining eye tracking information for the viewer based on the face image data, eye region image data, and head pose information, the eye tracking information including:
a. a point of regard (POR) of each eye of the viewer;
b. eye state of each eye of the viewer;
c. gaze direction of each eye of the viewer;
d. eye region illumination information for each eye of the viewer; and
e. a position of each eye of the viewer relative to the 3D-enabled digital display.

26. A method for assessing a visual acuity of a viewer of a 3D display, the method comprising:
a. using the 3D display to project a first sequence of images in three-dimensional space containing at least one object of intertest;
b. determining a first area of interest of each eye of the viewer via a point of regard;
c. determining a first level of fixation of each eye of the viewer;
d. correlating the determined area of interest of each eye of the viewer with the determined fixation of each eye of the viewer;
e. using the 3D display to project a second sequence of image in three-dimensional space containing at least one object of intertest in a second location;
f. determining a second area of interest of each eye of the viewer;
g. determining a second level of fixation of each eye of the viewer;
h. correlating the determined area of interest of each eye of the viewer with the determined second area of fixation of each eye of the viewer; and i. assessing an ability of the viewer to follow a movement of the at least one object of interest towards the second location and an ability of the viewer to fixate on the at least one object.

27. The method for assessing the visual acuity of a viewer of a 3D display of claim 26, further comprising:
   rendering a diagnosis of amblyopia based at least in part on the assessment of the ability of the viewer to follow a movement of the at least one object of interest towards the second location and an ability of the viewer to fixate on the at least one object.

28. The method of claim 27, wherein the visual blurring function for each of the eyes of the viewer is associated with the viewer in a digital record, the digital record comprising at least one of: a viewer identification, an age-appropriate content for 3D display, an interest appropriate content for 3D display, insurance carrier information, a prescribing medical professional, and an access frequency for administering treatment.

29. The method of claim 28, the method further comprising:
   a. receiving a visual blurring function for a second eye of the viewer;
   b. determining a gaze direction and the point of regard of the second eye of the viewer with regard to the 3D display;
   c. rendering a dynamic viewing session containing at least one object of interest, wherein the dynamic viewing session comprises a plurality of images for projection by the 3D display for the second eye, the rendering based at least in part on the visual blurring function for the second eye, the determined gaze direction and the point of regard of the second eye of the viewer, and the at least one object of interest;
   d. performing an assessment of an ability of the second eye to follow a movement of the at least one object of interest and an ability of the second eye of the viewer to fixate on the at least one object;
   e. adjusting spatially and temporally the at least one object in the rendered dynamic viewing session based at least in part on the assessment.

30. The method of claim 26, further comprising:
   prescribing a prescription for a treatment of amblyopia using a 3D display, wherein the prescription further comprises:
   a visual blurring function for each of the eyes of the viewer;
   a desired performance to fixate on an object of interest; and
   a desired ability of the viewer to follow a movement of the object of interest.

31. A method for treating amblyopia in a user using a 3D display, the method comprising:
   a. receiving a visual blurring function for a first eye of the viewer;
   b. determining a gaze direction and the point of regard of the first eye of the viewer with regard to the 3D display;
   c. rendering a dynamic viewing session containing at least one object of interest, wherein the dynamic viewing session comprises a plurality of images for projection by the 3D display for the first eye, the rendering based at least in part on the visual blurring function for the first eye, the determined gaze direction and the point of regard of the first eye of the viewer, and the at least one object of interest;
   d. performing an assessment of an ability of the first eye to follow a movement of the at least one object of interest and an ability of the first eye of the viewer to fixate on the at least one object;
   e. adjusting spatially and temporally the at least one object in the rendered dynamic viewing session based at least in part on the assessment.

* * * * *